United States Patent
Long et al.

(10) Patent No.: US 10,035,127 B2
(45) Date of Patent: *Jul. 31, 2018

(54) METAL-ORGANIC FRAMEWORKS WITH A HIGH DENSITY OF HIGHLY CHARGED EXPOSED METAL CATION SITES

(71) Applicant: The Regents of the University of California, Oakland, CA (US)

(72) Inventors: Jeffrey R. Long, Oakland, CA (US); Matthew T. Kapelewski, Berkeley, CA (US); Stephen J. Geier, Sackville (CA)

(73) Assignee: The Regents of the University of California, Oakland, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/033,748

(22) PCT Filed: Nov. 4, 2014

(86) PCT No.: PCT/US2014/063869
§ 371 (c)(1),
(2) Date: May 2, 2016

(87) PCT Pub. No.: WO2015/066693
PCT Pub. Date: May 7, 2015

(65) Prior Publication Data
US 2016/0250618 A1 Sep. 1, 2016

Related U.S. Application Data

(60) Provisional application No. 61/899,817, filed on Nov. 4, 2013.

(51) Int. Cl.
*B01J 20/22* (2006.01)
*C07C 65/03* (2006.01)
(Continued)

(52) U.S. Cl.
CPC ............ *B01J 20/226* (2013.01); *B01D 53/04* (2013.01); *B01J 20/28066* (2013.01);
(Continued)

(58) Field of Classification Search
CPC .. B01D 53/02; B01D 53/04; B01D 2253/204; B01D 2257/108; B01D 2258/02;
(Continued)

(56) References Cited

U.S. PATENT DOCUMENTS 2,684,967 A    7/1954   Berg
4,532,225 A    7/1985   Tsao
(Continued)

FOREIGN PATENT DOCUMENTS

CN    1910191 A    2/2007
CN    101270094 A    9/2008
(Continued)

OTHER PUBLICATIONS

Baharlou, Simin, International Preliminary Report on Patentability, PCT/US2014/063869, The International Bureau of WIPO, May 19, 2016.
(Continued)

*Primary Examiner* — Frank Lawrence
(74) *Attorney, Agent, or Firm* — Gavrilovich, Dodd & Lindsey LLP

(57) ABSTRACT

The disclosure provides for Metal-Organic Frameworks comprising $M_2$ (m-dobdc)-based cores, and methods of use thereof, including gas separation, gas storage, sensing, and other applications utilizing a high density of exposed metal cation sites.

26 Claims, 37 Drawing Sheets

(51) Int. Cl.
*B01J 20/28* (2006.01)
*C01B 3/00* (2006.01)
*B01D 53/04* (2006.01)
*B01J 31/16* (2006.01)
*C07C 65/05* (2006.01)
*B01D 53/02* (2006.01)

(52) U.S. Cl.
CPC ......... *B01J 31/1691* (2013.01); *C01B 3/0015* (2013.01); *C07C 65/03* (2013.01); *C07C 65/05* (2013.01); *B01D 53/02* (2013.01); *B01D 2253/204* (2013.01); *B01D 2257/108* (2013.01); *B01D 2258/02* (2013.01); *Y02C 10/08* (2013.01); *Y02E 60/328* (2013.01)

(58) Field of Classification Search
CPC ........................ B01J 20/226; B01J 20/28066; B01J 31/1691; C01B 3/0015; C07C 65/03; C07C 65/05; Y02C 10/08; Y02E 60/328
USPC ........ 95/90, 96, 139, 143, 146, 127; 96/108, 96/154; 502/400, 401
See application file for complete search history.

(56) References Cited

U.S. PATENT DOCUMENTS

| | | | |
|---|---|---|---|
| 5,064,804 A | 11/1991 | Soo | |
| 5,160,500 A | 11/1992 | Chu | |
| 5,208,335 A | 5/1993 | Ramprasad | |
| 5,648,508 A | 7/1997 | Yaghi | |
| 5,733,505 A | 3/1998 | Goldstein | |
| 5,779,904 A | 7/1998 | Ruderman | |
| 6,479,447 B2 | 11/2002 | Bijl | |
| 6,501,000 B1 | 12/2002 | Stibrany | |
| 6,617,467 B1 | 9/2003 | Mueller | |
| 6,624,318 B1 | 9/2003 | Mueller | |
| 6,686,428 B2 | 2/2004 | Zhang | |
| 6,893,564 B2 | 5/2005 | Mueller | |
| 6,929,679 B2 | 8/2005 | Mueller | |
| 6,930,193 B2 | 8/2005 | Yaghi | |
| 7,196,210 B2 | 3/2007 | Yaghi | |
| 7,202,385 B2 | 4/2007 | Mueller | |
| 7,229,943 B2 | 6/2007 | Gibson | |
| 7,279,517 B2 | 10/2007 | Mueller | |
| 7,309,380 B2 | 12/2007 | Mueller | |
| 7,343,747 B2 | 3/2008 | Mueller | |
| 7,411,081 B2 | 8/2008 | Mueller | |
| 7,524,444 B2 | 4/2009 | Hesse | |
| 7,582,798 B2 | 9/2009 | Yaghi | |
| 7,637,983 B1 | 12/2009 | Liu | |
| 7,815,716 B2 | 10/2010 | Mueller | |
| 8,343,260 B2 | 1/2013 | Omary | |
| 8,480,955 B2 | 7/2013 | Yaghi | |
| 8,501,150 B2 | 8/2013 | Schubert | |
| 8,518,264 B2 | 8/2013 | Kiener | |
| 8,524,932 B2 | 9/2013 | Leung | |
| 8,709,134 B2 | 4/2014 | Yaghi | |
| 8,735,161 B2 | 5/2014 | Yaghi | |
| 8,742,152 B2 | 6/2014 | Yaghi | |
| 9,078,922 B2 | 7/2015 | Yaghi | |
| 2003/0004364 A1 | 1/2003 | Yaghi | |
| 2003/0078311 A1 | 4/2003 | Muller | |
| 2003/0148165 A1 | 8/2003 | Muller | |
| 2003/0222023 A1 | 12/2003 | Mueller | |
| 2004/0081611 A1 | 4/2004 | Muller | |
| 2004/0225134 A1 | 11/2004 | Yaghi | |
| 2004/0249189 A1 | 12/2004 | Mueller | |
| 2004/0265670 A1 | 12/2004 | Muller | |
| 2005/0004404 A1 | 1/2005 | Muller | |
| 2005/0014371 A1 | 1/2005 | Tsapatsis | |
| 2005/0124819 A1 | 6/2005 | Yaghi | |
| 2005/0154222 A1 | 7/2005 | Muller | |
| 2005/0192175 A1 | 9/2005 | Yaghi | |
| 2006/0057057 A1 | 3/2006 | Muller | |
| 2006/0135824 A1 | 6/2006 | Mueller | |
| 2006/0154807 A1 | 7/2006 | Yaghi | |
| 2006/0185388 A1 | 8/2006 | Muller | |
| 2006/0252641 A1 | 11/2006 | Yaghi | |
| 2006/0252972 A1 | 11/2006 | Pilliod | |
| 2006/0287190 A1 | 12/2006 | Eddaoudi | |
| 2007/0068389 A1 | 3/2007 | Yaghi | |
| 2007/0202038 A1 | 8/2007 | Yaghi | |
| 2007/0217982 A1 | 9/2007 | Wright | |
| 2007/0248575 A1 | 10/2007 | Connor | |
| 2008/0017036 A1 | 1/2008 | Schultink | |
| 2008/0190289 A1 | 8/2008 | Muller | |
| 2009/0155588 A1 | 6/2009 | Hesse | |
| 2009/0183996 A1 | 7/2009 | Richter | |
| 2009/0216059 A1 | 8/2009 | Reyes | |
| 2009/0247654 A1 | 10/2009 | Rajendran | |
| 2010/0029476 A1* | 2/2010 | Trukhan | B01D 53/02 502/401 |
| 2010/0069234 A1 | 3/2010 | Willis | |
| 2010/0258004 A1 | 10/2010 | Matzger et al. | |
| 2011/0015388 A1 | 1/2011 | Youngblood | |
| 2011/0282067 A1 | 11/2011 | Li | |
| 2011/0282071 A1 | 11/2011 | Shi | |
| 2012/0028846 A1 | 2/2012 | Yaghi | |
| 2012/0031268 A1 | 2/2012 | Yaghi | |
| 2012/0130113 A1 | 5/2012 | Yaghi | |
| 2012/0133939 A1 | 5/2012 | Yaghi | |
| 2013/0047849 A1 | 2/2013 | Zhang | |
| 2013/0096210 A1 | 4/2013 | Yaghi | |
| 2014/0037944 A1 | 2/2014 | Dichtel | |
| 2014/0061540 A1* | 3/2014 | Long | B01D 53/02 252/373 |
| 2014/0148596 A1 | 5/2014 | Dichtel | |
| 2016/0159713 A1* | 6/2016 | Long | C07C 7/12 556/147 |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| JP | 2007534658 A | 11/2007 |
| KR | 20100055350 A | 5/2010 |
| WO | 9905151 A1 | 2/1999 |
| WO | 2006110740 A2 | 10/2006 |
| WO | 2006122920 A1 | 11/2006 |
| WO | 2006125761 A2 | 11/2006 |
| WO | 2007007113 A2 | 1/2007 |
| WO | 2007118843 A1 | 10/2007 |
| WO | 2009073739 A1 | 6/2009 |
| WO | 2010056092 A2 | 5/2010 |
| WO | 2010080618 A2 | 7/2010 |
| WO | 2010083418 A1 | 7/2010 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Mendo Perez, Jose, International Search Report and Written Opinion, PCT/US2014/063869, European Patent Office, dated Jan. 29, 2015.

Kapelewski, Matthew T., et al. "M2(m-dobdc) (M = Mg, Mn, Fe, Co, Ni) Metal-Organic Frameworks Exhibiting Increased Charge Density and Enhanced H2 Binding at the Open Metal Sites", J. Am. Chem. Soc., 2014, 136, pp. 12119-12129.

Zhou, Wei et al., "Enhanced H2 Adsorption in Isostructural Metal-Organic Frameworks with Open Metal Sites: Strong Dependence of the Binding Strength on Metal Ions", J. Am. Chem. Soc., 2008, 130, pp. 15268-15269.

Akporiaye et al., 'Combinatorial Approach to the Hydrothermal Synthesis of Zeolites,' Angew. Chemie 37(5):609-611 (1998).

(56) References Cited

OTHER PUBLICATIONS

Barman et al., 'Incorporation of active metal sites in MOFs via in situ generated ligand deficient metal-linker complexes' Chem. Commun. 47:11882-11884 (Oct. 11, 2011).
Bhakta et al., 'Metal organic frameworks as templates for nanoscale NaAlH4', Journal of American Chemical Society, vol. 131, No. 37, Sep. 23, 2009, pp. S1-S14.
Britt et al., "Metal-Organic frameworks with high capacity and selectivity for harmful gases", PNAS, 2008, vol. 105, No. 33, pp. 11623-11627.
Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.
Burrows, Andrew D., et al., "Post-Synthetic Modification of Tagged MOFs", Angewa. Chem. Int . Ed., (Oct. 20, 2008), vol. 47, pp. 8482-8486, XP008150669, (2008).
Carboni et al., "Highly porous and stable metal-organic frameworks for uranium extraction," Chemical Science, 4:2396-2402, Apr. 4, 2013.
Carlucci et al., 'Nanoporous three-dimensional networks topologically related to cooperite from the self-assembly of copper(I)centres and 1,2,4,5-tetracyanobenzene,' New J. Chem. 23(23):397-401 (1999).
Chen et al. "Photoluminescent Metal-Organic Polymer Constructed from Trimetallic Clusters and Mixed Carboxylates", Inorg. Chem. 2003, 42, 944-946.
Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
Chen, Binling, et. al., "Zeolitic imidazolate framework materials: recent progress in synthesis and applications", Journal of Materials Chemistry A: Materials for Energy and Sustainability, GB, (Jul. 17, 2014), vol. 2, No. 40, doi:10.1039/C4TA02984D, ISSN 2050-7488, pp. 16811-16831, XP055337959, (2014).
Choi et al., 'Reversible Interpenetration in a Metal-Organic Framework Triggered by Ligand Removal and Addition,' Angew. Chem. Int. Ed. 51:8791 -8795 (2012).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.
Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Corma et al., 'A large-cavity zeolite with wide pore windows and potential as an oil refining catalyst,' Nature, vol. 418, pp. 514-517 (Aug. 2002).
Corma et al., "From MOFs to zeolites: zirconium sites for epoxide rearrangement," New J. of Chem. 37:3496-3502, Aug. 2, 2013.
Coskun et al., 'Metal-Organic Frameworks Incorporating Copper-Complexed Rotaxanes,' Angew. Chem. Int. Ed., 51:2160-2163 (2012).
Costa et al., 'Chemical Modification of a Bridging Ligand Inside a Metal-Organic Framework while Maintaining the 3D Structure,' Eur. J. Inorg. Chem. 10:1539-1545 (2008).
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Demessence, A et al., 'Strong C02 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 66-100.
Dhakshinamoorthy et al., "Metal-organic frameworks as heterogeneous catalysts for oxidation reactions", Catal. Sci. Technol., Apr. 28, 2011, 1, 856-867.
Dietzel, Pascal D. C., et. al., "Application of metal-organic frameworks with coordinatively unsaturated metal sites in storage and separation of methane and carbon dioxide", Journal of Materials Chemistry, (Aug. 21, 2009), vol. 19, No. 39, doi:10.1039/b911242a, ISSN 0959-9428, pp. 7362-7370, XP055197279, (2009).
Koh et al., 'A Crystalline Mesoporous Coordination Copolymer with High Microporosity,' Angew Chem Int'l, 2008, pp. 677-680, vol. 47.
Koh et al., "A Crystalline Mesoporous Coordination Copolymer with High Microporosity", Angew. Chem. Int. Ed. 2008, 120, pp. 689-692.
Kong et al., 'Mapping of Functional Groups in Metal-Organic Frameworks', Science, vol. 341, No. 6148, Jul. 25, 2013, pp. 882-885.
Koza et al., 'An efficient High Yielding Approach for the Homocoupling of Aryl Boronic Acids,' Synthesis 15:2183-2186 (2002).
Kyoungmoo et al., "A Crystalline Mesoporous Coordination Copolymer with High Microporosity," Angew. Chem. Int. Ed. 47(4):689-92 (2008).
Ling et al., 'A zinc(II) metal-organic framework based on triazole and dicarboxylate ligands for selective adsorption of hexane isomers,' Chem. Comm. 47:7197-7199 (2011).
Lou et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Mason, Jarad A., "Evaluating metal-organic frameworks for natural gas storage", Chemical Science, vol. 5, Accepted Oct. 22, 2013, pp. 32-51.
McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.
Mendoza-Cortes et al., 'Adsorption Mechanism and Uptake of Methane in Covalent Organic Frameworks: Theory and Experiment,' J. Phys. Chem. 114:10824-10833 (2010).
Morris et al., 'Framework mobility in the metal-organic framework crystal IRMOF-3: Evidence for aromatic ring and amine rotation,' Journal of Molecular Structure 1004:94-101 (2011).
Morris et al., 'Synthesis, Structure, and Metalation of Two New Highly Porous Zirconium Metal-Organic Frameworks,' Inorg. Chem. 51:6443-6445 (Jun. 7, 2012).
O'Keeffe et al., 'Deconstructing the Crystal Structures of Metal-Organic Frameworks and Related Materials into Their Underlying Nets,' Chem. Rev. 112(2):675-702 (Feb. 8, 2012).
Oisaki et al., "A Metal-Organic Framework with Covalently Bound Organometallic Complexes," J. of the Amer. Chem. Soc., pp. 9262-9264, vol. 132, No. 27, 2010.

(56) References Cited

OTHER PUBLICATIONS

Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Tranchemontagne et al., 'Hydrogen Storage in New Metal-Organic Frameworks,' J. Phys. Chem. C 116 (24):13143-13151 (May 24, 2012).
Vitillo et al., 'Role of Exposed Metal Sites in Hydrogen Storage in MOFs,' J. Am. Chem. Soc. 130(26):8386-8396 (2008).
Wang, Zhenqiang, et al., 'Postsynthetic Covalent Modification of a Neutral Metal—Organic Framework', J. Chem. Soc., (2007), vol. 129, No. 41, pp. 12368-12369.
Whiffield et al. Metal-organic frameworks based on iron oxide octahedral chains connected by benzendicarboxylate dianions. Solid State Sciences, 2005. vol. 7, pp. 1096-1103.
Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).
Yang et al., 'CH4 storage and CO2 capture in highly porous zirconium oxide based metal-organic frameworks,' Chem. Commun., 48:9831-9833, Aug. 15, 2012.
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Zhenqiang Wang et al., 'Tandem Modification of Metal-Organic Frameworks by a Postsynthetic Approach', Angew Chem Int Ed, (200800686), vol. 47, pp. 4699-4702, (2008).
Zhou et al., 'Introduction to Metal-Organic Frameworks,' Chemical Reviews 112:673-674 (Jan. 26, 2012).
Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
Dugan et al., 'Covalent modification of a metal-organic framework with isocyanates: probing substrate scope and reactivity,' 29:3366-3368 (2008).
Eddaoudi, M et al., "Systematic Design of Pore Size and Functionality in Isoreticular MOFs and Their application in Methane Storage" Science, (2002), vol. 295, pp. 469-472.
Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).
Fracaroli et al., 'Isomers of Metal-Organic Complex Arrays,' Inorg. Chem. 51: 6437-6439 (Jun. 5, 2012).
Fracaroli, A.M. et al., 'Metal-Organic Frameworks with Precisely Designed Interior for Carbon Dioxide Capture in the Presence of Water, J. Am. Chem. Soc, Jun. 25, 2014, vol. 136, No. 25, pp. 8863-8866.
Furukawa et al., 'Isoreticular Expansion of MetalOrganic Frameworks with Triangular and Square Building Units and the Lowest Calculated Density for Porous Crystals,' Inorg. Chem. 50:9147-9152 (2011).
Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).
Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.
Gadzikwa, T. et al., 'Selective Bifunctional Modification of a Non-catenated Metal-Organic Framework Material via Click Chemistry,' J. Am. Chem. Soc. 131:13613-13615 (2009).
Galli et al., 'Adsorption of Harmful Organic Vapors by Flexible Hydrophobic Bis-pyrazolate Based MOFs,' Chem. Mater. 22(5):1664-1672 (2010).
Gandara et al., 'High Methane Storage Capacity in Aluminum Metal-Organic Frameworks', Journal of the American Chemical Society, vol. 136, No. 14, Mar. 21, 2014, pp. 5271-5274.
Gandara et al., 'Porous, Conductive Metal-Triazolates and Their Structural Elucidation by the Charge-Flipping Method,' Chem. Eur. J. 18:10595-10601 (2012).
Gandara, Felipe, et al., "Crystallography of metal-organic frameworks", IUCRJ, vol. 1, No. 6, Oct. 28, 2014, pp. 563-570.
Garibay et al., "Isoreticular synthesis and modification of frameworks with the UiO-66 topology," Chemical Communications, 46:7700-7702, Sep. 27, 2010.
Gassensmith et al., 'Strong and Reversible Binding of Carbon Dioxide in a Green Metal-Organic Framework,' J. Am. Chem. Soc. 133:15312-15315 (Aug. 30, 2011).
Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).
Goto, Y et al., "Clickable Metal-Organic Framework," J. Am. Chem. Soc. 130:14354-14355 (2008).
Han et al., 'Covalent Organic Frameworks as Exceptional Hydrogen Storage Materials,' J. Am. Chem. Soc. 130: 11580-11581 (2008).
Kirai et al., 'Homocoupling of arylboronic acids catalyzed by 1,10-phenanthroline—ligated copper complexes in air,' European Journal of Organic Chemistry 12:1864-1867 (2009).

* cited by examiner

FIGURE 20A-D

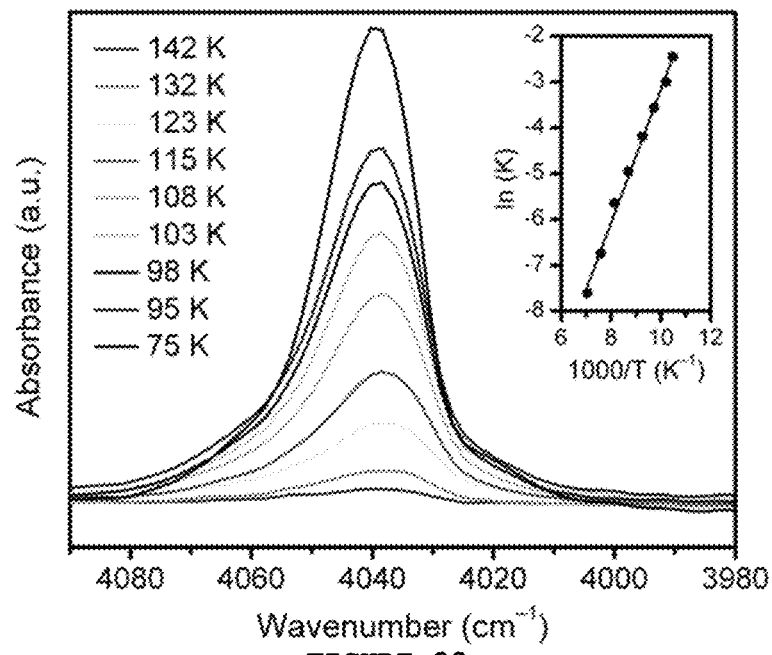
FIGURE 23
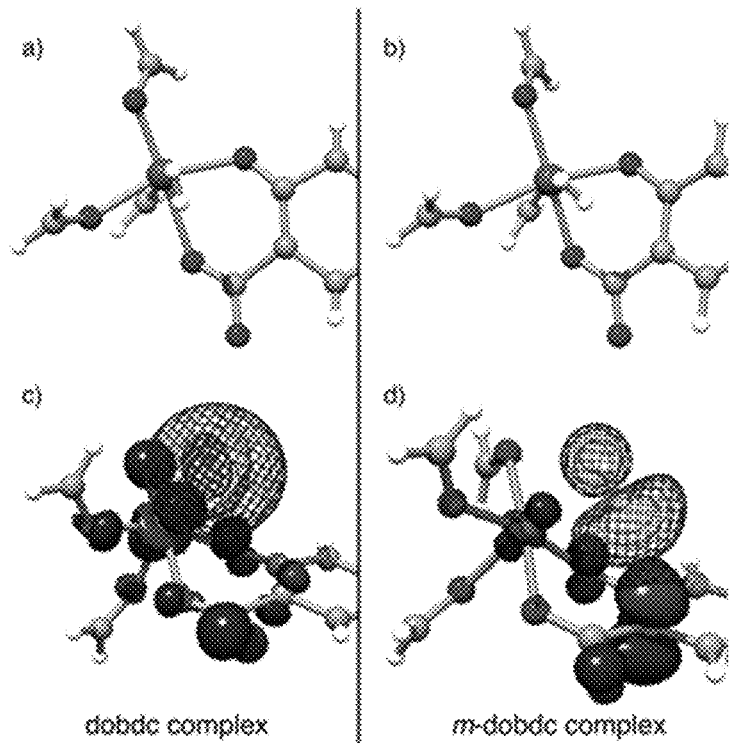
FIGURE 24A-D

METAL-ORGANIC FRAMEWORKS WITH A HIGH DENSITY OF HIGHLY CHARGED EXPOSED METAL CATION SITES

CROSS REFERENCE TO RELATED APPLICATIONS

This application is a U.S. National Stage Application filed under 35 U.S.C. § 371, and claims priority to International Application No. PCT/US2014/063869, filed Nov. 4, 2014, which application claims priority under 35 U.S.C. § 119 from Provisional Application Ser. No. 61/899,817, filed Nov. 4, 2013, the disclosures of which are incorporated herein by reference.

STATEMENT REGARDING GOVERNMENT SPONSORSHIP

This invention was made with government support under grant numbers DE-AR0000251 awarded by the Advanced Research Projects Agency (ARPA) and DE-AC02-05CH11231 awarded by the U.S. Department of Energy (DOE). The government has certain rights in the invention.

TECHNICAL FIELD

The disclosure provides for metal-organic frameworks (MOFs) comprising $M_2$ (m-dobdc)-based cores, and methods of use thereof, including gas separation, gas storage, catalysis, filters and sensors.

BACKGROUND

Atmospheric carbon dioxide levels recently surpassed 400 ppm, the highest concentration seen on the Earth in over three million years. These record levels and the rate at which these levels are increasing are due in large part to anthropogenic emissions from the combustion of fossil fuels. Therefore, reducing $CO_2$ emissions and using carbon-neutral fuels is of paramount importance for society. The transportation sector is an especially important target, as 27% of overall greenhouse gas emissions are from automobiles. Replacing fossil fuels with a carbon-neutral fuel such as hydrogen or natural gas (methane) would be advantageous due to hydrogen's high gravimetric energy content, clean combustion, and potential renewability and the higher amount of energy derived from natural gas per unit of $CO_2$ emitted. The widespread adoption of hydrogen and methane as fuels, however, is limited because they are gases at room temperature and pressure. Most efforts to increase the volumetric energy density of these gases in fuel tanks have relied on cryogenic storage and/or compression, but these strategies have proven too costly for the widespread adoption of either for fueling motor vehicles. Large cooling and compressing systems contribute additional unwanted mass to motor vehicles and require a significant energetic cost to store hydrogen at a useful density. Alternatively, solid adsorbents provide promise as a way to store $H_2$ at high densities while simultaneously using lower pressures and higher temperatures than are currently employed. The U.S. Department of Energy (DOE) has set targets for on-board $H_2$ storage of 5.5 wt % gravimetric capacity, 40 g/L volumetric capacity, a temperature range of −40 to 60° C., and a maximum delivery pressure of 100 atm. Unfortunately, currently available adsorbents do not have the requisite capacities at relevant temperatures and pressures. Furthermore, binding enthalpies in the range of −15 to −20 kJ/mol are necessary for practical $H_2$ storage and have yet to be achieved, leading to the need for further development of solid porous adsorbents for $H_2$ storage.

SUMMARY

Provided herein are highly ordered porous metal-organic frameworks (MOFs) that are comprised of metals, metal ions, and/or metal-containing complexes that are linked by 4,6-dioxido-1,3-benzenedicarboxylate based linking moieties. The MOFs disclosed herein are metal-organic frameworks that have a high density of coordinatively unsaturated metal centers (alternately known as open metal coordination sites and exposed metal cation sites). Additionally, these coordinatively unsaturated metal centers have a high positive charge as a result of the design of the bridging ligand. Consequently, the MOFs disclosed herein exhibit higher isosteric heats of adsorption for hydrogen in comparison to other frameworks known in the art. Moreover, the MOFs of the disclosure exhibited stronger $H_2$ binding enthalpy in comparison to other frameworks known in the art as determined by variable temperature infrared spectroscopy. Neutron diffraction was used to supplement these techniques by determining the sites of $D_2$ occupation and fractional occupancies of each site within the pores of the frameworks. Computational results attributed this increased binding strength to an increased polarization interaction with the metal coupled with a stronger backdonation from the metal-ligand complex to the $H_2$ from a delocalized pi orbital on both the metal and linker. Based on these results, other applications are posited for this family of frameworks; since such geometries with a high density of exposed metal cation sites are used in many applications, this family of frameworks, based on their superior properties for $H_2$ storage, can be used for a wide range of applications as well. Further, by altering functional groups on the linking moiety one can subtly control framework properties for additional applications.

In a particular embodiment, the disclosure provides for a porous metal-organic framework (MOF) comprising a plurality of cores, wherein the plurality of cores comprise two or more metals, metal ions, and/or metal containing complexes that are linked together by forming covalent bonds with oxide and/or carboxylate linking clusters of 4,6-dioxido-1,3-benzenedicarboxylate ("m-dobdc") based linking moieties.

In another embodiment, a MOF of the disclosure comprises one or more cores which are comprised of linking moieties having a structure of Formula I:

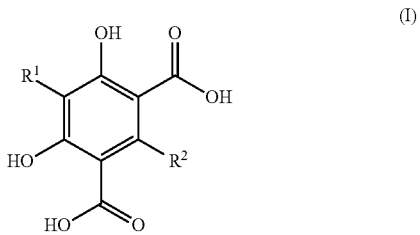

wherein, $R^1$-$R^2$ are independently selected from H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, and optionally substituted mixed ring system. A porous metal-organic framework (MOF) comprising a plurality of cores, wherein the plurality of cores comprises two or more metals, metal ions, and/or metal containing complexes that are linked together by forming covalent bonds with oxide and/or carboxylate linking clusters of 4,6-dioxido-1,3-benzenedicarboxylate ("m-dobdc") based linking moieties. In a further embodiment, the linking moieties having a structure of Formula I:

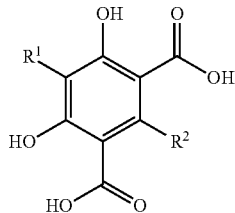

(I)

wherein, $R^1$-$R^2$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted heteroaryl, CN, CO, $NH_2$, OR, $NR_2$, $PR_2$, SR, F, Cl, Br, and I. In yet another embodiment, the linking moieties having a structure of Formula I:

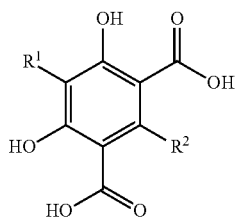

(I)

wherein, $R^1$-$R^2$ are independently selected from H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted heteroaryl, CN, CO, $NH_2$, OR, $NR_2$, $PR_2$, SR, F, Cl, Br, and I. In a certain embodiment, a MOF of the disclosure comprises one or more cores which are comprised of linking moieties having a structure of Formula I:

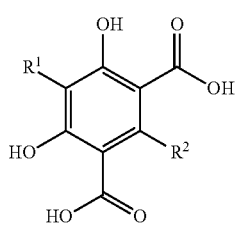

(I)

wherein, $R^1$-$R^2$ are independently selected from H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, optionally substituted ($C_1$-$C_5$)heteroalkynyl, optionally substituted aryl, optionally substituted heteroaryl, $NH_2$, $NR_2$, OR, $PR_2$, SR, F, Cl, Br, and I. In a preferred embodiment, the linking moieties having a structure of Formula I(a):

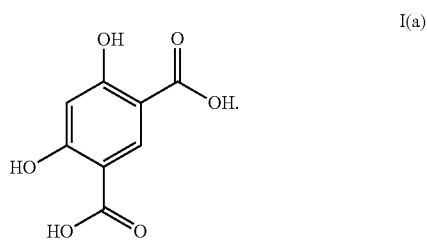 [SMILES: O=C(O)c1cc(C(=O)O)c(O)cc1O]

I(a)

In another embodiment, a MOF of the disclosure comprises one or more cores which are comprised of metals, metal ions, and/or metal containing complexes that are selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and any combination thereof, including any complexes which contain the metals or metal ions listed above, and any corresponding metal salt counter-anions. In yet another embodiment, the metal ions are selected from $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$. In a further embodiment, the metal ions are selected from $Mg^{2+}$, $Mn^{2+}$, $Fe^{2+}$, $Co^{2+}$, and $Ni^{2+}$.

In a particular embodiment, the disclosure provides for a MOF disclosed herein that is activated by removing guest molecules and/or solvents.

In another embodiment, the disclosure provides for a MOF disclosed herein that is reacted with one or more post framework reactants. In a further embodiment, one or more post framework reactants add at least one effect to the MOF of the disclosure selected from: modulates the gas storage ability of the MOF; modulates the sorption properties of the MOF; modulates the gas separation properties of the MOF;

modulates the adsorbate storage ability of the MOF; modulates the adsorbate separation ability of the MOF; modulates the density of exposed metal cation sites; modulates the charge distribution in the framework; modulates the charge density at the exposed metal cation site; modulates the pore size of the MOF; modulates the catalytic activity of the MOF; modulates the conductivity of the MOF; and modulates the sensitivity of the MOF to the presence of an analyte of interest.

In a particular embodiment, the disclosure provides for a MOF disclosed herein that further comprising one or more absorbed or adsorbed chemical species. Examples of such species include but are not limited to, gases, optionally substituted ($C_1$-$C_{25}$) organic molecules, inorganic molecules, liquids, and combinations thereof. In a preferred embodiment, the adsorbed or absorbed chemical species is hydrogen.

In a certain embodiment, the disclosure provides a method to separate or store one or more gases from a mixed gas mixture comprising contacting the gas mixture with a MOF of the disclosure. In a preferred embodiment, the gas that is separated from the gas mixture and stored is hydrogen. In a further embodiment, the gas mixture comprises hydrogen gas formed from steam reforming, electrolysis, and thermolysis processes.

In a particular embodiment, the disclosure provides a method to separate or store one or more adsorbates from a mixture of adsorbates comprising contacting the mixture with a MOF of the disclosure.

In a certain embodiment, the disclosure provides for a device comprising a MOF of the disclosure, or a binder and a MOF of the disclosure. For example, a device of the disclosure can comprise the MOF or a mixture of the MOF and binder or other additive as described herein that form a porous composite of 0.1-10 mm size. In a further embodiment, the device is a gas storage or gas separation device. Examples of gas storage or gas separation devices include, but are not limited to purifiers, filters, scrubbers, pressure or temperature swing adsorption devices, hollow fiber membranes, ceramic membranes, cryogenic air separation devices, and hybrid gas separation devices.

In a particular embodiment, a MOF of the disclosure further comprises an adsorbed or absorbed chemical species selected from methane, natural gas, carbon dioxide, carbon monoxide, oxygen, nitrogen, helium, neon, argon, krypton, xenon, ethane, ethylene, acetylene, propane, propylene, butane, 2-methylpropane, 1-butene, cis-2-butene, trans-2-butene, 2-methylpropene, ammonia, $SO_2$, $SO_3$, NO, $NO_2$, $N_2O$, or other adsorbates in a gas or liquid phase.

In another embodiment, a MOF of the disclosure comprises exposed metal cation sites (open metal coordination sites) that adsorb, absorb, or interact with a substrate or guest. In a further embodiment, the exposed metal cation sites adsorb, absorb, or interact with a post-framework reactant.

In a particular embodiment, a MOF disclosed herein is used to adsorb, absorb, or interact with a substrate or guest. In another embodiment, a MOF of the disclosure is used in the separations of a chemical species in a mixture. In yet another embodiment, A MOF disclosed herein is incorporated into a membrane. In a further embodiment, a MOF disclosed herein is coated on a surface. In yet a further embodiment, a MOF of the disclosure is in a membrane or coated on a surface in a device. In a certain embodiment, a MOF disclosed herein is used for the separation of mixtures selected from $O_2$/air, $CO_2$/$N_2$, $CO_2$/$H_2$, CO/$H_2$, ethane/ethylene, propane/propylene/acetylene, saturated/unsaturated hydrocarbons, methane purification, butene isomer separation (1-butene, cis-2-butene, trans-2-butene, isobutylene), mixtures of hexane isomers, and BTEX mixtures (benzene, toluene, ethylbenzene, p-xylene, o-xylene, and m-xylene). In a preferred embodiment, a MOF of the disclosure is used to store any adsorbate selected from $H_2$, $CH_4$, natural gas and $CO_2$. In an alternate embodiment, a MOF disclosed herein is used as a catalyst or as a vehicle for a catalyst.

In a particular embodiment, the disclosure provides that the structure of a MOF disclosed herein is defined by its powder diffraction pattern and/or the metal coordination environment.

DESCRIPTION OF DRAWINGS

FIG. 23 provides variable temperature infrared spectrum of $Co_2$ (m-dobdc). The inset shows the van't Hoff plot that is used to extract the enthalpy and entropy change in $H_2$ upon adsorption to the open metal site. Lines go from 142 K (bottom) to 75K (top).

FIG. 24A-D provides illustrations of the calculated binding modes of $H_2$ in (A) the dobdc complex and (B) the m-dobdc complex. Note the $H_2$ shift toward the linker in the m-dobdc complex and its different orientation relative to the metal. The corresponding complementary occupied virtual orbital pairs are shown for (C) the dobdc complex and (D) the m-dobdc complex, with occupied and virtual orbitals shown as solid and mesh, respectively, at a 0.05 $Å^{-3/2}$ isodensity. These orbitals show the direct involvement of the linker in the charge transfer through backbonding donation from the pi system in the m-dobdc not present in dobdc.

DETAILED DESCRIPTION

Figure 1:
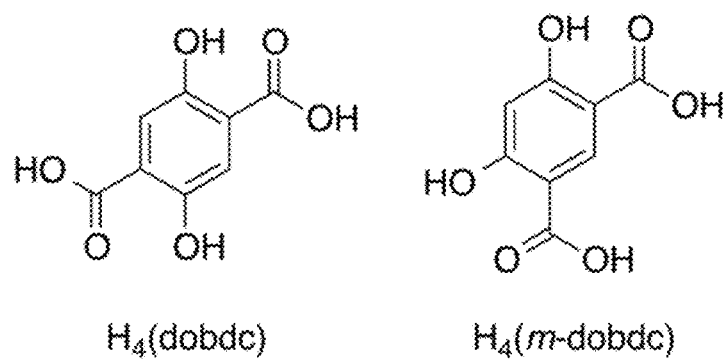
FIG. 1 provides a comparison of the $H_4$ (dobdc) (dobdc=2,5-dioxido-1,4-benzenedicarboxylate) and $H_4$ (m-dobdc) (m-dobdc=4,6-dioxido-1,3-benzenedicarboxylate) linkers.
Figure 2:
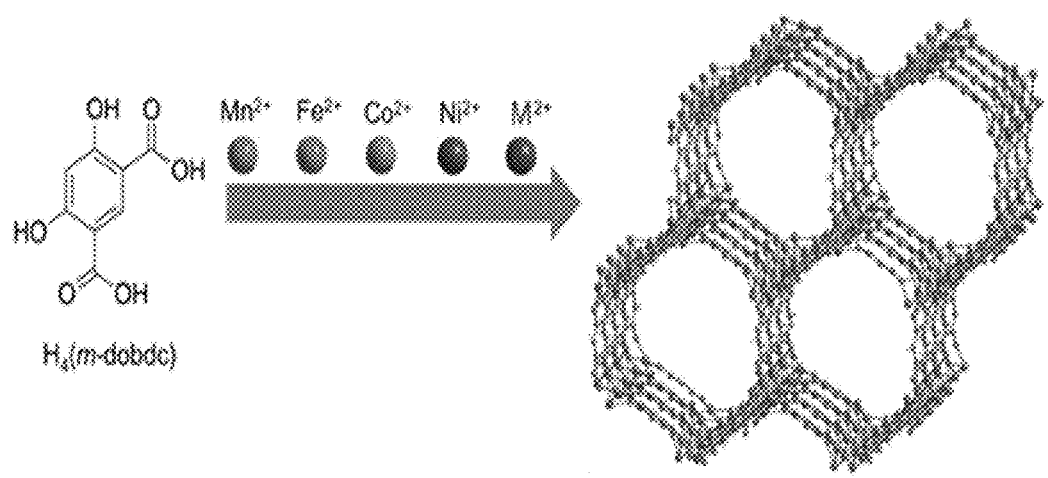
FIG. 2 diagrams that when a regioisomeric (m-dobdc) linker is reacted with a divalent metal ion (such as $Mn^{2+}$, $Fe^{2+}$, $Co^{2+}$, $Ni^{2+}$, or $M^{2+}$, wherein M represents a metal) a framework is generated with a modified geometry and altered electronics around the open metal coordination sites in the framework.
Figure 3:
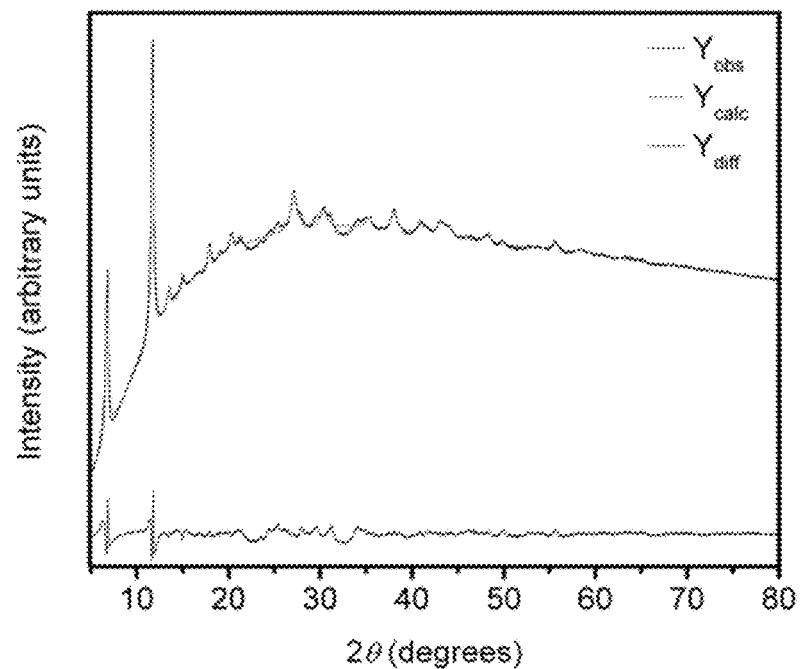
FIG. 3 presents a powder X-ray diffraction pattern of $Mn_2$ (m-dobdc) ($Y_{obs}$ top line) with calculated diffraction pattern ($Y_{calc}$; substantially overlaps with $Y_{obs}$) from Le Bail refinement with difference (bottom). Unit cell parameters: a axis, 25.8225(6) Å; c axis, 6.71(1) Å; V=3874 (1) Å$^3$.

As used herein and in the appended claims, the singular forms "a," "an," and "the" include plural referents unless the context clearly dictates otherwise. Thus, for example, reference to "a core" includes a plurality of such cores and reference to "the metal" includes reference to one or more metals and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art. Exemplary methods and materials are presented herein, although alternative, similar or equivalent methods and reagents will be readily identifiable to one of skill in the art.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

The term "alkyl" refers to an organic group that is comprised of carbon and hydrogen atoms that contains single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cluster" refers to identifiable associations of 2 or more atoms. Such associations are typically established by some type of bond or interaction: ionic, covalent, Van der Waals', coordinate, hydrogen bond, electrostatic, London Dispersion, and the like.

As used herein, a "core" refers to a repeating unit or units found in a MOF disclosed herein. The MOFs disclosed herein can comprise homogenous repeating cores, heterogeneous repeating cores or a combination of homogenous and heterogeneous cores. A core comprises a metal, metal ion, and/or metal containing complex or a cluster of metals, metal ions, and/or metal containing complexes that are linked to one of more linking moieties. Various linking moieties that make up cores are depicted as structures throughout the disclosure and are referred to as Formulas. The coordinate bonds, however, between metals and/or metal ions to various ligands, such as guest species, that arise from reagents or solvents have been omitted for clarity. Therefore, a person of skill in the art should assume that the metal and/or metal ions can and do form coordinate bonds with these ligands even though they are not visually depicted in the Formulas.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "framework" as used herein, refers to a highly ordered structure comprised of secondary building units (SBUs) that can be linked together in defined, repeated and controllable manner, such that the resulting structure is characterized as being porous, periodic and crystalline. Typically, "frameworks" are two dimensional (2D) or three dimensional (3D) structures. Examples of "frameworks" include, but are not limited to, "metal-organic frameworks" or "MOFs", "zeolitic imidazolate frameworks" or "ZIFs", or "covalent organic frameworks" or "COFs". While MOFs and ZIFs comprise SBUs of metals or metal ions linked together by forming covalent bonds with linking clusters on organic linking moieties, COFs are comprised of SBUs of organic linking moieties that are linked together by forming covalent bonds via linking clusters. As used herein, "framework" does not refer to coordination complexes or metal complexes. Coordination complexes or metal complexes are comprised of a relatively few number of centrally coordinated metal ions (i.e., less than 4 central metal ions) that are coordinately bonded to molecules or ions, also known as ligands or complexing agents. By contrast, "frameworks" are highly ordered and extended structures that are not based upon a centrally coordinated ion, but involve many repeated secondary building units (SBUs) linked together. Accordingly, "frameworks" are orders of magnitude much larger than coordination complexes and have different structural and chemical properties due to the framework's open and ordered structure.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "heterocycle", as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof.

Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

A "linking moiety" refers to a mono-dentate or polydentate organic compound that, through linking clusters, bind a metal or a plurality of metals, respectively. Generally, a linking moiety comprises a substructure having an alkyl or cycloalkyl group comprising 1 to 20 carbon atoms, an aryl group comprising 1 to 5 phenyl rings, a heterocycle group comprising 1 to 5 rings, or a combination of any of the foregoing, and in which one or more linking clusters are covalently bound to the substructure. A linking moiety may be further substituted post-synthesis of a metal organic framework by reacting with one or more reactants in side chain of a linking moiety after formation of the metal organic framework. In a particular embodiment, a "linking moiety" refers to a parent chain that contains at least one 4,6-dihydroxy-isophthalic acid moiety or derivative thereof that can bind at least one metal, metal ion, or metal containing complex.

The term "linking cluster" refers to one or more atoms capable of forming an association, e.g. covalent bond, polar covalent bond, ionic bond, and/or Van der Waals' interaction, with one or more atoms of another linking moiety, and/or one or more metal, metal ions, or metal containing complexes. A linking cluster can be part of the parent chain itself, e.g. the oxygen atoms in hydroxyl and/or carboxylic acid groups, and/or additionally can arise from functionalizing the parent chain, e.g. adding carboxylic acid and/or hydroxyl groups to an aryl based parent chain. A linking cluster can undergo a condensation reaction with a molecule to for a covalent bond. After condensation the linking cluster forms a bond to another atom. For example, a linking cluster can comprise OH, 1,2-diols, NN(H)N, N(H)NN, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and/or $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Generally, for the MOFs disclosed herein, the linking cluster(s) that bind one or metal or metal ions and/or associate with one or more atoms of another linking moiety comprise oxygen atoms of a 4,6-dihydroxy-isophthalic acid (m-dobdc) based parent chain. The m-dobdc based parent chain may be further substituted with one or more linking clusters, however, and can therefore form associations with one or more metal or metal ions and/or one or more atoms of another linking moiety in addition to, or alternatively to, the oxygen atom-based linking cluster(s) of the m-dobdc based parent chain. Generally, the linking clusters disclosed herein are Lewis bases, and therefore have lone pair electrons available and/or can be deprotonated to form stronger Lewis bases. The deprotonated version of the linking clusters, therefore, are encompassed by the disclosure and anywhere a linking cluster that is depicted in a non-deprotonated form, the deprotonated form should be presumed to be included, unless stated otherwise. For example, although the structural formulas presented herein are illustrated as having hydroxyls or carboxylic acids, for the purposes of this disclosure, these illustrated structures should be interpreted as including both hydroxyls and oxides, and carboxylic acids and carboxylates, respectfully.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

A "metal containing complex" refers to complexes of a metal or metal ion, wherein the metal or metal ion is centrally located and surrounded by a number of other molecules or ions. These molecules or ions are generally interacting with the central metal or metal ion through one or more coordinate bonds.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "post framework reactants" refers to all known substances that are directly involved in a chemical reaction. Post framework reactants typically are substances, molecules, or compounds which have not reached the optimum number of electrons in their outer valence levels, and/or have not reached the most favorable energetic state due to ring strain, bond length, low bond dissociation energy, and the like. Some examples of post framework reactants include, but are not limited to:

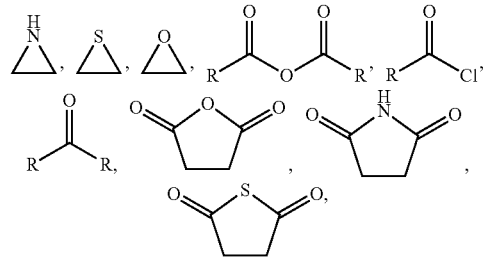

I—R, Br—R, $CR_3$—Mg—Br, $CH_2R$—Li, $CR_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "unsubstituted" with respect to hydrocarbons, heterocycles, and the like, refers to structures wherein the parent chain contains no substituents.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

Metal-organic frameworks are a well-known class of porous materials comprised of inorganic units bridged by coordinating organic linkers. In addition to possessing high internal surface areas, their physical and chemical properties can be tuned for specific applications by judicious choice of the organic ligand and metal. These properties lead to applications in storing and separating gases; in such applications, it is particularly important to have precise control over the strength and specificity of interactions between the pore surface and small gas molecules. Strong adsorption sites can be incorporated on the pore surface in order to selectively attract specific gas molecules for separation applications or to increase the density of gas molecules present for storage applications.

Exposed metal cations represent one example of strong adsorption sites that have successfully been incorporated in many metal-organic frameworks. These Lewis acidic sites, which are typically formed by removing metal-coordinated solvent molecules by heating under vacuum, are highly polarizing and have strong interactions with many small gas molecules. For example, the well-known $M_2$ (dobdc) (M=Mg, Mn, Fe, Co, Ni, Cu, Zn; dobdc$^{4-}$=2,5-dioxido-1,4-benzenedicarboxylate) framework, which is also known as $M_2$ (dhtp), CPO-27, and MOF-74, contains a high density of exposed metal cations and is especially promising for the storage of a wide variety of gases. As a result of its compact, highly charged tetra-anionic linker, this framework is endowed with an exceptionally high density of open metal coordination sites, which are the primary binding sites for small gas molecules such as $H_2$, $CH_4$, and $CO_2$. Therefore, $M_2$ (dobdc) frameworks have been used in a wide variety of applications involving gas adsorption, including $H_2$ storage (Dincä et al. *J. Am. Chem. Soc.* 128:16876 (2006); Zhou et al. *J. Am. Chem. Soc.* 130:15268 (2008); Queen et al. *Dalton Trans.* 41:4180 (2012); Dietzel et al. *Chem. Commun.* 959 (2006); Liu et al. *Langmuir* 24:4772 (2008); Sumida et al. *Chem. Commun.* 47:1157 (2011)), methane storage (Wu et al. *J. Am. Chem. Soc.* 131:4995 (2009); Dietzel et al. *J. Mater. Chem.* 19:7362 (2009); Makal et al. *Chem. Soc. Rev.* 41:7761 (2012); Peng et al. *J. Am. Chem. Soc.* 135:11887 (2013)), $CO_2$ capture (Dietzel et al. *Chem. Commun.* 5125 (2008); Caskey et al. *J. Am. Chem. Soc.* 130:10870 (2009); McDonald et al. *J. Am. Chem. Soc.* 134:7056 (2012); Yu et al. *Chem. Sci.*:3544 (2013)), and hydrocarbon separations (Bloch et al. *Science* 335:1606 (2012); Bao et al. *Langmuir* 27:13554 (2011); He et al. *Energy Environ Sci.* 5:9107 (2012); Geier et al. *Chem. Sci.* 4:2054 (2013)). All of these applications take advantage of strong interactions between gas molecules and exposed metal cations.

Discovering new frameworks with a high density of open metal coordination sites is not trivial. It is difficult to predict topologies that will contain a high density of exposed metal sites; even if this could be done, it is not yet possible to predict suitable conditions that will lead to a desired phase and it is often challenging to find such conditions experimentally. Rather than attempt to discover new materials, selectively tuning the most promising preexisting frameworks by altering the linker, the metal, or both is a viable strategy for enhancing the gas binding properties of metal-organic frameworks. Since the $M_2$ (dobdc) series of frameworks has been shown to be outstanding for binding small gas molecules and has very high thermal stability, experiments were performed to tune the electronics around the exposed metal cations which should subsequently tune the affinity for different gas molecules. For example, binding $H_2$ or $CH_4$ might be improved by decreasing electron density at the metal, thus increasing the ability of the metal to polarize and bind adsorbing gas molecules more strongly. Furthermore, $M_2$ (dobdc) offers the advantage of being an isostructural series of frameworks that can be formed with a variety of metals, which offers a further level of control for tuning the framework for specific interactions. Based on the high density of exposed metal cations, isostructural nature of these frameworks, and thermal stability, a combination which is not possessed by any other framework, $M_2$ (dobdc) provides an ideal platform for exploring the tunability of metal-organic frameworks to strengthen interactions with small gas molecules.

The disclosure provides for the synthesis of a metal-organic framework based on a linker that is an isomer of the $H_4$ (dobdc) linker. This MOF will be referred to as $M_2$ (m-dobdc) herein, wherein M=a metal, metal ion or metal ion containing complex and m-dobdc=4,6-dioxido-1,3-benzenedicarboxylate. Rather than having para carboxylic acid functionalities and para phenols, as in the regular $H_4$ (dobdc) linker, $H_4$ (m-dobdc) has meta carboxylic acid groups and meta phenols. This yields a previously unknown metal-organic framework structure with one-dimensional hexagonal channels and a high density of open metal coordination sites. This framework is particularly exceptional for binding $H_2$; it has higher isosteric heats of adsorption for $H_2$ as compared to other metal-organic frameworks, including $M_2$ (dobdc), which has a similarly high density of open metal coordination sites. While hydrogen is used as a probe, the additional positive charges at the exposed metal cation sites are advantageous for any application in which a high density of exposed metal cation sites is important or useful.

The disclosure provides MOFs comprising $M_2$ (m-dobdc) wherein M is a metal ion, metal, or metal containing complex. In the experiments, presented herein, $M_2$ (m-dobdc) was synthesized with M=Mg, Mn, Fe, Co, and Ni. The $Mn_2$ (m-dobdc), $Fe_2$ (m-dobdc), $Co_2$ (m-dobdc), and $Ni_2$ (m-dobdc) frameworks exhibited higher isosteric heats of adsorption for $H_2$ as compared with their isometallic $M_2$ (dobdc) counterparts. It is hypothesized that tuning the electronics around the open metal coordination sites leads to these increased isosteric heats of adsorption. Neutron diffraction of $D_2$ loaded samples was used in conjunction with infrared spectroscopy to further confirm this stronger $H_2$ binding enthalpy. Computational results attributed this increased binding strength to an increased polarization interaction with the metal coupled with a stronger backdonation from the metal-ligand complex to the $H_2$ from a delocalized pi orbital on both the metal and linker. The gas, $H_2$, is used as a probe to explore the electronic effects that are present around the open metal coordination sites in this $M_2$ (m-dobdc) series; $H_2$ was chosen due to its simplicity, polarizability, and potential use as a clean, renewable fuel. The results of higher binding enthalpies due to different electronics around these exposed cation sites imply strong interactions of these exposed cation sites with other small gas molecules, leading to the potential application of the $M_2$ (m-dobdc) series of frameworks in many other gas storage, capture, separations, and sensing applications.

Accordingly, the disclosure provides for MOFs that comprise repeating cores which comprise a plurality of metals, metal ions, and/or metal containing complexes that are linked together by forming covalent bonds with linking clusters on a plurality of linking moieties (e.g., m-dobdc). In a certain embodiment, the one or more metals, metal ions and/or metal containing complexes, that can be used in the (1) synthesis of a MOF of the disclosure, (2) exchanged post synthesis of a MOF disclosed herein, and/or (3) added to a MOF of the disclosure by forming coordination complexes with post framework reactant linking clusters, include, but are not limited to, the following: $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^+$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and any combination thereof, including any complexes which contain the metals or metal ions listed above, as well as any corresponding metal salt counter-anions.

In a further embodiment, one or more metal and/or metal ions that can be used in the (1) synthesis of a MOF of the disclosure, (2) exchanged post synthesis of a MOF disclosed herein, and/or (3) added to a MOF of the disclosure by forming coordination complexes with post framework reactant linking clusters, include, but are not limited to, the following: $Li^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Ce^{4+}$, $Ce^{3+}$, $Ce^{2+}$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, and combinations thereof, including any complexes which contain the metals or metal ions listed above, as well as any corresponding metal salt counter-anions.

In yet a further embodiment, one or more metal ions that can be used in the (1) synthesis of a MOF of the disclosure, (2) exchanged post synthesis of a MOF disclosed herein, and/or (3) added to a MOF of the disclosure by forming coordination complexes with post framework reactant linking clusters, include, but are not limited to, the following: $Li^+$, $Mg^{2+}$, $Ca^{2+}$, $Ba^{2+}$, $Zr^{4+}$, $Zr^{3+}$, $Zr^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $W^{6+}$, $W^{5+}$, $W^{4+}$, $W^{3+}$, $W^{2+}$, $W^+$, $V^{5+}$, $V^{4+}$, $V^{3+}$, $V^{2+}$, $Mn^{6+}$, $Mn^{5+}$, $Mn^{4+}$, $Mn^{3+}$, $Mn^{2+}$, $Mn^+$, $Fe^{6+}$, $Fe^{4+}$, $Fe^{3+}$, $Fe^{2+}$, $Fe^+$, $Fe$, $Co^{5+}$, $Co^{4+}$, $Co^{3+}$, $Co^{2+}$, $Co^+$, $Ni^{3+}$, $Ni^{2+}$, $Ni^+$, $Ni$, $Cu^{4+}$, $Cu^{3+}$, $Cu^{2+}$, $Cu^+$, $Zn^{2+}$, $Zn^+$, $Zn$, $Pd^{6+}$, $Pd^{4+}$, $Pd^{2+}$, $Pd^+$, $Cd^{2+}$, $Cd^+$, $Ce^{4+}$, $Ce^{3+}$, $Ce^{2+}$, and any combination thereof, including any complexes which contain the metal ions listed above, as well as any corresponding metal salt counter-anions.

In another embodiment, one or more metal ions in (1) synthesis of a MOF of the disclosure, (2) exchanged post synthesis of a MOF disclosed herein, and/or (3) added to a MOF of the disclosure by forming coordination complexes with post framework reactant linking clusters, is a divalent metal ion selected from the group comprising $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$. In yet a further embodiment, the divalent metal ion selected from the group comprising $Mg^{2+}$, $Mn^{2+}$, $Fe^{2+}$, $Co^{2+}$, and $Ni^{2+}$.

In a certain embodiment, a MOF of the disclosure comprises one or more cores comprising one or more linking moieties of structural Formula I:

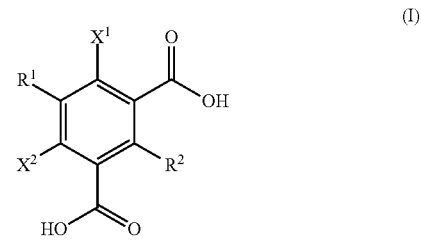

wherein, $X^1$-$X^2$ are independently selected from the group comprising hydroxyl, amine, thiol, and cyano;

$R^1$-$R^2$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, and optionally substituted mixed ring system.

In another embodiment, a MOF of the disclosure comprises one or more cores comprising one or more linking moieties of structural Formula I:

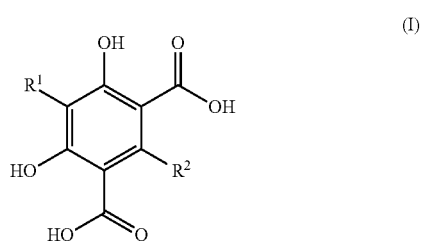

wherein, $R^1$-$R^2$ are independently selected from the group comprising H, D, optionally substituted FG, optionally substituted $(C_1$-$C_6)$alkyl, optionally substituted $(C_1$-$C_5)$heteroalkyl, optionally substituted $(C_1-C_6)$alkenyl, optionally substituted $(C_1-C_5)$heteroalkenyl, optionally substituted $(C_1-C_6)$alkynyl, and optionally substituted $(C_1-C_5)$heteroalkynyl.

In a particular embodiment, a MOF of the disclosure comprises one or more cores comprising one or more linking moieties of structural Formula I(a):

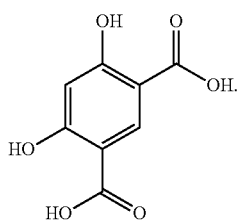

I(a)

A solvent-free Kolbe-Schmitt reaction to produce $H_4$ (m-dobdc) using only resorcinol, $KHCO_3$, and $CO_2$ is efficient and inexpensive. The disclosure demonstrates the superior $H_2$ storage properties of $M_2$ (m-dobdc) and, through the use of neutron diffraction, infrared spectroscopy, and DFT calculations, provide a careful comparison of the structural differences between $M_2$ (dobdc) and $M_2$ (m-dobdc) that lead to this stronger $H_2$ binding. Based on these results, it is expected that $M_2$ (m-dobdc) will have similar or improved adsorption properties for a variety of other gases as compared with $M_2$ (dobdc). Furthermore, the high density of exposed metal cation sites that are more highly charged than sites in other comparable materials can be used for further applications.

The disclosure provides for the preparation of the MOF of the disclosure using highly ordered repeating $M_2$ (m-dobdc) based cores. Scheme I presents a generalized scheme for forming one or more cores of the disclosure by coordinating one or more linking clusters of a linking moiety with a metal ion disclosed herein.

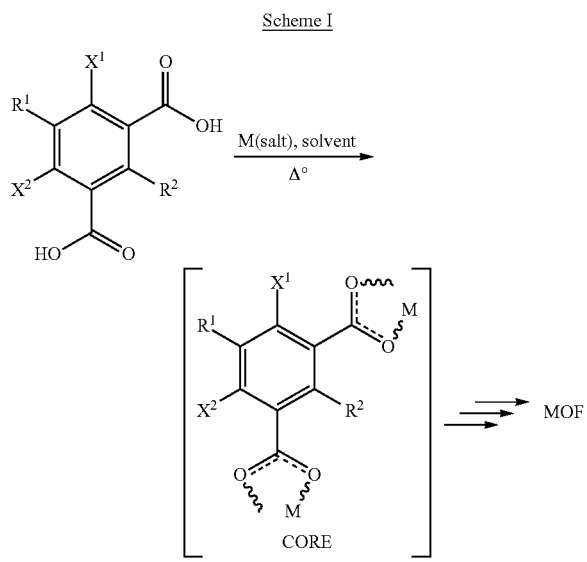

Scheme I

A linking moiety 1 coordinates with a metal ion of a metal containing salt under solvothermal reaction conditions to afford a MOF of the disclosure.

The disclosure further provides that a synthesized MOF disclosed herein may be reacted with a post framework reactant. A post framework reactant adds at least one effect to a MOF of the disclosure including, but not limited to, modulating the gas storage ability of the MOF; modulating the sorption properties of the MOF; modulating the pore size of the MOF; modulating the catalytic activity of the MOF; modulating the conductivity of the MOF; and modulating the sensitivity of the MOF to the presence of an analyte of interest.

The MOFs disclosed herein include a plurality of pores, which can be used for gas adsorption. In one variation, the plurality of pores has a unimodal size distribution. In another variation, the plurality of pores have a multimodal (e.g., bimodal) size distribution.

In a particular embodiment of the disclosure, a gas storage or separation material comprises a MOF disclosed herein. Advantageously, the MOF includes one or more sites for storing and/or separating gas molecules. Suitable examples of such gases include, but are not limited to, the gases comprising a component selected from ammonia, argon, carbon dioxide, carbon monoxide, hydrogen, methane, and combinations thereof. In a particularly useful variation the gas storage material is a hydrogen storage material that is used to store hydrogen $(H_2)$.

The disclosure provides an apparatus and method for separating one or more components from a multi-component gas using a separation system having a feed side and an effluent side separated by a MOF of the disclosure. The MOF may comprise a column separation format. For example, the methods and compositions of the disclosure can be used to separate saturated vs. unsaturated small hydrocarbons (ethane vs. ethylene vs. acetylene, propane vs. propylene, etc.), as well as separations, such as $CO_2$ from a mixture of gases (for applications like removing $CO_2$ from the flue gas in power plants). Other examples include separating $CO_2/H_2$, $CO_2/O_2$, $CO_2/N_2$, methane/ethane, $H_2/D_2$ and others.

In another embodiment, a gas storage material comprising a MOF of disclosure is provided herein. Suitable examples of such gases include, but are not limited to, the gases comprising ammonia, argon, carbon dioxide, carbon monoxide, hydrogen, methane, and combinations thereof. In particularly useful variation, the gas binding material is a $H_2$ binding material that may be used to separate $H_2$ from a gaseous mixture.

In a particular embodiment, one or more MOFs disclosed herein are part of a device. In another embodiment, a gas separation device comprises one or more MOFs of the disclosure. In a further embodiment, a gas separation device used to separate one or more component gases from a multi-component gas mixture comprises one or more MOFs disclosed herein. In a certain embodiment, a gas separation device used to separate one or more gases with high electron density from gas mixture comprises one or more MOFs of the disclosure. In a further embodiment, a gas separation device used to separate one or more gases with high electron density from one or more gases with low electron density comprises one or more MOFs of the disclosure.

In a particular embodiment of the disclosure, a gas storage material comprises one more MOFs disclosed herein. In a particularly useful variation a gas storage material is a hydrogen storage material that is used to store hydrogen $(H_2)$.

In another embodiment, one or more MOFs disclosed herein can be used to separate and/or store one or more gases selected from the group comprising carbon monoxide, carbon dioxide, hydrogen sulfide, hydrogen, carbonyl sulfide, carbon disulfide, and mercaptans.

In an embodiment, one or more MOFs disclosed herein can be used to separate and/or store hydrogen.

One or more MOFs of the disclosure can also comprise part of a gas separation and/or a gas storage device. These devices for gas separation and/or gas storage can be used for industrial or nonindustrial purposes, or a combination thereof. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In a particular embodiment, gas separation and/or gas storage devices comprising one or more MOFs of the disclosure can be used to purify fuel gas streams, air, flue-gas emissions, and/or waste emissions from combustion engines. In another embodiment, one or more MOFs disclosed herein can comprise gas separation and/or gas storage devices designed to remove and/or store greenhouse gases, such as carbon dioxide, ozone, nitrous oxide, and fluorocarbons. In a certain embodiment, one or more MOFs disclosed herein can comprise gas separation and/or gas storage devices designed to remove and/or store $H_2$ resulting from steam reforming, electrolysis, and thermolysis processes.

The following examples are intended to illustrate but not limit the disclosure. While they are typical of those that might be used, other procedures known to those skilled in the art may alternatively be used.

EXAMPLES

Materials:

Methanol (MeOH) was purchased from commercial vendors, further dried over molecular sieves and deoxygenated by purging with $N_2$. All other reagents were purchased from commercial vendors and used without further purification, unless otherwise noted. The $H_4$ (m-dobdc) ligand was synthesized according to Li et al. (*Chem. Lett.* 15:1039 (2005)).

General Procedure for the Synthesis of $M_2$ (m-dobdc).

To 80 mL of a mixed solvent (x % MeOH by volume in dimethylformamide (DMF), where for Mn, x=15; Fe, x=15; Co, x=50; Ni, x=35) was added $H_4$ (m-dobdc) (240 mg, 1.2 mmol) and anhydrous $MCl_2$ (3.0 mmol) in a nitrogen-filled glove box for M=Mn, Fe and in air for M=Co, Ni. The solution was dispensed into 8×20 mL scintillation vials, which were each sealed with a PTFE-lined cap and heated at 120° C. for 18 h. $Mg_2$ (m-dobdc) was synthesized in air in a round-bottom flask by adding 300 mg of $Mg(NO_3)_2 \cdot 6H_2O$ and 93 mg of $H_4$ (m-dobdc) to 14 mL MeOH in 31 mL DMF and stirring at 120° C. for 8 h. The resulting solid for each sample was submerged in DMF (20 mL), and heated at 70° C. for 24 h. The DMF was decanted and replaced with MeOH (20 mL). The suspension was heated at 70° C. for 4 days, during which the MeOH was replaced every 24 h. The material was activated by heating it at 150° C. under dynamic vacuum on a schlenk line for 12 h, followed by further activation of a small amount of the sample by heating the solid under dynamic vacuum (<10 μbar) at 180° C. for 24 h at a ramp rate of 0.5° C./min. It should be noted that larger scale syntheses of $Co_2$ (m-dobdc) and $Ni_2$ (m-dobdc) were also accomplished by stirring at in a round-bottom flask equipped with a reflux condenser at a concentration of 5.04 mmol $H_4$ (m-dobdc) and 12.6 mmol $MCl_2$ (M=Co, Ni) in 480 mL solvent. Times and temperatures were identical to the small-scale synthesis, but 100 mL of solvent was used for each exchange.

$Mn_2$ (m-dobdc).

Synthesis yielded a pink solid that remained pink upon evacuation. IR (neat): 1602 (s), 1547 (s), 1486 (m), 1454 (m), 1387 (s), 1338 (m), 1284 (s), 1172 (s), 1088 (w), 884 (w), 866 (w), 729 (m), 659 (w), 626 (s); Anal. Calcd for $Mn_2C_8H_2O_6$: C, 31.61; H, 0.66. Found: C, 31.68; H, 0.74.

$Fe_2$ (m-dobdc).

Synthesis yielded a beige powder that remained beige upon evacuation. IR (neat): 1652 (w), 1594 (s), 1536 (s), 1452 (s), 1378 (s), 1283 (s), 1173 (m), 1084 (w), 886 (w), 857 (w), 785 (m), 728 (w), 692 (s); Anal. Calcd for $C_8H_2Fe_2O_6$: C, 31.42; H, 0.66; N, 0.00. Found: C, 31.77; H, 1.11; N, 1.28.

$Co_2$ (m-dobdc).

Synthesis yielded a pink solid that turned deep purple upon evacuation. IR (neat): 1600 (s), 1555 (s), 1484 (m), 1451 (m), 1390 (s), 1345 (w), 1284 (s), 1167 (s), 1088 (w), 886 (w), 869 (w), 736 (m), 629 (s); Anal. Calcd for $C_8H_2Co_2O_6$: C, 30.80; H, 0.65. Found: C, 31.60; H, 0.68.

$Ni_2$ (m-dobdc).

Synthesis yielded a green solid that turned a dark yellow-brown upon evacuation. IR (neat): 1600 (m), 1555 (s) 1489 (w), 1449 (m), 1381 (s), 1342 (m), 1285 (s), 1168 (s), 1088 (w), 1012 (w), 871 (w), 741 (m), 631 (m); Anal. Calcd for $C_8H_2Ni_2O_6$: C, 30.85; H, 0.65. Found: C, 31.26; H, 0.60.

Structural Solution Details:

The structure solution for $Co_2$ (m-dobdc) was completed from both neutron and X-ray diffraction data. The X-ray powder pattern for $Co_2$ (m-dobdc) indexed to R3 with lattice parameters of approximately a=25.89 Å and c=6.76 Å using the GSASII software program according to Toby et al. (*J. Appl. Cryst.* 46:544-549 (2013)). The FOX crystallographic software program was used to perform ab initio structure solution by simulated annealing algorithms from the powder X-ray data using the indexed lattice constants and space group and inputting stoichiometric quantities of metal ions and m-dobdc ligand into the unit cell according to Favre-Nicolin et al. (*J. Appl. Cryst.* 35:734-743 (2002)). The m-dobdc ligand was fixed as a rigid body with the carboxyl group coplanar with the benzene ring. Initial attempts at solving the structure by simulated annealing confined in the R3 space group were unsuccessful, however, after consideration of how the dobdc ligand has a rotoinversion axis (R-3) versus the potential for a mirror plane in the m-dobdc, the space group was amended to R3m. Simulated annealing of the X-ray data resulted in a general connectivity resembling hexagonal channels with cobalt ions in the vertices at slightly exaggerated distances and angles from reality.

Figure 4:
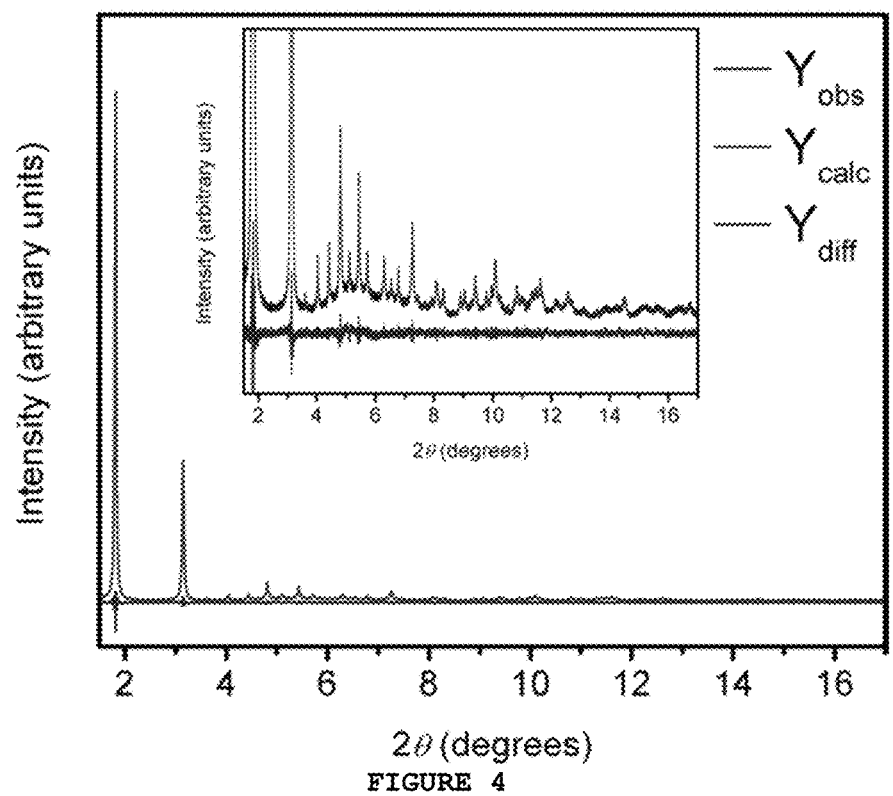
FIG. 4 presents X-ray powder diffraction pattern (wavelength=0.413713 Å) of $Fe_2$ (m-dobdc) ($Y_{obs}$ top line) with calculated diffraction pattern (($Y_{calc}$; substantially overlaps with $Y_{obs}$)) from Le Bail refinement and difference (bottom line). Unit cell parameters: a axis, 26.0893(6) Å; c axis, 6.8740(2) Å.
Figure 5:
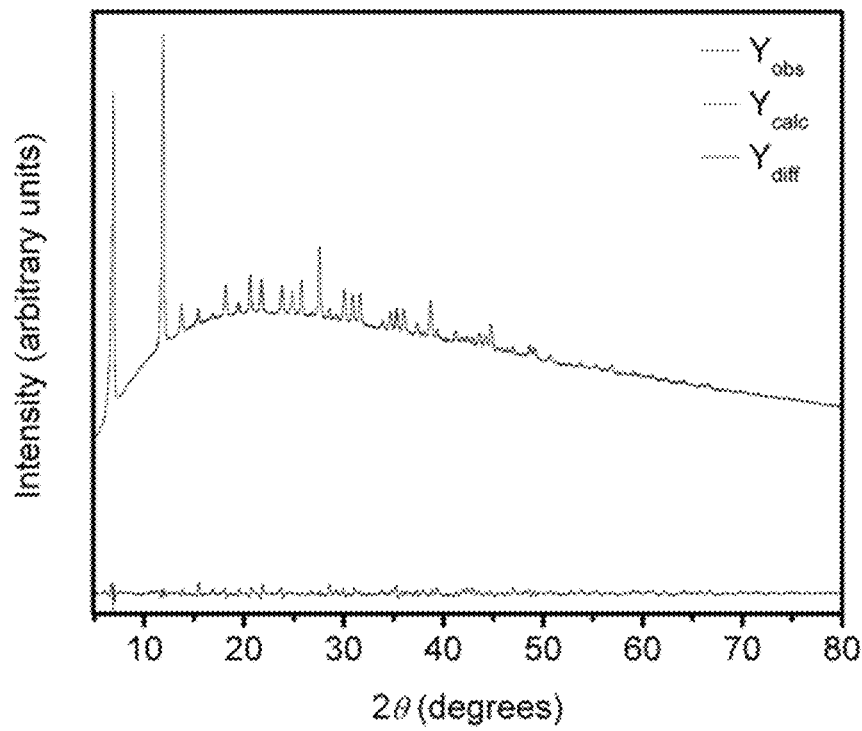
FIG. 5 presents a powder X-ray diffraction pattern of $Co_2$ (m-dobdc) ($Y_{obs}$ top line) with calculated diffraction pattern ($Y_{calc}$; substantially overlaps with $Y_{obs}$) from Le Bail refinement with difference (bottom). Unit cell parameters: a axis, 26.21(2) Å; c axis, 6.95(1) Å; V=4132(6) Å$^3$.
Figure 6:
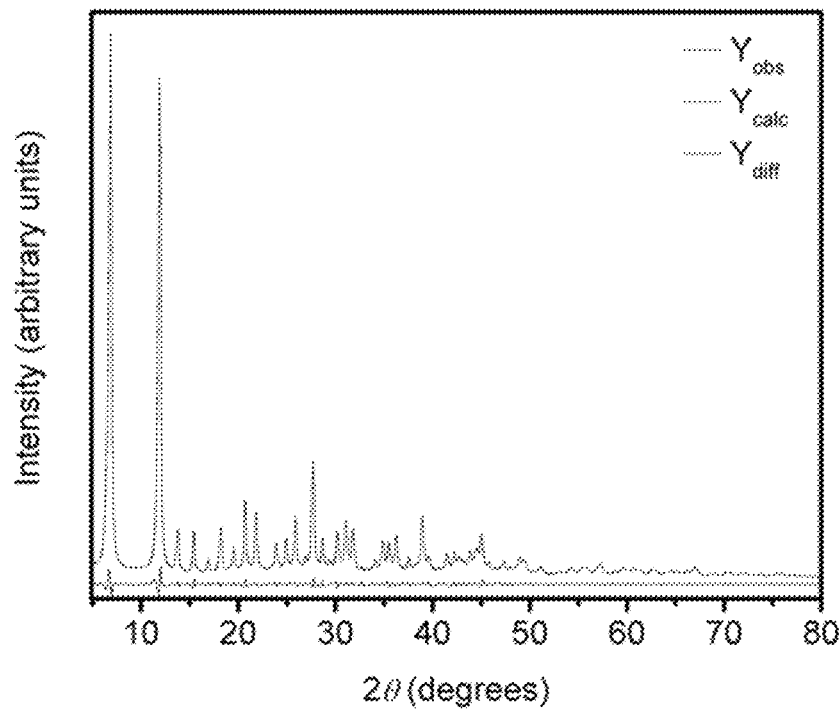
FIG. 6 presents a powder X-ray diffraction pattern of $Ni_2$ (m-dobdc) ($Y_{obs}$ top line) with calculated diffraction pattern ($Y_{calc}$; substantially overlaps with $Y_{obs}$) from Le Bail refinement with difference (bottom). Unit cell parameters: a axis, 25.936(2) Å; c axis, 6.79(1) Å; V=3957 (1) Å$^3$.

Unit cells were determined for all $M_2$ (m-dobdc) frameworks at room temperature by performing an overnight scan in the 2θ range of 4-65° with 0.02° steps using a Bruker AXS D8 Advance diffractometer equipped with CuKα radiation (λ=1.5418 Å), a Lynxeye linear position-sensitive detector, and mounting the following optics: Göbel mirror, fixed divergence slit (0.6 mm), receiving slit (3 mm), and secondary beam Soller slits (2.5°). The generator was set at 40 kV and 40 mA. A standard peak search, followed by indexing via the Single Value Decomposition approach from Coelho (*Appl. Cryst.* 36:86-95 (2003)), as implemented in TOPAS-Academic, allowed the determination of approximate unit cell dimensions. Precise unit cell dimensions were determined by performing a structureless Le Bail refinement in TOPAS-Academic. Note that while the peak positions of the $Fe_2$ (m-dobdc) powder pattern match those of the other $M_2$ (m-dobdc) analogues (FIG. 4), the quality of the diffraction data on this air-sensitive material were not of high enough quality to determine precise unit cell dimensions. The cell parameters for $Mg_2$ (m-dobdc), $Mn_2$ (m-dobdc), $Co_2$ (m-dobdc), and $Ni_2$ (m-dobdc) found from X-ray powder diffraction are presented in TABLE 1.

TABLE 1

Cell parameters for $Mn_2$(m-dobdc), $Fe_2$(m-dobdc), $Co_2$(m-dobdc), and $Ni_2$(m-dobdc) found from X-ray powder diffraction.

| | a axis (Å) | c axis (Å) | Volume (Å$^3$) |
|---|---|---|---|
| $Mn_2$(m-dobdc) | 25.8225 (6) | 6.71 (1) | 3874 (1) |
| $Co_2$(m-dobdc) | 26.21 (2) | 6.95 (1) | 4132 (6) |
| $Ni_2$(m-dobdc) | 25.936 (2) | 6.79 (1) | 3957 (1) |
| $Mg_2$(m-dobdc) | 25.893 (2) | 6.81 (1) | 3955 (1) |
| $Fe_2$(m-dobdc) | 26.0893 (6) | 6.8740 (2) | 4051.9 (2) |

The overall connectivity and ligand orientation for $Co_2$ (m-dobdc) was determined from a full Rietveld analysis of the neutron and X-ray diffraction data as implemented in EXPGUI/GSAS. The structure solution from $Co_2$ (m-dobdc) was used as the basis for the solution of the $Ni_2$ (m-dobdc) NPD data by Rietveld refinement. For the gas dosed refinements, the starting model for the activated $Co_2$ (dobdc) framework was taken from the data on the bare material presented in Queen et al. (*Dalton Trans.* 41:4180-7 (2012)) and Sumida et al. (*Chem. Commun.* 47:1157-59 (2011)). Fourier difference methods were employed to locate the adsorbed $D_2$ molecules in both $Co_2$ (dobdc) and $Co_2$ (m-dobdc). A dose of 0.75 $D_2$ per $Co^{2+}$ was chosen to provide clarity in the structure model for the active site in eliminating potential $D_2$ intermolecular interactions based on previous knowledge of adsorption in $M_2$ (dobdc). A secondary dose of 2.25 $D_2$ per $Co^{2+}$ was chosen for direct comparison with the results in Queen et al. and Sumida et al. In all instances, the atomic positions and isotropic atomic displacement parameters (ADPs) left free to refine during the analysis process after first accounting for a significant portion of the excess $D_2$ scattering density via Fourier methods. In the refinement of the 2.0 and 3.0 per $Co^{2+}$ data in $Co_2$ (m-dobdc), the primary deuterium site occupancy (D1) was fixed at fully occupied 1.0 $D_2$ per $Co^{2+}$ to better model the data. Refined values for $D_2$ occupancies are presented with standard deviations for the 0.75, 1.25, 1.5, 1.75, and 2.25 $D_2$ per $Co^{2+}$ results. For the 3.0 $D_2$ per $Ni^{2+}$ data, the first three deuterium sites were fixed at fully occupied 1.0 $D_2$ at each site to better model the data.

Physical Measurements.

Thermogravimetric analyses were carried out at a ramp rate of 2° C./min under a 25 mL/min $N_2$ flow with a TA Instruments TGA Q5000. Infrared spectra were collected on a Perkin-Elmer Advance Spectrum 400 FTIR spectrometer equipped with a Pike attenuated total reflectance (ATR) accessory. Diffraction data were collected with 0.02° steps using a Bruker AXS D8 Advance diffractometer equipped with Cu-Kα radiation ($\lambda$=1.5418 Å), a Göbel mirror, a Lynxeye linear position-sensitive director, and mounting the following optics: fixed divergence slit (0.6 mm), receiving slit (3 mm), and secondary beam Soller slits (2.5°). The generator was set at 40 kV and 40 mA. Samples were either loaded on zero background sample holders or packed into air-free capillaries in a dinitrogen glove box and mounted using a capillary stage. Elemental analyses were obtained from the Microanalytical Laboratory of the University of California, Berkeley.

Low-Pressure Gas Adsorption Measurements.

Gas adsorption isotherms for pressures in the range 0-1.2 bar were measured using a volumetric method using either a Micromeritics ASAP2020 or ASAP2420 instrument. Samples were transferred under a dinitrogen atmosphere to preweighed analysis tubes, and then capped with a Transeal. The samples were evacuated at elevated temperature until the outgas rate was less than 1 μbar/min, at which point the tube was weighed to determine the mass of the activated sample, which was typically 50-200 mg. The tube was transferred to the analysis port of the instrument and the outgas rate was again checked to ensure that it was less than 1 pbar/min. UHP-grade (99.999% purity) $N_2$, $H_2$, and He were used for all adsorption measurements. For all isotherms, warm and cold free spaces were measured using He; $N_2$ and $H_2$ isotherms at 77 K and 87 K were measured in liquid nitrogen and liquid argon baths, respectively. Oil-free vacuum pumps and oil-free pressure regulators were used for all measurements. Brunauer-Emett-Teller (BET) and Langmuir surface areas were determined from $N_2$ adsorption data at 77 K using Micromeritics software.

Neutron Diffraction and APS X-ray Diffraction.

Neutron powder diffraction (NPD) experiments were carried out on 0.8358, 0.9567, and 0.9702 g activated $Co_2$ (m-dobdc), $Ni_2$ (m-dobdc), and $Co_2$ (dobdc) samples respectively, using the high-resolution neutron powder diffractometer, BT1, at the National Institute of Standards and Technology Center for Neutron Research (NCNR). The samples were placed in a He purged glove box and loaded into a vanadium sample can equipped with a valve for gas loading, and sealed using an indium O-ring. NPD data were collected using a Ge(311) monochromator with an in-pile 60' collimator corresponding to a wavelength of 2.078 Å. The samples were loaded onto bottom-loading closed cycle refrigerators and initial data collected on the activated $Co_2$ (m-dobdc) and $Ni_2$ (m-dobdc) frameworks at 10 K. As part of the initial structure solution, X-ray diffraction (XRD) measurements were carried out on 12.8 mg of $Co_2$ (m-dobdc) at the Advanced Photon Source (APS) on the 17-BM materials diffractometer ($\lambda$=0.7291 Å) at 298 K. The activated $Co_2$ (m-dobdc) sample was transferred into quartz capillary in a He purged glovebox and wax sealed for the X-ray measurements. For comparison of the $D_2$ structural dependence on ligand connectivity, $Co_2$ (dobdc) and $Co_2$ (m-dobdc) were each individually connected to a gas manifold of known volume and exposed to a known dose, approximately 0.75 and 2.25 $D_2$ per $Co^{2+}$, at 100 K (refined composition given in TABLES 4-6 and 11). Both samples were slow cooled from 100 K to 10 K to ensure full equilibration and complete adsorption, as evidenced by a zero pressure reading on the barometer by 25 K, for data collection. Further $D_2$ structural data was collected on $Co_2$ (m-dobdc) and $Ni_2$ (m-dobdc) as a function of dose with final loadings of 0.75, 1.25, 1.5, 1.75, 2.0, 2.25, and 3.0 $D_2$ per cobalt and 1.0, 2.0, and 3.0 $D_2$ per nickel with the refined composition given in the following Tables (TABLE 4 and 7-12 (Co) and TABLE 14-16 (Ni)):

TABLE 2

Atomic parameters from Rietveld refinement of desolvated Co$_2$(m-dobdc) at 10 K [NCNR, BT1], R3m, a = 25.873(2) Å, c = 6.7677(9) Å, V = 3923.6(6) Å$^3$. Values in parentheses indicate one standard deviation in the refined value. Goodness-of-fit parameters: $\chi^2$ = 0.87; wRp = 5.42%; Rp = 4.32%. Refined composition: Co$_{18}$H$_{18}$C$_{72}$O$_{54}$.

| Atom | X | Y | Z | Occupancy | U$_{(ISO)}$ (Å$^2$) | Multiplicity |
|---|---|---|---|---|---|---|
| C1 | 0.658(1) | 0.878(1) | 0.837(4) | 1 | 0.044(9) | 18 |
| C2 | 0.665(1) | 0.8327(7) | 0.744(5) | 1 | 0.02(1) | 9 |
| C6 | 0.639(1) | 0.8661(8) | 0.040(4) | 1 | 0.015(6) | 18 |
| C11 | 0.6322(8) | 0.9088(8) | 0.163(3) | 1 | 0.013(5) | 18 |
| Co1 | 0.328(3) | 0.376(2) | 0.556(8) | 1 | 0.02(2) | 18 |
| H7 | 0.680(3) | 0.840(1) | 0.59(1) | 1 | 0.04(2) | 9 |
| O9 | 0.670(1) | 0.926(1) | 0.748(4) | 1 | 0.031(9) | 18 |
| O12 | 0.652(1) | 0.962(1) | 0.096(3) | 1 | 0.019(7) | 18 |
| O15 | 0.610(1) | 0.891(1) | 0.334(4) | 1 | 0.034(7) | 18 |
| C2m | 0.628(1) | 0.8141(6) | 0.125(4) | 1 | 0.026(9) | 9 |
| H7m | 0.617(2) | 0.809(1) | 0.282(8) | 1 | 0.03(1) | 9 |

TABLE 3

Atomic parameters from Rietveld refinement of desolvated Co$_2$(m-dobdc) at 298 K [APS, 17-BM-B], R3m, a = 25.8902(7) Å, c = 6.7905(3) Å, V = 3941.9(2) Å$^3$. Values in parentheses indicate one standard deviation in the refined value. Goodness-of-fit parameters: $\chi^2$ = 4.505; wRp = 3.71%; Rp = 2.94%. Refined composition: Co$_{18}$H$_{18}$C$_{72}$O$_{54}$.

| Atom | X | Y | Z | Occupancy | U$_{(ISO)}$ (Å$^2$) | Multiplicity |
|---|---|---|---|---|---|---|
| C1 | 0.658(2) | 0.877(2) | 0.837(9) | 1 | 0.17(2) | 18 |
| C2 | 0.669(3) | 0.835(2) | 0.74(1) | 1 | 0.11(2) | 9 |
| C6 | 0.639(1) | 0.866(1) | 0.036(7) | 1 | 0.026(8) | 18 |
| C11 | 0.632(1) | 0.908(1) | 0.163(8) | 1 | 0.022(9) | 18 |
| Co1 | 0.3276(3) | 0.3751(2) | 0.557(6) | 1 | 0.0213(6) | 18 |
| H7 | 0.69(1) | 0.845(6) | 0.58(4) | 1 | 0.2(1) | 9 |
| O9 | 0.6704(9) | 0.9263(6) | 0.747(8) | 1 | 0.022(5) | 18 |
| O12 | 0.6516(7) | 0.9614(8) | 0.098(7) | 1 | 0.067(8) | 18 |
| O15 | 0.6103(6) | 0.8919(7) | 0.339(6) | 1 | 0.052(7) | 18 |
| C2m | 0.627(2) | 0.813(1) | 0.127(7) | 1 | 0.09(2) | 9 |
| H7m | 0.63(1) | 0.813(5) | 0.29(4) | 1 | 0.06(9) | 9 |

TABLE 4

Atomic parameters from Rietveld refinement of Co$_2$(m-dobdc) dosed with 0.75 D$_2$ per Co$^{2+}$ at 10 K [NCNR, BT1], R3m, a = 25.842(2) Å, c = 6.7810(7) Å, V = 3921.7(5) Å$^3$. Values in parentheses indicate one standard deviation in the refined value. Goodness-of-fit parameters: $\chi^2$ = 0.83; wRp = 4.98%; Rp = 3.91%. Refined composition: Co$_{18}$H$_{18}$C$_{72}$O$_{54}$D$_{30.466}$.

| Atom | X | Y | Z | Occupancy | U$_{(ISO)}$ (Å$^2$) | Multiplicity |
|---|---|---|---|---|---|---|
| C1 | 0.6573(8) | 0.8763(8) | 0.838(3) | 1 | 0.018(5) | 18 |
| C2 | 0.665(1) | 0.8323(5) | 0.747(4) | 1 | 0.013(8) | 9 |
| C6 | 0.6399(7) | 0.8669(7) | 0.045(3) | 1 | 0.015(5) | 18 |
| C11 | 0.6321(6) | 0.9089(6) | 0.164(2) | 1 | 0.004(3) | 18 |
| Ni1 | 0.330(2) | 0.376(2) | 0.559(6) | 1 | 0.001(9) | 18 |
| H7 | 0.678(3) | 0.839(1) | 0.59(1) | 1 | 0.06(2) | 9 |
| O9 | 0.6700(8) | 0.9255(7) | 0.748(3) | 1 | 0.010(5) | 18 |
| O12 | 0.6497(9) | 0.9617(9) | 0.090(3) | 1 | 0.021(7) | 18 |
| O15 | 0.6084(8) | 0.8903(8) | 0.330(3) | 1 | 0.011(4) | 18 |
| C2m | 0.629(1) | 0.8142(6) | 0.125(4) | 1 | 0.026(8) | 9 |
| H7m | 0.616(2) | 0.808(1) | 0.285(8) | 1 | 0.04(1) | 9 |
| D1 | 0.2042(6) | 0.2155(6) | 0.018(2) | 1.69(5) | 0.090(6) | 18 |

TABLE 5

Atomic parameters from Rietveld refinement of $Co_2(dobdc)$ dosed with 0.75 $D_2$ per $Co^{2+}$ at 10 K [NCNR, BT1], R-3, a = 25.871(1) Å, c = 6.8687(4) Å, V = 3981.3(3) Å$^3$. Values in parentheses indicate one standard deviation in the refined value. Goodness-of-fit parameters: $\chi_\nu^2$ = 1.356; wRp = 2.79%; Rp = 2.29%. Refined composition: $Co_{18}H_{18}C_{72}O_{54}D_{28.61}$.

| Atom | X | Y | Z | Occupancy | $U_{(ISO)}$ (Å$^2$) | Multiplicity |
|---|---|---|---|---|---|---|
| Co | 0.386(1) | 0.355(1) | 0.134(3) | 1 | 0.004(6) | 18 |
| O1 | 0.3229(5) | 0.2946(5) | 0.372(2) | 1 | 0.017(3) | 18 |
| O2 | 0.3040(5) | 0.2292(5) | 0.601(1) | 1 | 0.005(3) | 18 |
| O3 | 0.3577(5) | 0.2742(5) | 0.002(2) | 1 | 0.005(3) | 18 |
| C1 | 0.3147(5) | 0.2463(5) | 0.428(1) | 1 | 0.030(3) | 18 |
| C2 | 0.3300(4) | 0.2086(4) | 0.281(1) | 1 | 0.018(3) | 18 |
| C3 | 0.3491(4) | 0.2278(4) | 0.090(1) | 1 | 0.010(3) | 18 |
| C4 | 0.3525(4) | 0.1839(5) | −0.035(1) | 1 | 0.004(3) | 18 |
| H | 0.3601(7) | 0.1925(6) | −0.159(3) | 1 | 0.001(4) | 18 |
| D1 | 0.4659(4) | 0.3498(4) | 0.265(1) | 1.59(3) | 0.089(5) | 18 |

TABLE 6

Atomic parameters from Rietveld refinement of $Co_2(dobdc)$ dosed with 2.25 $D_2$ per $Co^{2+}$ at 10 K [NCNR, BT1], R-3, a = 25.878(1) Å, c = 6.8820(3) Å, V = 3991.3(3) Å$^3$. Values in parentheses indicate one standard deviation in the refined value. Goodness-of-fit parameters: $\chi_\nu^2$ = 1.459; wRp = 2.81%; Rp = 2.34%. Refined composition: $Co_{18}H_{18}C_{72}O_{54}D_{88.56}$.

| Atom | X | Y | Z | Occupancy | $U_{(ISO)}$ (Å$^2$) | Multiplicity |
|---|---|---|---|---|---|---|
| Co | 0.381(1) | 0.351(1) | 0.132(4) | 1 | 0.004(7) | 18 |
| O1 | 0.3246(6) | 0.2940(6) | 0.365(2) | 1 | 0.009(4) | 18 |
| O2 | 0.3006(6) | 0.2281(6) | 0.599(2) | 1 | 0.009(3) | 18 |
| O3 | 0.3570(6) | 0.2745(7) | −0.003(2) | 1 | 0.012(4) | 18 |
| C1 | 0.3143(6) | 0.2450(6) | 0.426(1) | 1 | 0.013(3) | 18 |
| C2 | 0.3296(5) | 0.2087(5) | 0.287(2) | 1 | 0.010(3) | 18 |
| C3 | 0.3463(5) | 0.2251(6) | 0.088(2) | 1 | 0.018(4) | 18 |
| C4 | 0.3501(5) | 0.1811(6) | −0.029(2) | 1 | 0.008(4) | 18 |
| H | 0.3633(8) | 0.1945(7) | −0.166(4) | 1 | 0.010(6) | 18 |
| D1 | 0.4642(5) | 0.3493(4) | 0.250(2) | 1.60(3) | 0.065(4) | 18 |
| D2 | 0.4587(5) | 0.2999(4) | 0.673(2) | 1.92(5) | 0.130(7) | 18 |
| D3 | 0.2400(8) | 0.4877(7) | 0.852(3) | 1.40(3) | 0.15(1) | 18 |

TABLE 7

Atomic parameters from Rietveld refinement of $Co_2$(m-dobdc) dosed with 1.25 $D_2$ per $Co^{2+}$ at 10 K [NCNR, BT1], R3m, a = 25.872(1) Å, c = 6.7881(5) Å, V = 3928.8(5) Å$^3$. Values in parentheses indicate one standard deviation in the refined value. Goodness-of-fit parameters: $\chi_\nu^2$ = 1.123; wRp = 3.45%; Rp = 2.80%. Refined composition: $Co_{18}H_{18}C_{72}O_{54}D_{42.66}$.

| Atom | X | Y | Z | Occupancy | $U_{(ISO)}$ (Å$^2$) | Multiplicity |
|---|---|---|---|---|---|---|
| C1 | 0.6567(6) | 0.8752(6) | 0.837(2) | 1 | 0.010(4) | 18 |
| C2 | 0.6664(9) | 0.8332(4) | 0.753(4) | 1 | 0.010(6) | 9 |
| C6 | 0.6414(6) | 0.8682(6) | 0.040(2) | 1 | 0.014(4) | 18 |
| C11 | 0.6337(5) | 0.9093(5) | 0.160(2) | 1 | 0.008(3) | 18 |
| Co2 | 0.328(2) | 0.373(1) | 0.570(4) | 1 | 0.002(8) | 18 |
| H7 | 0.674(2) | 0.837(1) | 0.608(7) | 1 | 0.05(2) | 9 |
| O9 | 0.6723(6) | 0.9273(6) | 0.743(2) | 1 | 0.005(4) | 18 |
| O12 | 0.6511(7) | 0.9636(7) | 0.086(2) | 1 | 0.018(5) | 18 |
| O15 | 0.6103(7) | 0.8947(6) | 0.338(2) | 1 | 0.010(4) | 18 |
| C2m | 0.6275(8) | 0.8137(4) | 0.136(3) | 1 | 0.012(6) | 9 |
| H7m | 0.618(2) | 0.8091(9) | 0.275(7) | 1 | 0.04(1) | 9 |
| D1 | 0.2044(4) | 0.2145(5) | 0.019(1) | 1.87(4) | 0.071(5) | 18 |
| D2 | 0.791(2) | 0.952(2) | 0.414(6) | 0.50(4) | 0.15(3) | 18 |

TABLE 8

Atomic parameters from Rietveld refinement of $Co_2$(m-dobdc) dosed with 1.50 $D_2$ per $Co^{2+}$ at 10 K [NCNR, BT1], R3m, a = 25.852(2) Å, c = 6.7898(7) Å, V = 3929.9(6) Å$^3$. Values in parentheses indicate one standard deviation in the refined value. Goodness-of-fit parameters: $\chi^2$ = 0.889; wRp = 5.11%; Rp = 4.06%. Refined composition: $Co_{18}H_{18}C_{72}O_{54}D_{48.78}$.

| Atom | X | Y | Z | Occupancy | $U_{(ISO)}$ (Å$^2$) | Multiplicity |
|---|---|---|---|---|---|---|
| C1  | 0.6571(9) | 0.8745(9) | 0.838(3)  | 1       | 0.014(6)  | 18 |
| C2  | 0.664(1)  | 0.8322(6) | 0.754(5)  | 1       | 0.012(9)  | 9  |
| C6  | 0.6413(9) | 0.8676(8) | 0.044(3)  | 1       | 0.018(6)  | 18 |
| C11 | 0.6324(7) | 0.9091(8) | 0.165(3)  | 1       | 0.011(5)  | 18 |
| Co2 | 0.327(2)  | 0.372(2)  | 0.555(7)  | 1       | 0.004(13) | 18 |
| H7  | 0.677(3)  | 0.839(1)  | 0.59(1)   | 1       | 0.06(2)   | 9  |
| O9  | 0.6706(8) | 0.9261(8) | 0.750(4)  | 1       | 0.008(6)  | 18 |
| O12 | 0.652(1)  | 0.964(1)  | 0.091(3)  | 1       | 0.022(6)  | 18 |
| O15 | 0.609(1)  | 0.8924(9) | 0.336(3)  | 1       | 0.013(5)  | 18 |
| C2m | 0.628(1)  | 0.8138(6) | 0.133(4)  | 1       | 0.018(9)  | 9  |
| H7m | 0.615(3)  | 0.808(1)  | 0.273(9)  | 1       | 0.03(2)   | 9  |
| D1  | 0.2062(6) | 0.2169(7) | 0.018(2)  | 2.00(7) | 0.096(8)  | 18 |
| D2  | 0.778(2)  | 0.946(2)  | 0.440(7)  | 0.71(5) | 0.12(2)   | 18 |

TABLE 9

Atomic parameters from Rietveld refinement of $Co_2$(m-dobdc) dosed with 1.75 $D_2$ per $Co^{2+}$ at 10 K [NCNR, BT1], R3m, a = 25.883(1) Å, c = 6.8030(4) Å, V = 3946.8(3) Å$^3$. Values in parentheses indicate one standard deviation in the refined value. Goodness-of-fit parameters: $\chi^2$ = 1.351; wRp = 3.01%; Rp = 2.47%. Refined composition: $Co_{18}H_{18}C_{72}O_{54}D_{62.46}$.

| Atom | X | Y | Z | Occupancy | $U_{(ISO)}$ (Å$^2$) | Multiplicity |
|---|---|---|---|---|---|---|
| C1  | 0.6567(6) | 0.8755(5) | 0.836(2)  | 1       | 0.012(4)  | 18 |
| C2  | 0.6672(8) | 0.8336(4) | 0.746(3)  | 1       | 0.010(5)  | 9  |
| C6  | 0.6414(6) | 0.8680(5) | 0.045(2)  | 1       | 0.015(4)  | 18 |
| C11 | 0.6341(4) | 0.9101(5) | 0.163(2)  | 1       | 0.007(3)  | 18 |
| Co2 | 0.328(1)  | 0.373(1)  | 0.571(4)  | 1       | 0.001(7)  | 18 |
| H7  | 0.678(2)  | 0.8387(9) | 0.599(8)  | 1       | 0.07(2)   | 9  |
| O9  | 0.6732(5) | 0.9279(5) | 0.747(2)  | 1       | 0.008(4)  | 18 |
| O12 | 0.6520(6) | 0.9635(6) | 0.092(2)  | 1       | 0.015(4)  | 18 |
| O15 | 0.6119(6) | 0.8957(6) | 0.336(2)  | 1       | 0.014(4)  | 18 |
| C2m | 0.6287(7) | 0.8143(4) | 0.143(3)  | 1       | 0.009(5)  | 9  |
| H7m | 0.621(2)  | 0.8105(8) | 0.272(6)  | 1       | 0.03(1)   | 9  |
| D1  | 0.2065(4) | 0.2157(4) | 0.006(2)  | 1.76(4) | 0.082(5)  | 18 |
| D2  | 0.7777(8) | 0.9466(6) | 0.426(3)  | 1.27(3) | 0.104(7)  | 18 |
| D3  | 0.575(2)  | 0.149(4)  | 0.47(1)   | 0.9(1)  | 0.8(2)    | 9  |

TABLE 10

Atomic parameters from Rietveld refinement of $Co_2$(m-dobdc) dosed with 2.0 $D_2$ per $Co^{2+}$ at 10 K [NCNR, BT1], R3m, a = 25.881 (2) Å, c = 6.8038(6) Å, V = 3946.7(6) Å$^3$. Values in parentheses indicate one standard deviation in the refined value. Goodness-of-fit parameters: $\chi^2$ = 0.84; wRp = 5.19%; Rp = 4.13%. Refined composition: $Co_{18}H_{18}C_{72}O_{54}D_{67.14}$.

| Atom | X | Y | Z | Occupancy | $U_{(ISO)}$ (Å$^2$) | Multiplicity |
|---|---|---|---|---|---|---|
| C1  | 0.6572(9) | 0.8750(9) | 0.835(4)  | 1 | 0.016(6)  | 18 |
| C2  | 0.666(1)  | 0.8328(6) | 0.749(5)  | 1 | 0.015(8)  | 9  |
| C6  | 0.6414(9) | 0.8681(8) | 0.044(4)  | 1 | 0.017(6)  | 18 |
| C11 | 0.6338(7) | 0.9098(7) | 0.162(3)  | 1 | 0.012(5)  | 18 |
| Co2 | 0.325(2)  | 0.372(2)  | 0.558(7)  | 1 | 0.002(14) | 18 |
| H7  | 0.678(3)  | 0.839(1)  | 0.60(1)   | 1 | 0.07(2)   | 9  |
| O9  | 0.6718(9) | 0.9267(9) | 0.751(4)  | 1 | 0.014(7)  | 18 |
| O12 | 0.6523(9) | 0.964(1)  | 0.093(3)  | 1 | 0.017(7)  | 18 |
| O15 | 0.6107(9) | 0.8939(9) | 0.331(3)  | 1 | 0.018(5)  | 18 |
| C2m | 0.628(1)  | 0.8141(6) | 0.131(5)  | 1 | 0.014(8)  | 9  |
| H7m | 0.616(2)  | 0.808(1)  | 0.280(9)  | 1 | 0.03(2)   | 9  |

TABLE 10-continued

Atomic parameters from Rietveld refinement of $Co_2$(m-dobdc) dosed with 2.0 $D_2$ per $Co^{2+}$ at 10 K [NCNR, BT1], R3m, a = 25.881 (2) Å, c = 6.8038(6) Å, V = 3946.7(6) Å$^3$.
Values in parentheses indicate one standard deviation in the refined value.
Goodness-of-fit parameters: $\chi^2$ = 0.84; wRp = 5.19%;
Rp = 4.13%. Refined composition: $Co_{18}H_{18}C_{72}O_{54}D_{67.14}$.

| Atom | X | Y | Z | Occupancy | $U_{(ISO)}$ (Å$^2$) | Multiplicity |
|---|---|---|---|---|---|---|
| D1 | 0.2076(7) | 0.2162(7) | 0.008(3) | 2.0 | 0.110(7) | 18 |
| D2 | 0.775(1) | 0.9469(9) | 0.426(4) | 1.51(6) | 0.12(1) | 18 |
| D3 | 0.581(3) | 0.163(5) | 0.49(2) | 0.43(8) | 0.19(8) | 9 |

TABLE 11

Atomic parameters from Rietveld refinement of $Co_2$(m-dobdc) dosed with 2.25 $D_2$ per $Co^{2+}$ at 10 K [NCNR, BT1], R3m, a = 25.901(1) Å, c = 6.810 (4) Å, V = 3956.7(4) Å$^3$. Values in parentheses indicate one standard deviation in the refined value.
Goodness-of-fit parameters: $\chi^2$ = 1.149; wRp = 3.32%;
Rp = 2.73%. Refined composition: $Co_{18}H_{18}C_{72}O_{54}D_{80.82}$.

| Atom | X | Y | Z | Occupancy | $U_{(ISO)}$ (Å$^2$) | Multiplicity |
|---|---|---|---|---|---|---|
| C1 | 0.6578(6) | 0.8758(6) | 0.832(3) | 1 | 0.013(4) | 18 |
| C2 | 0.6676(8) | 0.8338(4) | 0.739(4) | 1 | 0.009(5) | 9 |
| C6 | 0.6425(6) | 0.8683(6) | 0.041(3) | 1 | 0.019(4) | 18 |
| C11 | 0.6357(5) | 0.9108(6) | 0.161(2) | 1 | 0.015(4) | 18 |
| Co2 | 0.328(2) | 0.373(1) | 0.565(5) | 1 | 0.003(8) | 18 |
| H7 | 0.676(1) | 0.8380(7) | 0.594(7) | 1 | 0.04(1) | 9 |
| O9 | 0.6747(5) | 0.9287(5) | 0.747(2) | 1 | 0.000(4) | 18 |
| O12 | 0.6538(6) | 0.9638(7) | 0.090(2) | 1 | 0.011(5) | 18 |
| O15 | 0.6130(6) | 0.8968(7) | 0.332(2) | 1 | 0.019(4) | 18 |
| C2m | 0.6295(8) | 0.8147(4) | 0.137(3) | 1 | 0.008(6) | 9 |
| H7m | 0.620(2) | 0.8102(7) | 0.267(7) | 1 | 0.018(9) | 9 |
| D1 | 0.2059(5) | 0.2157(5) | 0.001(2) | 1.82(4) | 0.089(6) | 18 |
| D2 | 0.7756(7) | 0.9478(6) | 0.423(3) | 1.64(3) | 0.104(5) | 18 |
| D3 | 0.576(1) | 0.152(2) | 0.526(6) | 1.05(9) | 0.23(4) | 9 |
| D4 | 0.587(2) | 0.174(5) | 0.16(2) | 1.0(2) | 0.8(2) | 9 |

TABLE 12

Atomic parameters from Rietveld refinement of $Co_2$(m-dobdc) dosed with 3.0 $D_2$ per $Co^{2+}$ at 10 K [NCNR, BT1], R3m, a = 25.892(2) Å, c = 6.8115(6) Å, V = 3954.7(6) Å$^3$. Values in parentheses indicate one standard deviation in the refined value.
Goodness-of-fit parameters: $\chi^2$ = 0.873; wRp = 5.01%;
Rp = 4.00%. Refined composition: $Co_{18}H_{18}C_{72}O_{54}D_{101.34}$.

| Atom | X | Y | Z | Occupancy | $U_{(ISO)}$ (Å$^2$) | Multiplicity |
|---|---|---|---|---|---|---|
| C1 | 0.659(1) | 0.877(1) | 0.837(3) | 1 | 0.018(6) | 18 |
| C2 | 0.667(1) | 0.8335(6) | 0.752(5) | 1 | 0.012(8) | 9 |
| C6 | 0.644(1) | 0.8692(9) | 0.047(3) | 1 | 0.023(6) | 18 |
| C11 | 0.6365(8) | 0.9117(9) | 0.163(3) | 1 | 0.024(6) | 18 |
| Co2 | 0.327(2) | 0.371(1) | 0.564(7) | 1 | 0.001(13) | 18 |
| H7 | 0.678(2) | 0.839(1) | 0.583(9) | 1 | 0.03(2) | 9 |
| O9 | 0.6745(9) | 0.9275(9) | 0.751(3) | 1 | 0.009(6) | 18 |
| O12 | 0.6533(9) | 0.964(1) | 0.092(3) | 1 | 0.015(7) | 18 |
| O15 | 0.614(1) | 0.897(1) | 0.333(3) | 1 | 0.025(6) | 18 |
| C2m | 0.629(1) | 0.8145(6) | 0.131(4) | 1 | 0.011(8) | 9 |
| H7m | 0.615(2) | 0.808(1) | 0.271(8) | 1 | 0.02(2) | 9 |
| D1 | 0.2088(7) | 0.2169(7) | 0.004(2) | 2.0 | 0.093(6) | 18 |
| D2 | 0.7752(8) | 0.9466(9) | 0.429(3) | 1.91(5) | 0.120(8) | 18 |
| D3 | 0.5789(7) | 0.158(1) | 0.525(4) | 2.00(9) | 0.19(2) | 9 |
| D4 | 0.5855(6) | 0.171(1) | 0.045(4) | 1.43(6) | 0.11(2) | 9 |

TABLE 13

Atomic parameters from Rietveld refinement of desolvated Ni$_2$(m-dobdc) at 10 K [NCNR, BT1], R3m, a = 25.797(5) Å, c = 6.729(2) Å, V = 3878.(1) Å$^3$. Values in parentheses indicate one standard deviation in the refined value. Goodness-of-fit parameters: $\chi^2$ = 1.10; wRp = 4.27%; Rp = 3.48%. Refined composition: Ni$_{18}$H$_{18}$C$_{72}$O$_{54}$.

| Atom | X | Y | Z | Occupancy | U$_{(ISO)}$ (Å$^2$) | Multiplicity |
|---|---|---|---|---|---|---|
| C1  | 0.658(2) | 0.878(1) | 0.837(6) | 1 | 0.03(1)  | 18 |
| C2  | 0.666(3) | 0.833(1) | 0.75(1)  | 1 | 0.03(2)  | 9  |
| C6  | 0.639(2) | 0.866(1) | 0.043(6) | 1 | 0.01(1)  | 18 |
| C11 | 0.632(1) | 0.909(1) | 0.166(5) | 1 | 0.011(9) | 18 |
| Ni1 | 0.326(1) | 0.376(1) | 0.555(3) | 1 | 0.020(6) | 18 |
| H7  | 0.679(4) | 0.839(2) | 0.58(1)  | 1 | 0.05(4)  | 9  |
| O9  | 0.669(2) | 0.925(2) | 0.749(7) | 1 | 0.02(1)  | 18 |
| O12 | 0.652(1) | 0.962(2) | 0.096(5) | 1 | 0.02(2)  | 18 |
| O15 | 0.610(2) | 0.891(2) | 0.338(7) | 1 | 0.04(1)  | 18 |
| C2m | 0.628(2) | 0.814(1) | 0.128(7) | 1 | 0.01(1)  | 9  |
| H7m | 0.619(3) | 0.809(2) | 0.28(1)  | 1 | 0.01(2)  | 18 |

TABLE 14

Atomic parameters from Rietveld refinement of Ni$_2$(m-dobdc) dosed with 1.0 D$_2$ per Ni$^{2+}$ at 10 K [NCNR, BT1], R3m, a = 25.749(4) Å, c = 6.739(1) Å, V = 3870. (1) Å$^3$. Values in parentheses indicate one standard deviation in the refined value. Goodness-of-fit parameters: $\chi^2$ = 0.988; wRp = 3.77%; Rp = 3.08%. Refined composition: Ni$_{18}$H$_{18}$C$_{72}$O$_{54}$D$_{35.46}$.

| Atom | X | Y | Z | Occupancy | U$_{(ISO)}$ (Å$^2$) | Multiplicity |
|---|---|---|---|---|---|---|
| C1  | 0.658(1)  | 0.875(1)  | 0.836(5) | 1       | 0.02(1)    | 18 |
| C2  | 0.668(2)  | 0.8339(8) | 0.748(7) | 1       | 0.003(11)  | 9  |
| C6  | 0.647(1)  | 0.869(1)  | 0.054(5) | 1       | 0.022(9)   | 18 |
| C11 | 0.635(1)  | 0.912(1)  | 0.172(4) | 1       | 0.020(9)   | 18 |
| Ni2 | 0.3262(8) | 0.3720(8) | 0.563(2) | 1       | 0.006(4)   | 18 |
| H7  | 0.671(3)  | 0.836(2)  | 0.613(9) | 1       | 0.02(2)    | 9  |
| O9  | 0.673(1)  | 0.929(1)  | 0.759(4) | 1       | 0.000(7)   | 18 |
| O12 | 0.654(1)  | 0.965(1)  | 0.100(5) | 1       | 0.01(1)    | 18 |
| O15 | 0.610(2)  | 0.893(2)  | 0.357(5) | 1       | 0.04(1)    | 18 |
| C2m | 0.630(2)  | 0.8148(8) | 0.135(5) | 1       | 0.003(10)  | 9  |
| H7m | 0.624(2)  | 0.812(1)  | 0.27(1)  | 1       | 0.003(17)  | 9  |
| D1  | 0.2095(9) | 0.219(1)  | 0.018(4) | 1.97(7) | 0.15(2)    | 18 |

TABLE 15

Atomic parameters from Rietveld refinement of Ni$_2$(m-dobdc) dosed with 2.0 D$_2$ per Ni$^{2+}$ at 10 K [NCNR, BT1], R3m, a = 25.776(5) Å, c = 6.754(2) Å, V = 3887.(1) Å$^3$. Values in parentheses indicate one standard deviation in the refined value. Goodness-of-fit parameters: $\chi^2$ = 1.676; wRp = 4.69%; Rp = 3.70%. Refined composition: Ni$_{18}$H$_{18}$C$_{72}$O$_{54}$D$_{69.30}$.

| Atom | X | Y | Z | Occupancy | U$_{(ISO)}$ (Å$^2$) | Multiplicity |
|---|---|---|---|---|---|---|
| C1  | 0.660(2)  | 0.877(2)   | 0.832(7) | 1      | 0.02(1)   | 18 |
| C2  | 0.672(3)  | 0.836(1)   | 0.74(1)  | 1      | 0.01(2)   | 9  |
| C6  | 0.648(2)  | 0.869(2)   | 0.051(6) | 1      | 0.02(1)   | 18 |
| C11 | 0.632(2)  | 0.909(1)   | 0.162(5) | 1      | 0.01(1)   | 18 |
| Ni2 | 0.325(1)  | 0.3697(9)  | 0.557(3) | 1      | 0.002(6)  | 18 |
| H7  | 0.673(4)  | 0.836(2)   | 0.59(2)  | 1      | 0.02(3)   | 9  |
| O9  | 0.674(2)  | 0.928(2)   | 0.764(6) | 1      | 0.01(1)   | 18 |
| O12 | 0.656(2)  | 0.964(2)   | 0.097(7) | 1      | 0.02(2)   | 18 |
| O15 | 0.615(2)  | 0.894(2)   | 0.351(8) | 1      | 0.05(2)   | 18 |
| C2m | 0.627(2)  | 0.813(1)   | 0.138(8) | 1      | 0.01(2)   | 9  |
| H7m | 0.623(4)  | 0.812(2)   | 0.26(2)  | 1      | 0.00(3)   | 9  |
| D1  | 0.211(1)  | 0.218(1)   | 0.009(4) | 2.0(1) | 0.09(2)   | 18 |
| D2  | 0.782(2)  | 0.955(2)   | 0.434(7) | 1.6(1) | 0.16(3)   | 18 |
| D3  | 0.569(3)  | 0.138(5)   | 0.48(1)  | 0.4(1) | 0.01(5)   | 9  |

TABLE 16

Atomic parameters from Rietveld refinement of $Ni_2$(m-dobdc) dosed with 3.0 $D_2$ per $Ni^{2+}$ at 10 K [NCNR, BT1], R3m, a = 25.802(5) Å, c = 6.761 (2) Å, V = 3898. (1) Å$^3$. Values in parentheses indicate one standard deviation in the refined value. Goodness-of-fit parameters: $\chi_v^2$ = 1.545; wRp = 4.64%; Rp = 3.84%. Refined composition: $Ni_{18}H_{18}C_{72}O_{54}D_{103.86}$.

| Atom | X | Y | Z | Occupancy | $U_{(ISO)}$ (Å$^2$) | Multiplicity |
|---|---|---|---|---|---|---|
| C1 | 0.662(2) | 0.878(2) | 0.827(7) | 1 | 0.01(1) | 18 |
| C2 | 0.672(3) | 0.836(1) | 0.75(1) | 1 | 0.00(2) | 9 |
| C6 | 0.647(2) | 0.869(2) | 0.057(6) | 1 | 0.02(1) | 18 |
| C11 | 0.634(2) | 0.911(2) | 0.171(6) | 1 | 0.03(1) | 18 |
| Ni2 | 0.327(1) | 0.373(1) | 0.557(4) | 1 | 0.008(7) | 18 |
| H7 | 0.670(6) | 0.835(3) | 0.61(2) | 1 | 0.07(5) | 9 |
| O9 | 0.671(2) | 0.923(2) | 0.763(7) | 1 | 0.01(1) | 18 |
| O12 | 0.655(2) | 0.963(2) | 0.083(8) | 1 | 0.02(2) | 18 |
| O15 | 0.612(3) | 0.892(3) | 0.35(1) | 1 | 0.07(2) | 18 |
| C2m | 0.631(2) | 0.816(1) | 0.129(7) | 1 | 0.01(2) | 9 |
| H7m | 0.620(4) | 0.810(2) | 0.28(2) | 1 | 0.02(3) | 9 |
| D1 | 0.210(1) | 0.217(1) | 0.013(4) | 2.0 | 0.08(1) | 18 |
| D2 | 0.778(2) | 0.953(2) | 0.419(6) | 2.0 | 0.17(2) | 18 |
| D3 | 0.5778(9) | 0.156(2) | 0.530(6) | 2.0 | 0.10(1) | 9 |
| D4 | 0.587(2) | 0.173(4) | −0.02(1) | 1.5(1) | 0.26(7) | 9 |

Inelastic Neutron Scattering.

Inelastic neutron scattering (INS) spectra were collected using the Filter Analyzer Neutron Spectrometer (FANS) according to Udovic et al. (*Nucl. Inst. and Meth. Phys. Res A* 588:406 (2008)) at the NCNR on the same samples used for the NPD experiments. Spectra were obtained at 7 K using the pyrolytic graphite (002) monochromator and 20'-20' collimation options. Data were first collected for the bare framework, followed by data collection for the sample loaded with normal-$H_2$ (n-$H_2$), which contains a 3:1 mixture of ortho (o-$H_2$) and para (p-$H_2$), respectively. For $Co_2$(m-dobdc), data were collected at loadings of 0.33, 0.67, 1.0, 2.0, 3.0, and 4.0 n-$H_2$ molecules per Co atom, while for $Ni_2$(m-dobdc) data were collected at loadings of 0.67, 1.0, 2.0, 3.0, and 4.0 n-$H_2$ molecules per Ni atom. Gas was loaded into the materials using the same methodology as described in the NPD experiments. The spectra of the bare frameworks were subtracted from the spectra obtained from the $H_2$ loaded samples and Gaussian peaks were fit to the rotational transitions using the DAVE suite of programs according to Azuah et al. (*J. Res. Natl. Inst. Stan. Technol.* 114:241 (2009)). Further measurements of the framework vibrational densities of states for the activated $Co_2$ (m-dobdc) material were made to higher energies (35 meV to 160 meV) using the Cu(220) monochromator with 20'-20' collimation.

Infrared Spectroscopy.

Infrared spectra were acquired using a Bomem DA3 Michelson interferometer equipped with a glowbar source, $CaF_2$ beamsplitter and a liquid nitrogen cooled mercury-cadmium-telluride detector. A cutoff filter above 9000 cm$^{-1}$ was used to prevent unwanted sample heating from the IR source. A custom-built diffuse reflectance system according to FitzGerald et al. (*Rev. Sci. Instrum.* 77:093110 (2006)) with a sample chamber that allows both the temperature and atmosphere of the material to be controlled was utilized for all experiments. Powder samples of the frameworks (ca. 10 mg) were transferred under inert atmosphere to a cup affixed to a copper slab providing thermal contact to a cold-finger cryostat (Janis ST-300T). The sample temperature was monitored by a Si-diode thermometer. Known quantities of $H_2$ gas were dispensed from a calibrated gas manifold by monitoring the change in pressure.

DFT Calculations.

Due to the extended nature of the M2 (dobdc) and $M_2$ (m-dobdc) structures, cluster modeling was completed on the linker of interest coordinated to a pair of Co atoms bound to either end of the organic linker. To truncate the system, the ligating oxygen atoms that are not part of the included linker were added as formaldehyde molecules in order to conserve charge. The experimentally determined crystal structures were truncated as described and frozen. The geometry of a hydrogen molecule bound to the frozen system based on neutron diffraction data was then optimized. The range-separated, dispersion corrected functional ωB97X-D implemented in the electronic structure software Q-Chem as described in Shao et al. (*Phys. Chem. Chem. Phys.* 8:3172 (2006)) was used with an ultra fine (99, 590) grid and a triple split-valence basis set with polarization as described in Krishnan et al. (*J. Chem. Phys.* 72:650 (1980)) and McLean et al. (*J. Chem. Phys.* 72:5639 (1980)). A small core Stuttgart-Born (SRSC) effective core potential is employed to model the core electrons of the Co, as described in Dolg et al. (*J. Chem. Phys.* 86:2123 (1987)). Binding is further analyzed using the ALMO EDA as described in Khaliullin et al. 2007 (*J. Chem. Phys.* 111:8753 (2007)). Charge transfer is accounted for using the perturbative Roothaan step approach, which allows for assignment of forward and backbonding energies as well as generation of complementary occupied-virtual orbital pairs (COVPs) as described in Khaliullin et al. 2008 (*J. Chem. Phys.* 128:184112 (2008)) to visualize charge transfer.

Structural Characterization of $M_2$ (m-dobdc).

Figure 7:
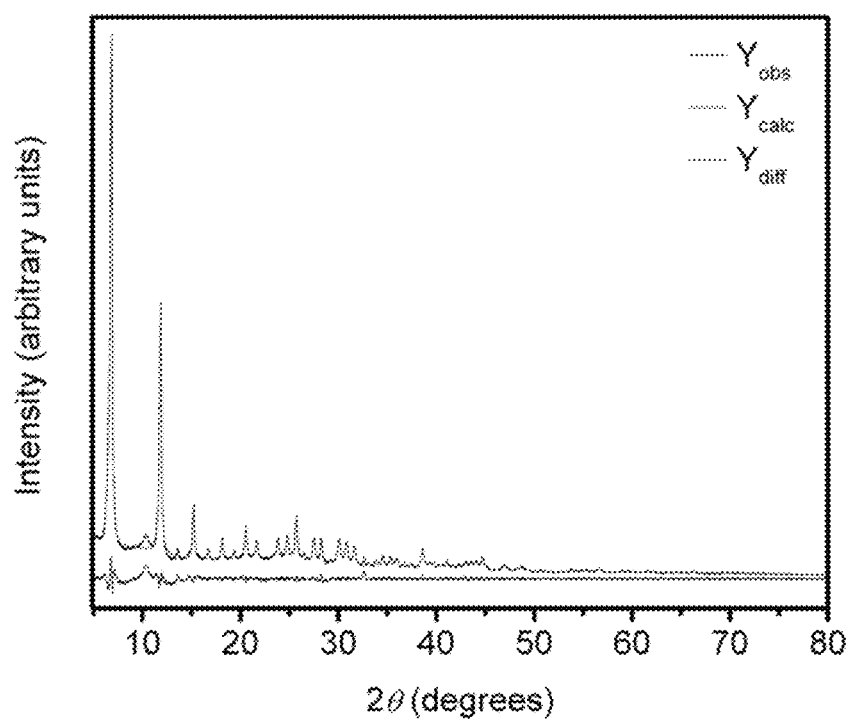
FIG. 7 presents a powder X-ray diffraction pattern of $Mg_2$ (m-dobdc) ($Y_{obs}$ top line) with calculated diffraction pattern ($Y_{calc}$; substantially overlaps with $Y_{obs}$) from Le Bail refinement with difference (bottom). Unit cell parameters: a axis, 25.893(2) Å; c axis, 6.71(1) Å; V=3955 (1) Å$^3$.
Figure 8:
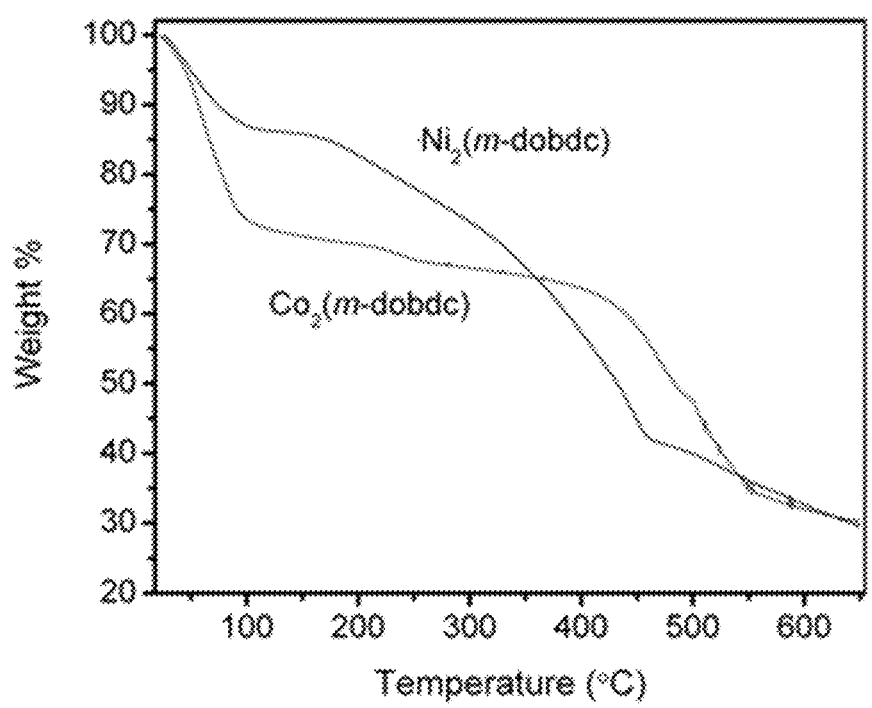
FIG. 8 presents a thermogravimetric analysis of $Co_2$ (m-dobdc) and $Ni_2$ (m-dobdc) at a ramp rate of 2° C. per min.
Figure 9:
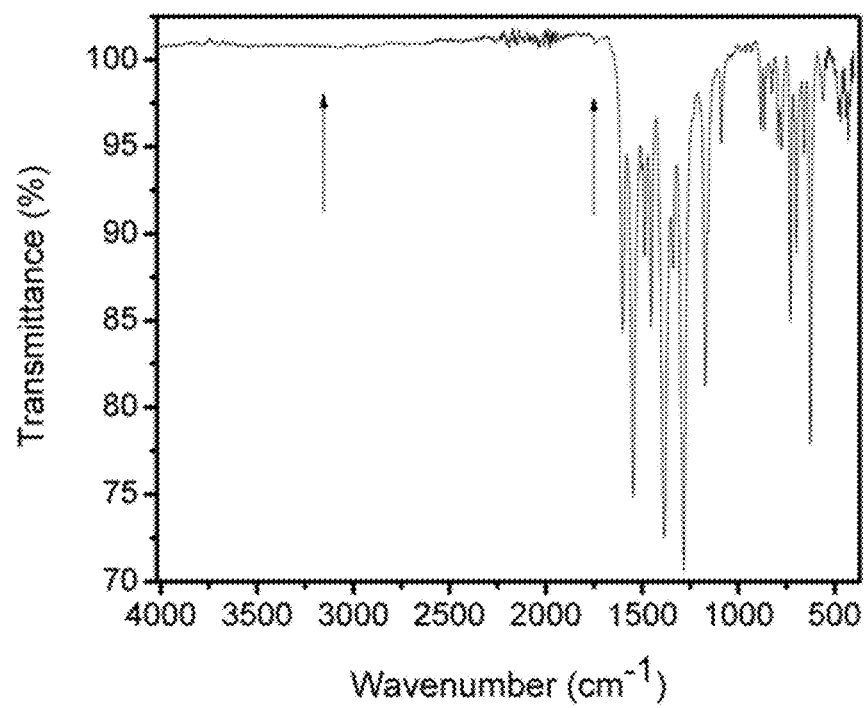
FIG. 9 provides an infrared spectrum of the fully evacuated sample of $Mn_2$ (m-dobdc). Note the loss of the DMF and MeOH peaks indicated by arrows.
Figure 10:
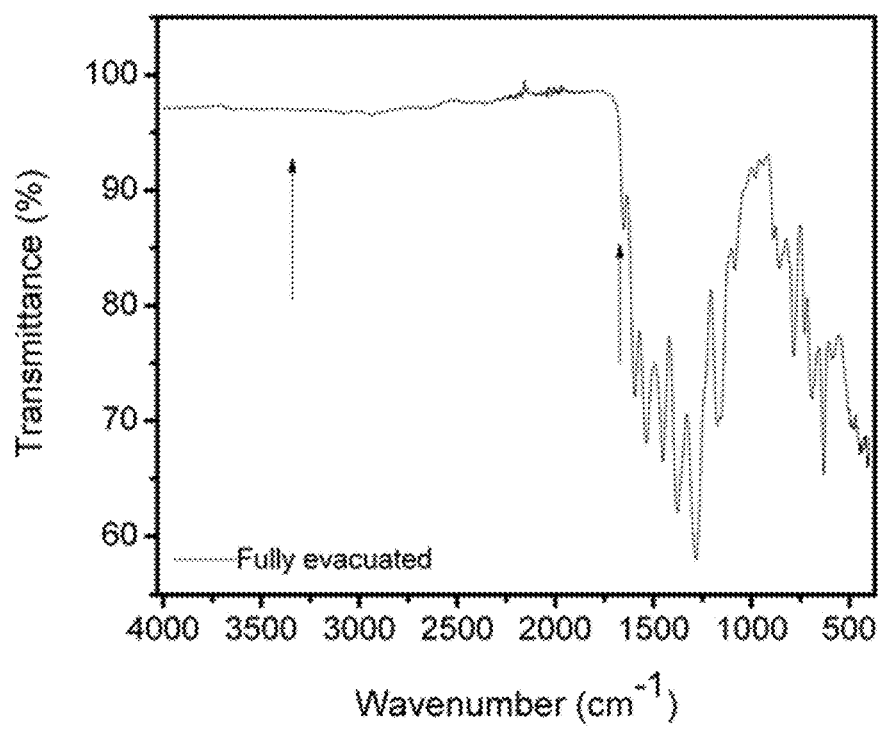
FIG. 10 provides an infrared spectrum of the fully evacuated sample of $Fe_2$ (m-dobdc).
Figure 11:
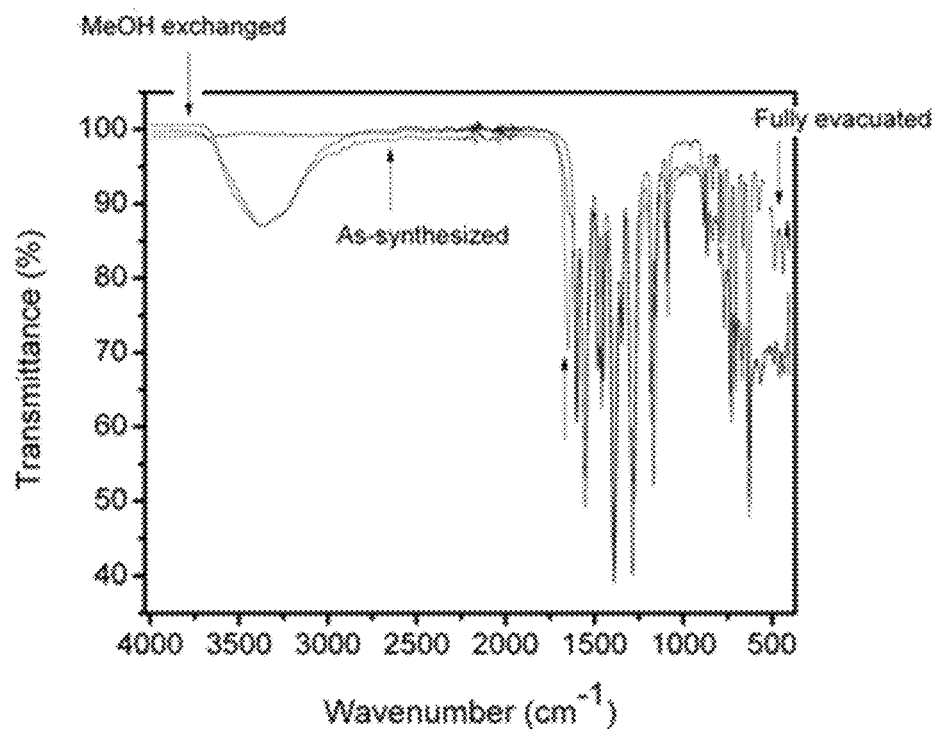
FIG. 11 provides an infrared spectrum of $Co_2$ (m-dobdc) showing the loss of MeOH and DMF upon evacuation, with arrows noting the MeOH and DMF peaks.
Figure 12:
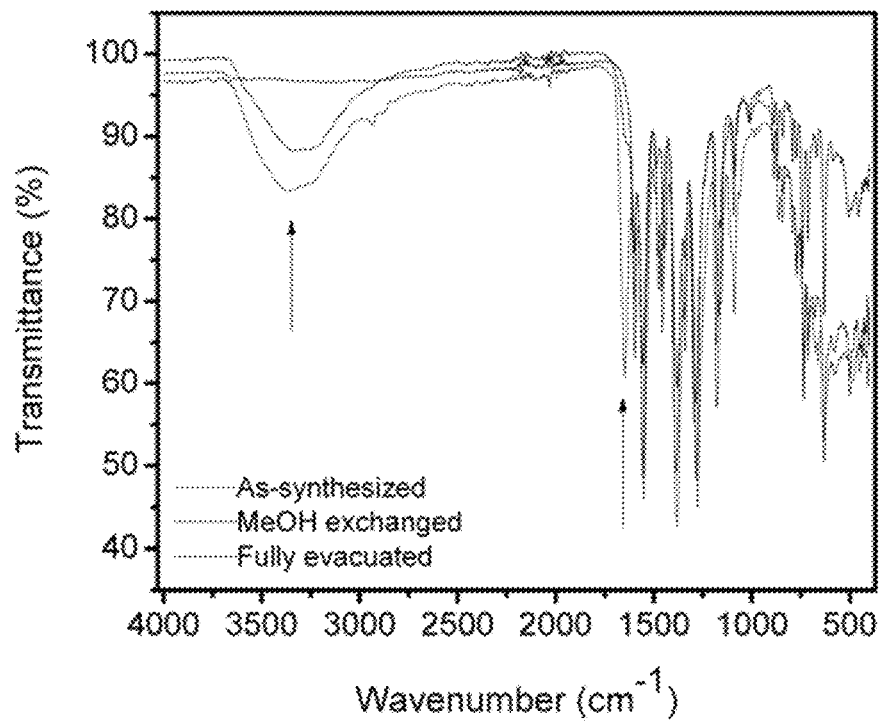
FIG. 12 provides an infrared spectrum of $Ni_2$ (m-dobdc) showing the loss of MeOH and DMF upon evacuation, with arrows noting the MeOH and DMF peaks.
Figure 13:
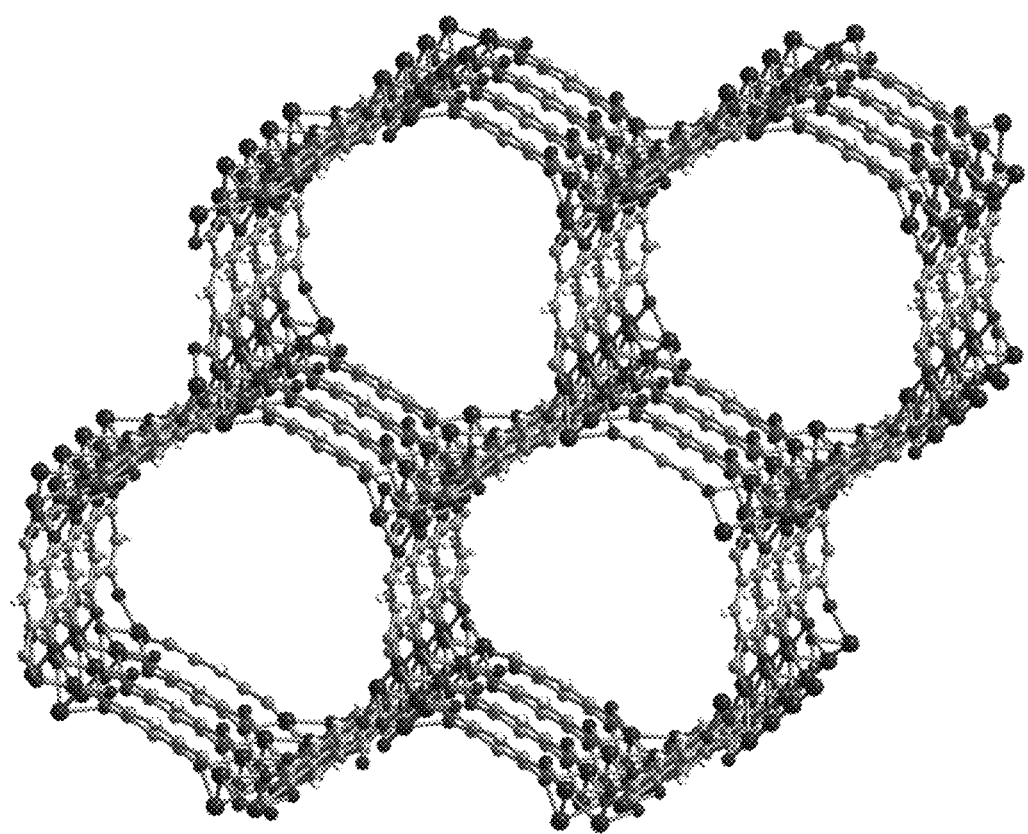
FIG. 13 provides the crystal structure of $Co_2$ (m-dobdc) showing one-dimensional hexagonal pores and helical metal chains.

A comparison of the $H_4$dobdc and $H_4$ (m-dobdc) linkers can be seen in FIG. 1; the regioisomer of $H_4$ (dobdc) was targeted in order to form a framework with a high density of open metal coordination sites and with a different local geometry around the metal and altered electronics than in $M_2$ (dobdc). Optimal synthetic conditions for $M_2$ (m-dobdc) (M=Mn, Fe, Co, or Ni) were generally found to involve the reaction of an anhydrous $MCl_2$ salt with $H_4$ (m-dobdc) for 18 h in a variably concentrated mixture of MeOH in DMF. These conditions yielded solvated crystalline frameworks, which were isolated as pink, beige, pink, and light green microcrystalline solids, respectively. The PXRD patterns for $M_2$ (m-dobdc) (M=Mn, Fe, Co, Ni) (see FIGS. 3-6) were found to diffract at similar angles, indicating that this series is isostructural. Additionally, the patterns for Mn, Co, and Ni were indexed using a structureless Le Bail refinement to determine unit cell parameters for these frameworks (see Table 1). A Mg analog was also synthesized; the PXRD pattern for this framework was indexed and had similar unit cell parameters to the the other indexed frameworks (see FIG. 7), indicating that this sample is isostructural with the others. However, activation proved difficult and led to a low surface area for the sample and thus low gas uptake. Thermogravimetric analyses of the $Co_2$ (m-dobdc) and $Ni_2$ (m-dobdc) frameworks show initial mass losses of 33% and 14%, respectively, indicative of volatilization of trapped solvent molecules and thus porosity (see FIG. 8). After solvent exchanges in MeOH, full activation was achieved by heating under dynamic vacuum at 180° C., which was reflected in the disappearance of both the DMF peak at 1651 $cm_{-1}$ and the MeOH peak at 3350 $cm^{-1}$ in the infrared absorption spectra (see FIGS. 9-12). The crystal structure of $Co_2$ (m-dobdc) was solved from powder X-ray diffraction data and neutron diffraction data (see FIG. 13). $Co_2$ (m-dobdc) crystallizes with one-dimensional hexagonal channels and helical metal chains as in $M_2$ (dobdc); however, $Co_2$ (m-dobdc) crystallizes in the R3m space group, as opposed to the R$\overline{3}$ space group in which the $M_2$ (dobdc) structures crystallize. While surprisingly similar, the $M_2$ (dobdc) and $M_2$ (m-dobdc) structures are not identical. This is reasonable considering the change in point group symmetry of the linker from Cm in $H_4$dobdc to $C_{2v}$ in $H_4$ (m-dobdc), leading to the change in space group. Further structural differences were seen between $Co_2$ (m-dobdc) and $Co_2$ (dobdc), with the latter structure being previously reported. The orientation of the carboxylate group in the linker is changed; COO⁻ is twisted out of the plane of the aromatic ring by approximately 12.5° in $Co_2$ (m-dobdc) and only approximately 3.5° in $Co_2$ (dobdc). Furthermore, both structures are comprised of helical chains of Co atoms, with every third atom facing into the same pore with its open metal coordination site. In $Co_2$ (m-dobdc), metals facing into the same pore align directly along the crystallographic b axis, for a Co—Co distance of 14.9(2) Å across the pore from neutron and X-ray diffraction data. In $Co_2$ (dobdc), the metals are offset from each other by ⅓ twist in the chain, leading to a Co—Co distance of 15.24(8) Å. Overall, this indicates that, while sharing some structural features with $M_2$ (dobdc), the $M_2$ (m-dobdc) series is a completely new framework series with different connectivity, a different geometry around the metal centers, a different space group, and several other structural features that distinguish it from any known metal-organic framework.

Figure 14:
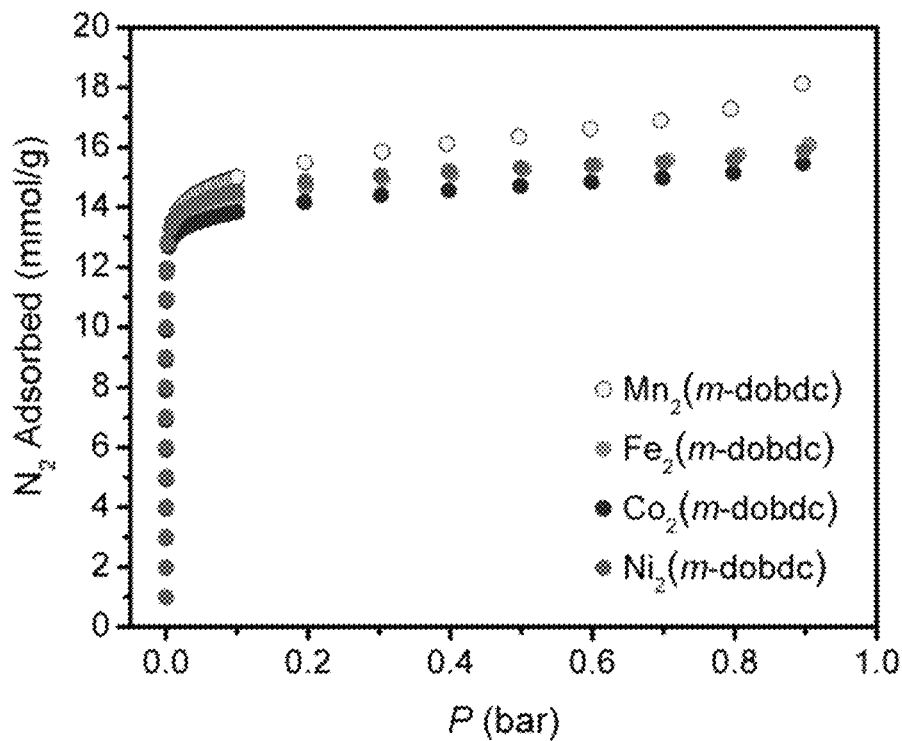
FIG. 14 provides $N_2$ adsorption isotherms at 77 K used to calculate the Langmuir and BET surface areas of $Mn_2$ (m-dobdc) (top dots), $Fe_2$ (m-dobdc), $Co_2$ (m-dobdc) (bottom dots), and $Ni_2$ (m-dobdc).

Low-pressure $N_2$ adsorption isotherms at 77 K revealed type I adsorption isotherms for all four samples, characteristic of microporous solids (see FIG. 14). Fits to the data gave Langmuir and BET surface areas for each sample (see TABLE 17), comparable to those reported for $M_2$ (dobdc) in several sources (Zhou et al. *J. Am. Chem. Soc.* 130:15268 (2008); Dietzel et al. *Chem. Commun.* 46:4962 (2010); Queen et al. *Dalton Trans.* 41:4180 (2012); Geier et al. *Chem. Sci.* 4:2054 (2013); Mason et al. *Chem. Sci.* DOI: 10.1039/C3SC5633J (2013)). Based on the similar framework structure, this indicates full evacuation of the pores and availability of open metal coordination sites for interaction with gas molecules. Furthermore, the experimentally obtained surface area measurements match well with geometrically predicted surface areas; a simple program in Düern et al. (*J. Phys. Chem. C* 111:15350 (2007)) was used to predict the BET surface area of $Co_2$ (m-dobdc) to be 1297.01 m²/g, which matches well with the experimentally obtained value of 1264 m²/g. Consistency checks of the calculated BET surface areas for each of the samples were used to determine if the calculated BET surface areas are accurate (FIGS. 25-32), per Walton and Snurr (*J. Am. Chem. Soc.* 129:8552 (2007)).

TABLE 17

Langmuir and BET surface areas of the $M_2$(dobdc) and $M_2$(m-dobdc) frameworks.

|  |  | Mn | Fe | Co | Ni |
|---|---|---|---|---|---|
| $M_2$(dobdc) | Langmuir (m²/g) | 1797 | 1535 | 1432 | 1574 |
|  | BET (m²/g) | 1102 | 1360 | 1341 | — |
| $M_2$(m-dobdc) | Langmuir (m²/g) | 1741 | 1624 | 1504 | 1592 |
|  | BET (m²/g) | 1349 | 1295 | 1264 | 1321 |

Langmuir-Freundlich Fits for Calculation of $H_2$ Isosteric Heats of Adsorption. Langmuir-Freundlich Fits for Calculation of $H_2$ Isosteric Heats of Adsorption.

The dual-site Langmuir-Freundlich expression (Equation 1) was used to independently fit the combined isotherm data at 77 K and 87 K for $Mn_2$ (m-dobdc), $Fe_2$ (m-dobdc), and $Co_2$ (m-dobdc), where n is the amount adsorbed (mmol/g), $g_{sat}$ is the saturation loading for site A or B (mmol/g), b is the Langmuir parameter associated with either site A or B (bar$^{-v}$), p is the pressure, and v is a constant.

$$n = \frac{q_{sat,A} b_A p^{V_A}}{1 + b_A p^{V_A}} + \frac{q_{sat,B} b_B p^{V_B}}{1 + b_B p^{V_B}} \quad (1)$$

This equation provides the best fit for adsorption in metal-organic frameworks with exposed metal sites and is accurate at both low and high pressure extremes; the fits given are generally much better than those using the virial method. It should be noted that the Tóth equation was also explored for fitting isotherms based on reports in Tedds et al. (*Faraday Discuss.* 151:75 (2011)) that it was more accurate at extreme pressures, but essentially equivalently accurate fits were found.

The $Ni_2$ (m-dobdc) and $Ni_2$ (dobdc) data were fit with the tri-site Langmuir expression (Equation 2). The data at 77 K and 87 K was fit simultaneously for each sample, respectively. This fitting method was necessary to find a quality fit due to the extreme steepness in the low-pressure regime of the isotherm data, which led to inadequate fits with the dual-site Langmuir-Freundlich expression being fit at each temperature independently. In the Langmuir expression, $q_{sat}$ is the saturation loading for site A, B, or C (mmol/g), b is the Langmuir parameter associated with site A, B, or C (bar$^{-1}$), and p is the pressure. The value for b is calculated per equation 3.

$$n = \frac{q_{sat,A} b_A p}{1 + b_A p} + \frac{q_{sat,B} b_B p}{1 + b_B p} + \frac{q_{sat,C} b_C p}{1 + b_C p} \quad (2)$$

$$b = b_0 e^{\frac{-E}{RT}} \quad (3)$$

The equation was fit using the statistical software package of OriginPro. The quality of fits was determined by comparing the adjusted $R^2$ and residual sum of squares values, as well as by visual inspection. Wolfram Mathematica was then used to create a series of data points corresponding to points on the fit curve. The isosteric heat of adsorption $Q_{st}$ was then calculated using the data points from Mathematica for both the 77 K and 87 K isotherms using the Clausius-Clapeyron relation (see Eq. 4) at equivalent loadings (n, mmol/g). $Q_{st}$ is the isosteric heat of adsorption (kJ/mol), R is the gas constant $$\left(\frac{L \times \text{bar}}{[\text{mol} \times K]}\right),$$

and P is the pressure at a given n at either $T_2$ (87 K) or $T_1$ (77 K).

$$Q_{st} = -\frac{R[\ln(P_{T_2}) - \ln(P_{T_1})]}{T_2^{-1} - T_1^{-1}} \quad (4)$$

$H_2$ Adsorption Isotherms.

Figure 69:
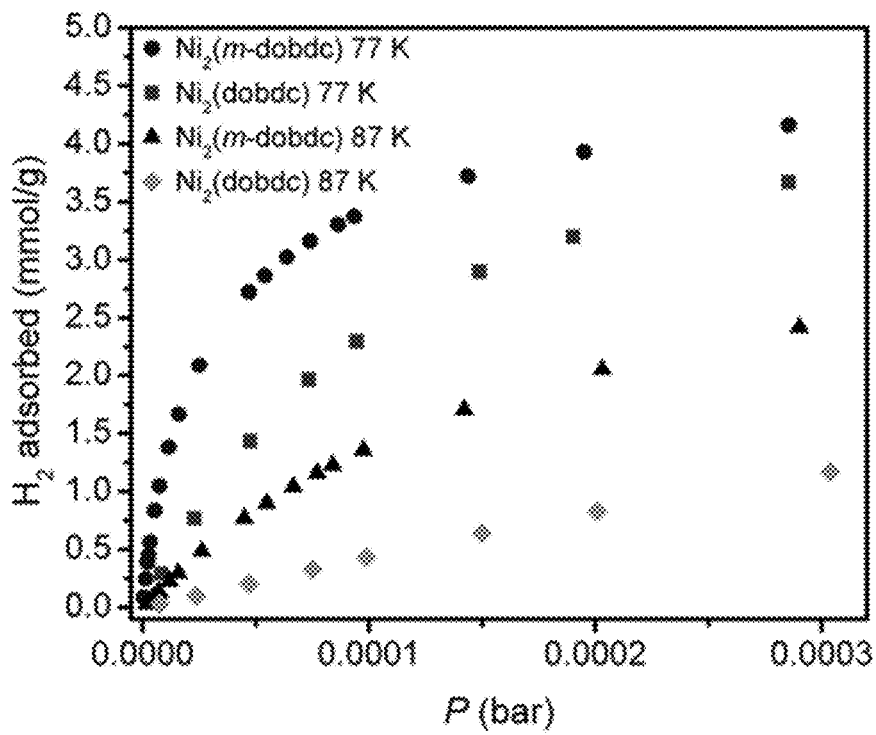
FIG. 69 a low-pressure comparison of $Ni_2$ (m-dobdc) (circles) and $Ni_2$ (dobdc) (squares) at 77 K (blue) and 87 K (red). Note the steepness of the $Ni_2$ (m-dobdc) isotherms as compared to the $Ni_2$ (dobdc) isotherms.
Figure 70:
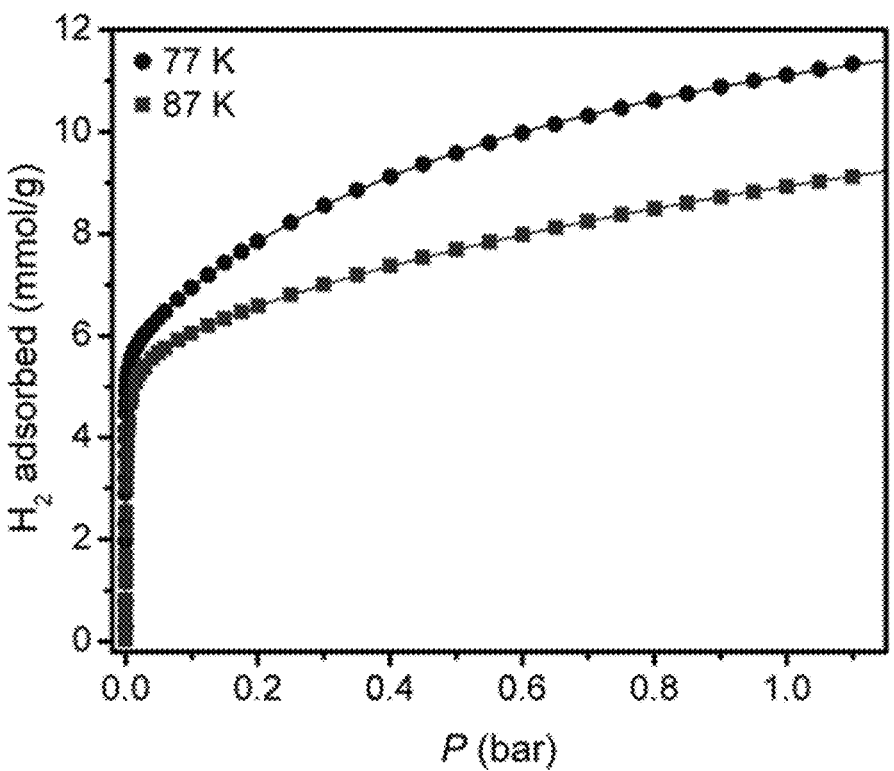
FIG. 70 shows $H_2$ adsorption isotherms at 77 K and 87 K for $Ni_2$ (dobdc). The solid lines represent the tri-site Langmuir fit to the data.
Figure 71:
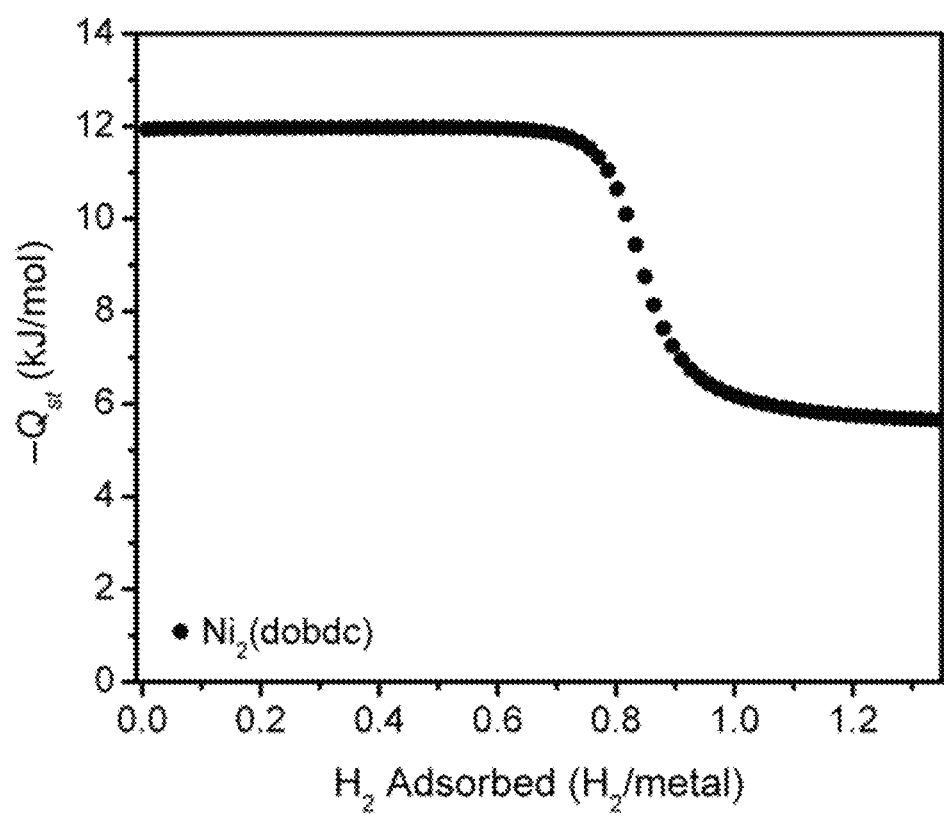
FIG. 71 shows isosteric heat of adsorption curve for $Ni_2$ (dobdc) as a function of the amount adsorbed.

To probe the structural differences and potential modified electronics at the open metal coordination sites in $M_2$ (m-dobdc), $H_2$ was used as a probe. By measuring the $H_2$ adsorption isotherms, the interaction of the $M_2$ (m-dobdc) series of frameworks with small gas molecules in general can be explored. Surprisingly, the structural differences discussed above contribute to an increased $H_2$ uptake in most of these $M_2$ (m-dobdc) frameworks as compared to their $M_2$ (dobdc) counterparts. Low-pressure $H_2$ adsorption isotherms were collected for all four frameworks at 77 K and 87 K (see FIGS. 15-18). The greatest $H_2$ uptake of the four frameworks is seen in $Ni_2$ (m-dobdc), which is expected, as $Ni_2$ (dobdc) has the highest $H_2$ uptake of the $M_2$ (dobdc) series at 77 K and 1.0 bar. Interestingly, the $Ni_2$ (m-dobdc) framework has exceptional uptake at extremely low pressures in the range <0.0002 bar (see FIG. 69) In order to determine the isosteric heats of $H_2$ adsorption, isotherm data was independently fit using the Langmuir-Freundlich equation and the fits were used to calculate binding enthalpies for each framework using the Clausius-Clapeyron relation (see FIG. 19). Dual-site Languir fit parameters were then determined for the $H_2$ isotherms for $Mn_2$ (m-dobdc) (TABLE 18); $Fe_2$ (m-dobdc) (TABLE 19); $Co_2$ (m-dobdc) (TABLE 20); and $Ni_2$ (m-dobdc) (TABLE 21).

TABLE 18

Figure 15:
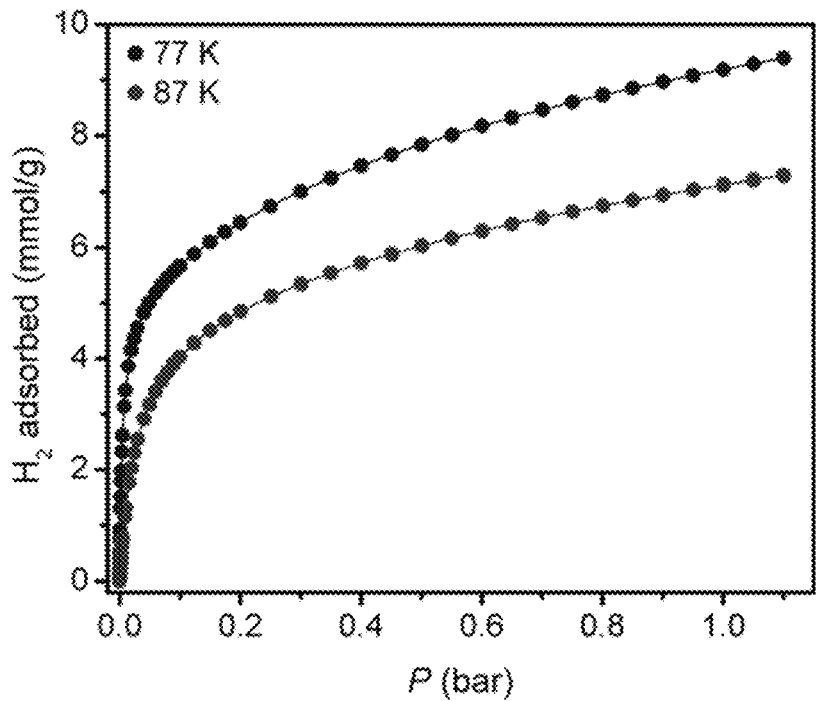
FIG. 15 provides $H_2$ adsorption isotherms at 77 K (top dots) and 87 K (bottom dots) for $Mn_2$ (m-dobdc). The solid lines represent the dual-site Langmuir fit to the data, using the parameters tabulated in TABLE 18.

Dual-site Langmuir fit parameters for the $H_2$ isotherms for $Mn_2$(m-dobdc) in FIG. 15.

| | 77 K | 87 K |
|---|---|---|
| $q_{sat,A}$ | 4.56 | 4.34 |
| $b_A$ | 212.50 | 34.65 |
| $v_A$ | 0.98 | 0.98 |
| $q_{sat,B}$ | 13.19 | 9.27 |
| $b_B$ | 0.54 | 0.46 |
| $v_B$ | 0.69 | 0.80 |

TABLE 19

Figure 16:
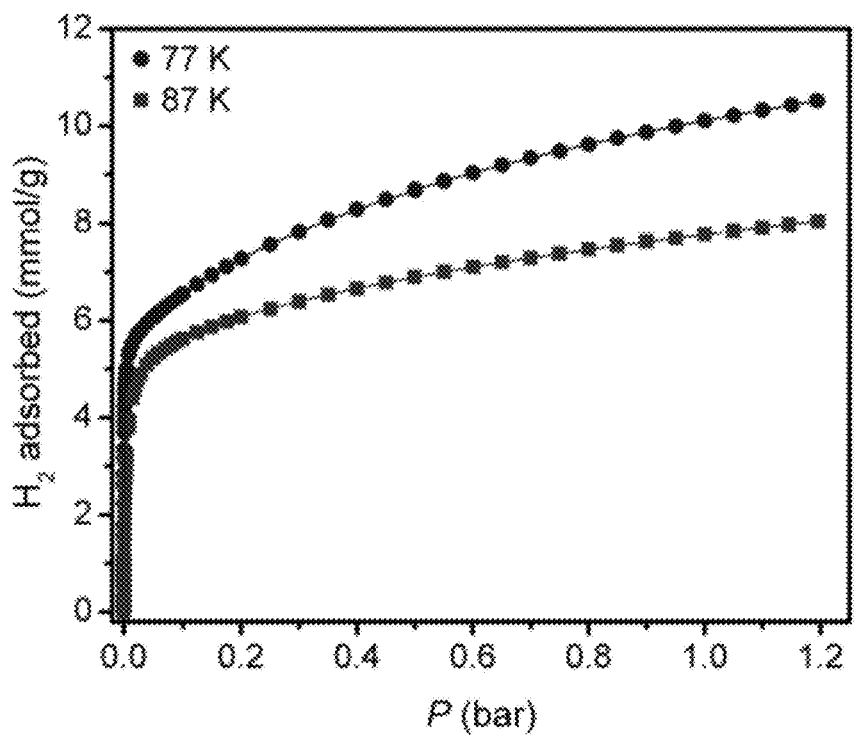
FIG. 16 provides $H_2$ adsorption isotherms at 77 K (top dots) and 87 K (bottom dots) for $Fe_2$ (m-dobdc). The solid lines represent the dual-site Langmuir fit to the data, using the parameters tabulated in TABLE 19.

Dual-site Langmuir fit parameters for the $H_2$ isotherms for $Fe_2$(m-dobdc) in FIG. 16.

| | 77 K | 87 K |
|---|---|---|
| $q_{sat,A}$ | 5.40 | 5.21 |
| $b_A$ | 1135.56 | 189.00 |

TABLE 19-continued

Dual-site Langmuir fit parameters for the $H_2$ isotherms for $Fe_2$(m-dobdc) in FIG. 16.

| | 77 K | 87 K |
|---|---|---|
| $v_A$ | 0.91 | 0.91 |
| $q_{sat,B}$ | 12.91 | 13.15 |
| $b_B$ | 0.58 | 0.25 |
| $v_B$ | 0.75 | 0.69 |

TABLE 20

Figure 17:
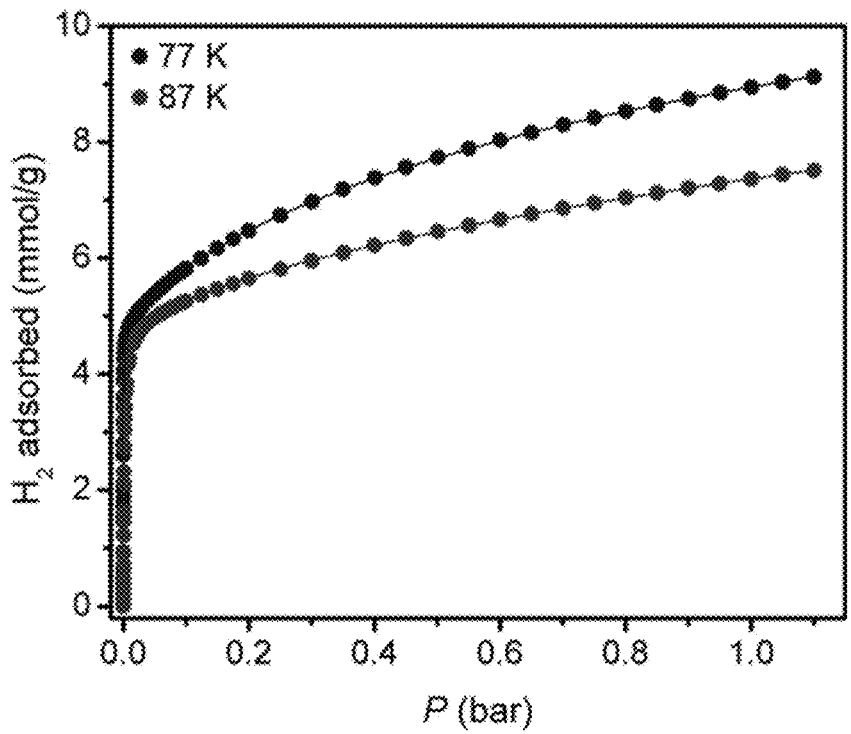
FIG. 17 provides $H_2$ adsorption isotherms at 77 K (top dots) and 87 K (bottom dots) for $Co_2$ (m-dobdc). The solid lines represent the dual-site Langmuir fit to the data, using the parameters tabulated in TABLE 20.

Dual-site Langmuir fit parameters for the $H_2$ isotherms for $Co_2$(m-dobdc) in FIG. 17.

| | 77 K | 87 K |
|---|---|---|
| $q_{sat,A}$ | 4.672 | 4.66 |
| $b_A$ | 3380.04 | 501.49 |
| $v_A$ | 0.90 | 0.90 |
| $q_{sat,B}$ | 10.89 | 24.80 |
| $b_B$ | 0.65 | 0.12 |
| $v_B$ | 0.73 | 0.65 |

TABLE 21

Figure 18:
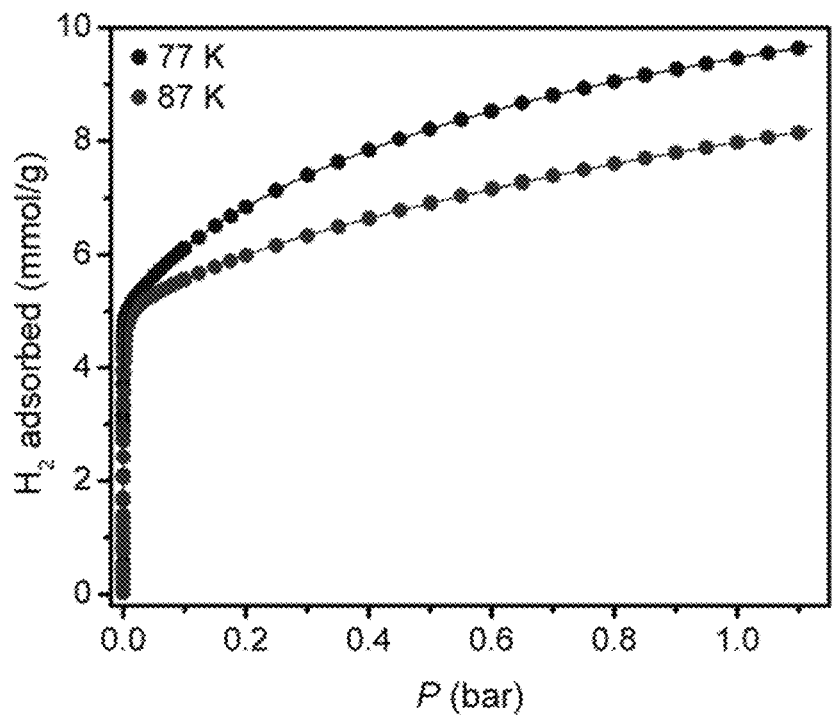
FIG. 18 provides $H_2$ adsorption isotherms at 77 K (top dots) and 87 K (bottom dots) for $Ni_2$ (m-dobdc). The solid lines represent the dual-site Langmuir fit to the data, using the parameters tabulated in TABLE 21.
Figure 19:
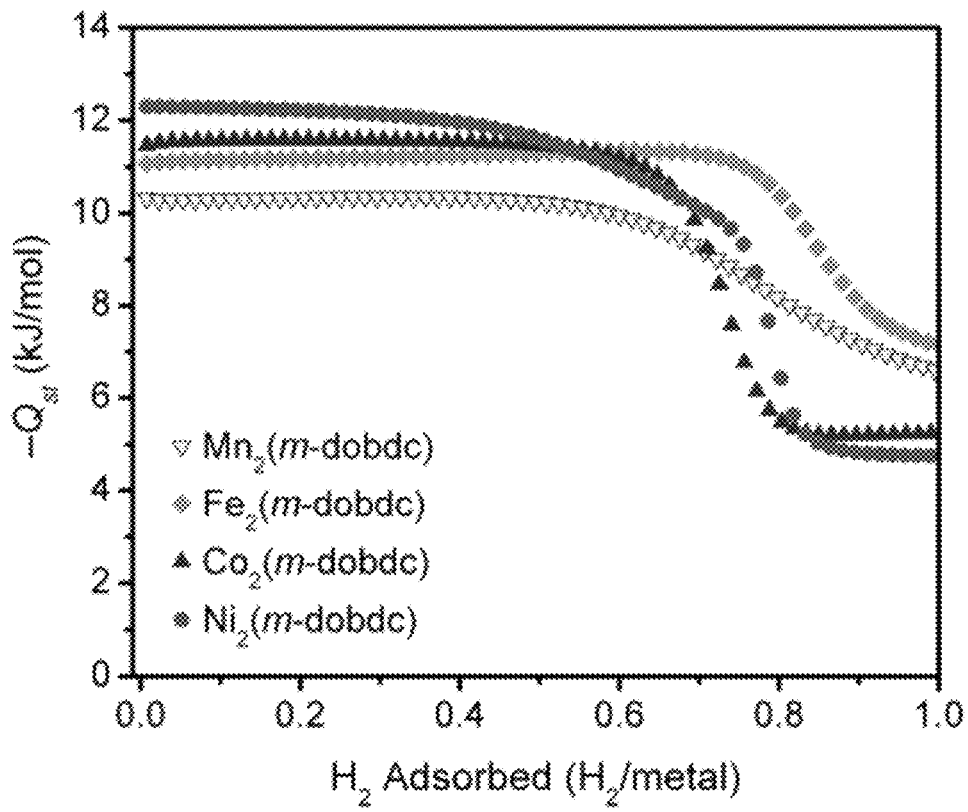
FIG. 19 provides $H_2$ isosteric heat of adsorption curves for the $M_2$ (m-dobdc) series of frameworks, calculated using the Clausius-Clapeyron relation.

Tri-site Langmuir fit parameters for the $H_2$ isotherms for $Ni_2$(m-dobdc) in FIG. 18.

| | 77 and 87 K |
|---|---|
| $q_{sat,A}$ | 3.78 |
| $b_A$ | 1.59E-4 |
| $E_A$ | 12.56 |
| $q_{sat,B}$ | 6.89 |
| $b_B$ | 9.97E-4 |
| $E_B$ | 4.79 |
| $q_{sat,C}$ | 1.30 |
| $b_C$ | 1.25E-3 |
| $E_C$ | 9.40 |

Isosteric heats of $H_2$ adsorption were calculated in order to gain insight into this increased $H_2$ adsorption and determine if there is a stronger interaction between $H_2$ and the metal centers in $M_2$ (m-dobdc). Similar to $M_2$ (dobdc) in Zhou et al. (*J. Am. Chem. Soc.* 130:15268 (2008)), the isosteric heat of adsorption plots for $Mn_2$ (m-dobdc), $Co_2$ (m-dobdc), and $Ni_2$ (m-dobdc) imply a nearly constant $H_2$ binding enthalpy until a load of approximately $0.75H_2/M^{2+}$, followed by a sharp decrease as all exposed metal cations become occupied and only weaker adsorption sites are available. This 75% coverage of the open coordination sites is on par with what has been seen in $M_2$ (dobdc) previously.

Increasing the binding enthalpy of $H_2$ in metal-organic frameworks is important for practical applications, as a binding enthalpy of −15 to −20 kJ/mol is predicted to be optimal for storing $H_2$ for use as a fuel. The low-coverage isosteric heats of adsorption of $Mn_2$ (m-dobdc), $Fe_2$ (m-dobdc), $Co_2$ (m-dobdc), and $Ni_2$ (m-dobdc) are −10.3, −11.1, −11.6, and −12.3 kJ/mol, respectively (see Table 22). This trend in binding enthalpies for $H_2$ is expected, as the Irving-Williams series predicts that high-spin complexes increase in stability moving from Group 7 to 10. This trend also mirrors that observed for $H_2$ binding to $M_2$ (dobdc) frameworks (Table 2). The value for $Ni_2$ (dobdc) was calculated from data presented in this work in order to maintain consistency between the $Ni_2$ (m-dobdc) and $Ni_2$ (dobdc), since isotherms for both were fit with the two temperatures simultaneously using a tri-site Langmuir model. Importantly, the isosteric heats of adsorption for $M_2$ (m-dobdc) are, on average, 1.0 kJ/mol stronger than in the corresponding $M_2$ (dobdc) frameworks (see Table 22) and are as much as 1.5 kJ/mol stronger in the case of Mn, which also has the largest percent increase (17%) in binding enthalpy.

TABLE 22

Comparison of low-loading $H_2$ isosteric heats of adsorption ($Q_{st}$, kJ/mol) in $M_2$(dobdc) and $M_2$(m-dobdc).

|  | Mn | Fe | Co | Ni |
|---|---|---|---|---|
| $M_2$(dobdc) | −8.8 | −9.7 | −10.8 | −11.9 |
| $M_2$(m-dobdc) | −10.3 | −11.1 | −11.5 | −12.3 |

Neutron Powder Diffraction.

Figure 20:
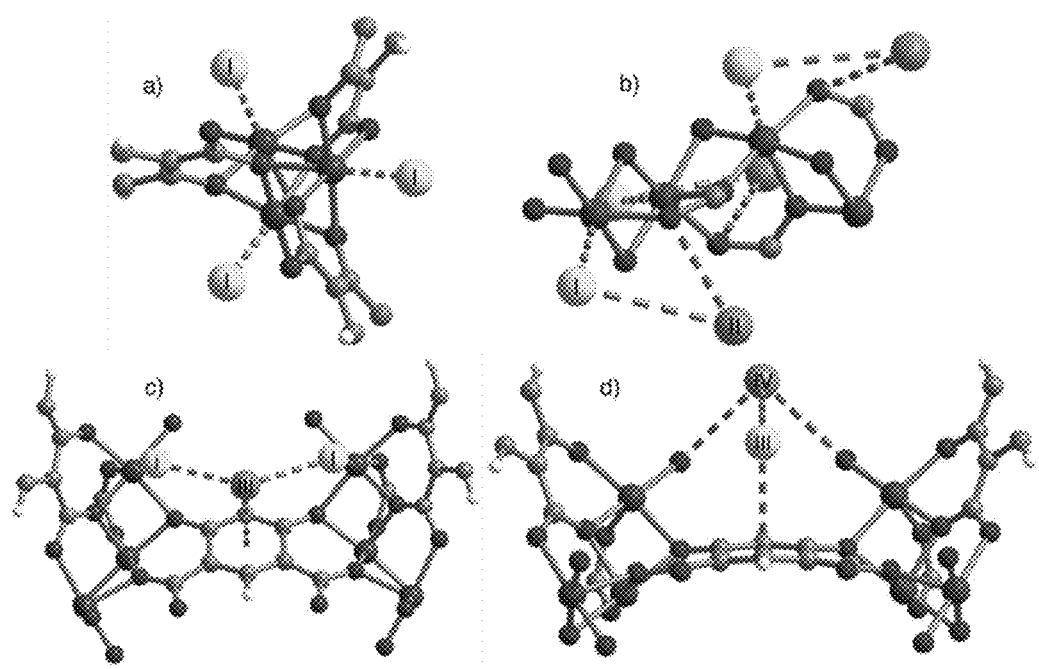
FIG. 20A-D presents the partial crystal structures of $Co_2$ (m-dobdc) showing (A) the primary binding site (site I) on the open metal site; (B) binding site II interacting with the $D_2$ in site I; (C) binding site III on the aromatic ring in the linker; and (D) binding site IV, interacting with the $D_2$ in site III. Spheres represent Co, C, O, and H atoms. "I", "II", "III" and "IV" spheres represent $D_2$ molecules.

In order to determine why the $M_2$ (m-dobdc) frameworks show higher binding enthalpy of $H_2$ than their the similar $M_2$ (dobdc) series, neutron diffraction was used with samples dosed with $D_2$. $D_2$ binding sites were determined for $Co_2$ (m-dobdc) by successively dosing the evacuated material with loadings of 0.75, 1.25, 1.5, 1.75, 2.0, 2.25, and 3.0 $D_2$ molecules per $Co^{2+}$ center and for $Ni_2$ (m-dobdc) by dosing 1.0, 2.0, and 3.0 $D_2$ molecules per $Ni^{2+}$ center. It is expected based on the structure and previous results for $M_2$ (dobdc) frameworks, as well as the isosteric heat of adsorption curves for $M_2$ (m-dobdc) that begin to decrease in binding enthalpy near loadings of $1H_2$/metal, that the open metal coordination site is the primary binding site. Indeed, this was found to be the only $D_2$ binding site (site I) in $Co_2$ (m-dobdc) at the lowest loading of 0.75 $D_2$ per $Co^{2+}$ (see FIG. 20A). The center of the $D_2$ electron density was found to be 2.23(5) Å from the metal, shorter than the 2.32(2) Å found for $Co_2$ (dobdc) at the same loading (Tables 4-5), which is further confirmation that the $H_2$ is binding more strongly to the open metal coordination site. The same binding site is seen in $Ni_2$ (m-dobdc), with a comparable M-$D_2$ distance of 2.18(4) Å at a loading of 1.0 $D_2$ per $Ni^{2+}$ at 10 K, which is within error of the distance seen in $Ni_2$ (dobdc) of 2.201(1) Å at 4 K in Brown et al. (*Chem. Phys.* [http://] . . . [dx.doi.org/10.1016/j.chemphys.2013.08.010 (2013)]). Increasing the $D_2$ loading in $Co_2$ (m-dobdc) reveals several secondary binding sites. At a loading of 1.25 $D_2$ per metal center, a second binding site (site II) is seen near the primary site (see FIG. 20B). This can be attributed to a $D_2$-$D_2$ interaction based on a short $D_2$-$D_2$ distance of 2.88(4) Å and a $D_2$-O interaction based on a distance of 3.28(6) Å to the nearest framework oxygen atom. This position is reasonable, considering that the $D_2$ can interact not only with the previously adsorbed $D_2$, but also with the pore wall surface; this is the only secondary binding site seen at this loading. Site II is in a similar location to the secondary binding site seen in $Co_2$ (dobdc) as well as that previously seen in $Mg_2$ (dobdc) in Sumida et al. (*Chem. Commun.* 47:1157 (2011)), whereby the second bound $D_2$ appears to rely on $D_2$-$D_2$ interactions in all cases. The site I-site II $D_2$-$D_2$ distance, however, of 3.05(2) Å in $Co_2$ (m-dobdc) at a loading of 2.25 $D_2$/metal is significantly shorter than the 3.16(2) Å observed at the same loading in $Co_2$ (dobdc) or the 3.16(8) Å seen for a similar loading of 1.2 $D_2$ per metal center in $Mg_2$ (dobdc). This shorter site I-site II distance in $Co_2$ (m-dobdc) is most likely a polarization effect, as the more strongly bound $D_2$ in site I is less negatively charged, leading to a stronger interaction with a $D_2$ adsorbed at site II.

A third binding site is seen (FIG. 20C) at higher loadings of $D_2$ approximately 3.08 Å above the mean plane of the aromatic ring in the linker (site III). Since the $Co_2$ (m-dobdc) has different symmetry than $Co_2$ (dobdc), this site is equidistant from the $D_2$ at neighboring site I positions in $Co_2$ (m-dobdc), which is not true in $Co_2$ (dobdc) and leads to two different site I-site III interactions. Importantly, there are only half as many site III bound $D_2$ molecules as in $Co_2$ (dobdc) at high loadings, which leads to the observation of a fourth binding site (FIG. 20D) (site IV) not seen in the $M_2$ (dobdc) series (a fourth site is seen in $Zn_2$ (dobdc) in Liu et al. (*Langmuir* 24:4772 (2008)) but this is not the same site seen in the $Co_2$ (m-dobdc) case). The new symmetry in this framework contributes to this additional binding site, as the two framework oxygen atoms that the $D_2$ in site IV interacts with are symmetrical in $Co_2$ (m-dobdc) but not in $Co_2$ (dobdc). Relative to site I, larger atomic displacement parameters for the refined $D_2$ at binding sites II, III, and IV are also indicative of weaker interactions. Neutron diffraction measurements of $Ni_2$ (m-dobdc) with different loadings of $D_2$ resulted in the identification of very similar binding sites as those found for $Co_2$ (m-dobdc) (Tables 14-16).

Examining the occupancies of the binding sites at various loadings in $Co_2$ (m-dobdc) leads to several conclusions. Increasing from loadings of 0.75 $D_2$ per metal site to 1.25 $D_2$ per metal site, it can be seen that site II begins to be populated before site I is entirely occupied, with occupancies of 0.94(2) $D_2$ in site I and 0.50(4) $D_2$ in site II at 1.25 $D_2$ per metal site (Tables 4,7). Furthermore, at a loading of 1.75 $D_2$ per metal site, site III begins to populate before site II is completely filled, which also has an effect on the early decrease in isosteric heat of adsorption of $H_2$ (Table 8). The early population of site III may be due to the increased symmetry of this site with regards to interactions with the site I $D_2$ molecules. In the results for $Ni_2$ (m-dobdc) (Tables 14-16), at 1.0 $D_2$ per metal, site I is fully occupied with an occupancy of 0.99(4). While 75% occupancy of the possible metal sites was seen based on $H_2$ adsorption data, this diffraction data indicates that 100% of the metal sites are occupied and thus available. This suggests that the open metal coordination sites were fully desolvated and the framework fully activated; the early decrease in binding enthalpy from adsorption data is possibly due to framework with collapsed or blocked pores. Increasing to 2.0 $D_2$ per metal retains full occupancy of site I with 1.0(1) $D_2$; the remaining $D_2$ are distributed between occupancies of 0.8(1) $D_2$ in site II and 0.2(1) $D_2$ in site III. At a loading of 3.0 $D_2$ per metal in $Ni_2$ (m-dobdc), sites I, II, and III are found to be fully occupied, while site IV has an occupancy of 0.75(1).

Inelastic Neutron Scattering Spectra.

Figure 21:
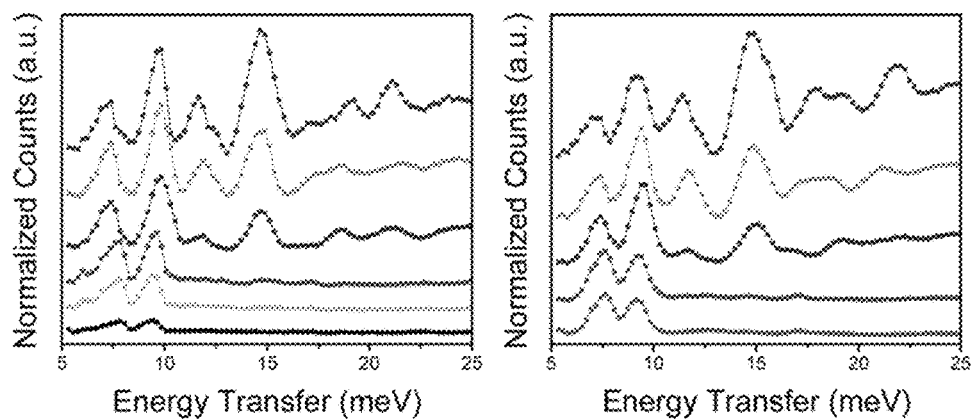
FIG. 21 presents INS data for $Co_2$ (m-dobdc) (left) and $Ni_2$ (m-dobdc) (right) at loadings of 0.33 (left panel—bottom), 0.50 (right panel—bottom), 0.67 (left panel—second from bottom), 1.0 (immediately above 0.50 and 0.67 values), 2.0 (above 1.0 values), 3.0 (above 2.0 values), and 4.0 (Top line) n-$H_2$ molecules per metal atom. Data are shown after subtraction of the spectrum of the evacuated framework and offset for clarity.

Inelastic neutron scattering (INS) experiments were carried out to probe the site-specific binding properties of $H_2$. Data for various loadings of $H_2$, after subtraction of the spectra of the evacuated materials are shown in FIG. 21. At loadings up to and including 1.0 n-$H_2$ molecules per metal atom, two low energy rotational lines are observed at 7.8(1) and 9.5(1) meV for $Co_2$ (m-dobdc) and 7.5(1) and 9.3(1) meV for $Ni_2$ (m-dobdc). These features are similar to those observed in INS spectra for several compounds in the $M_2$ (dobdc) series at low loadings, and have been assigned to transitions occurring from the J=0 state to sublevels of the split J=1 rotational state for initial $H_2$ adsorption at the metal centers. This assignment has been confirmed through correlation with neutron diffraction and DFT calculations. Presumably, there is a higher energy transition, not collected within this current data range, as seen in the $M_2$ (dobdc) series. The splitting between the low energy peaks of approximately 1.6 meV for both $Co_2$ (m-dobdc) and $Ni_2$ (m-dobdc) is smaller than that observed for any of the $M_2$ (dobdc) materials. The position of the first peak is at higher energies than that of the first peak of the $M_2$ (dobdc) materials (except the Zn analog), and the position of the second peak is at lower energies than is observed for all the $M_2$ (dobdc) materials. At loadings above 0.75$H_2$ per metal, as Sites II-IV begin to populate; the additional $H_2$ molecules affect the rotational potential at the metal site. This adjusts the rotational energy level, resulting in a shift of the first peak to lower energies and the second peak to higher energies. These peak shifts are similar to those observed for the $M_2$ (dobdc) materials, with magnitudes of approximately 0.7 meV for $Co_2$ (m-dobdc) and 0.5 meV for $Ni_2$ (m-dobdc), though much less than the 1.4 meV shift observed for $Fe_2$ (dobdc). Adsorption at the secondary sites also results in a significant increase in the area of the peak at 9 meV and appearance of features near 12 meV and 15 meV as a new subset of rotational levels associated with the rotationally hindered second adsorption site. Transitions in this energy range are also observed in spectra reported for higher loadings of the $M_2$ (dobdc) materials, indicating the similarity in adsorption potentials at these secondary sites.

Infrared Spectra.

Figure 22:
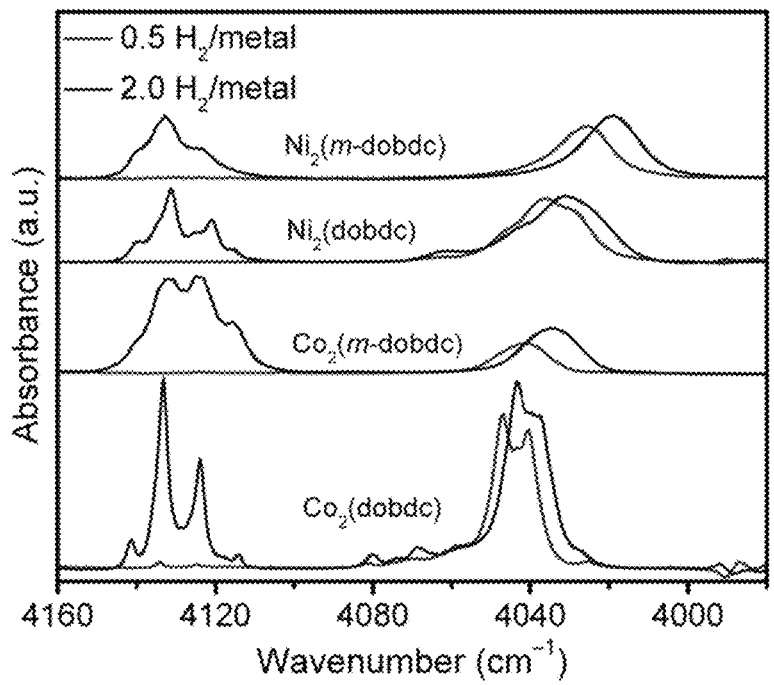
FIG. 22 presents a comparison of the IR spectra of $Ni_2$ (m-dobdc), $Ni_2$ (dobdc), $Co_2$ (m-dobdc), and $Co_2$ (dobdc) at two different concentrations. The right peak shows the $H_2$ bound to the open metal site and the left peak shows the $H_2$ bound to the secondary adsorption sites. Spectra are offset for clarity.
Figure 25:
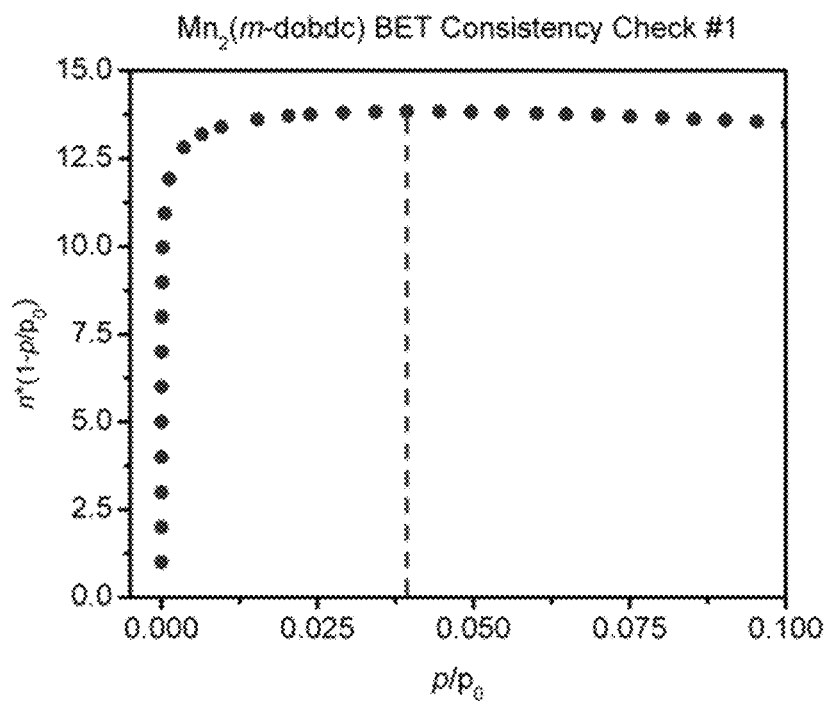
FIG. 25 provides a plot of $n*(1-p/p_0)$ vs. $p/p_0$ to determine the maximum value of $p/p_0$ that is used for fitting the BET isotherm of $Mn_2$ (m-dobdc), according to the first BET consistency criterion.
Figure 26:
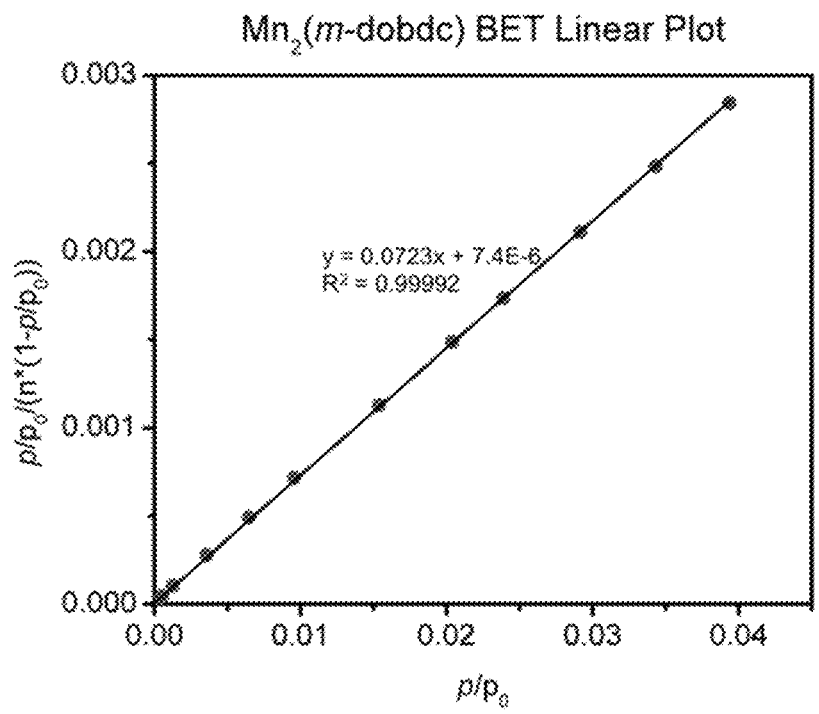
FIG. 26 provides a plot of $p/p_0/(n*(1-p/p_0))$ vs. $p/p_0$ to determine the BET surface area of $Mn_2$ (m-dobdc). The y-intercept calculated from the best fit line fulfills the second BET consistency criterion since the y-intercept is a positive value, giving a BET surface area of 1349 $m^2/g$.
Figure 27:
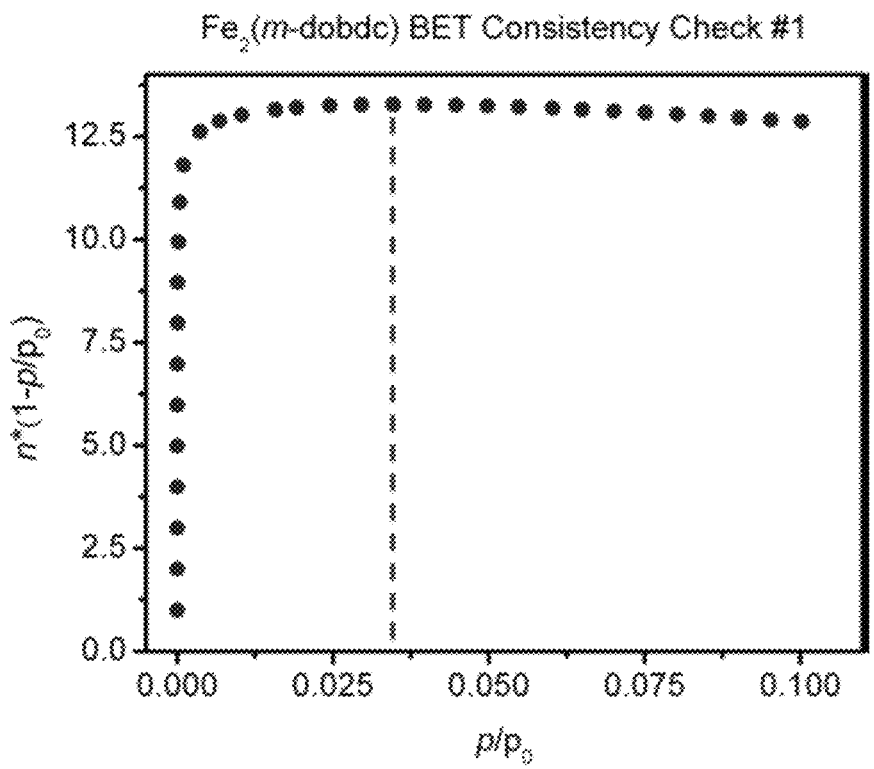
FIG. 27 provides a plot of $n*(1-p/p_0)$ vs. $p/p_0$ to determine the maximum value of $p/p_0$ that is used for fitting the BET isotherm of $Fe_2$ (m-dobdc), according to the first BET consistency criterion.
Figure 28:
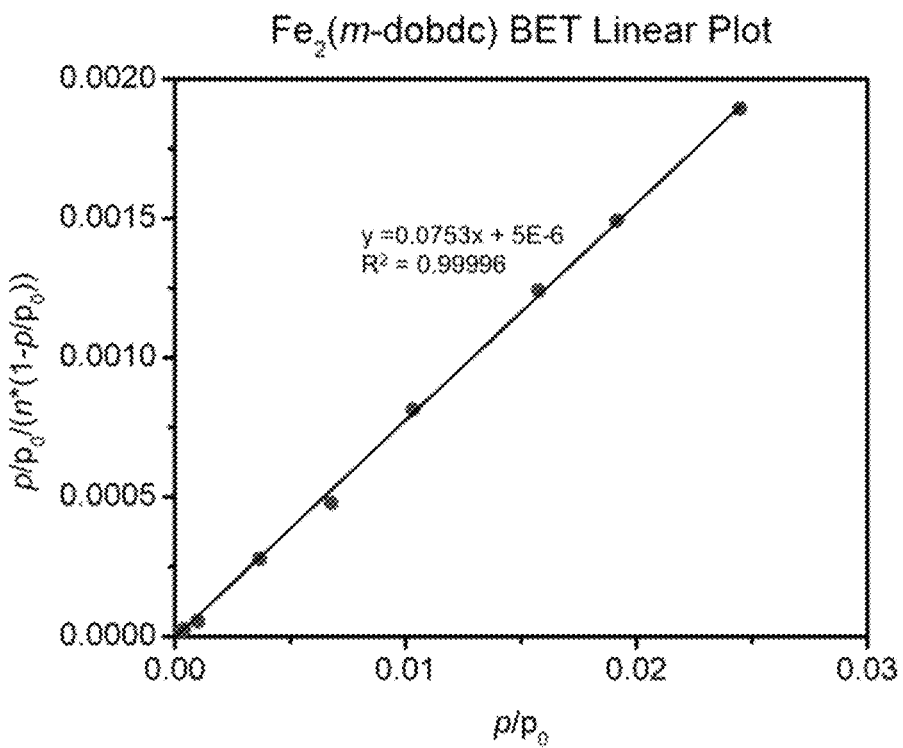
FIG. 28 provides a plot of $p/p_0/(n*(1-p/p_0))$ vs. $p/p_0$ to determine the BET surface area of $Fe_2$ (m-dobdc). The y-intercept calculated from the best fit line fulfills the second BET consistency criterion since the y-intercept is a positive value, giving a BET surface area of 1000 $m^2/g$.
Figure 29:
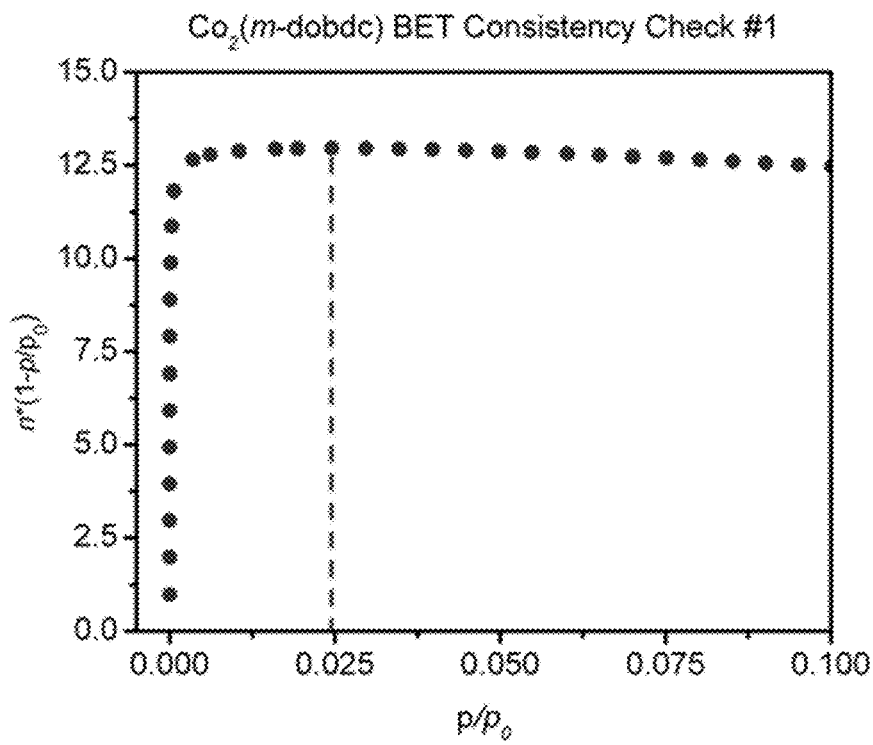
FIG. 29 provides a plot of $n*(1-p/p_0)$ vs. $p/p_0$ to determine the maximum value of $p/p_0$ that is used for fitting the BET isotherm of $Co_2$ (m-dobdc), according to the first BET consistency criterion.
Figure 30:
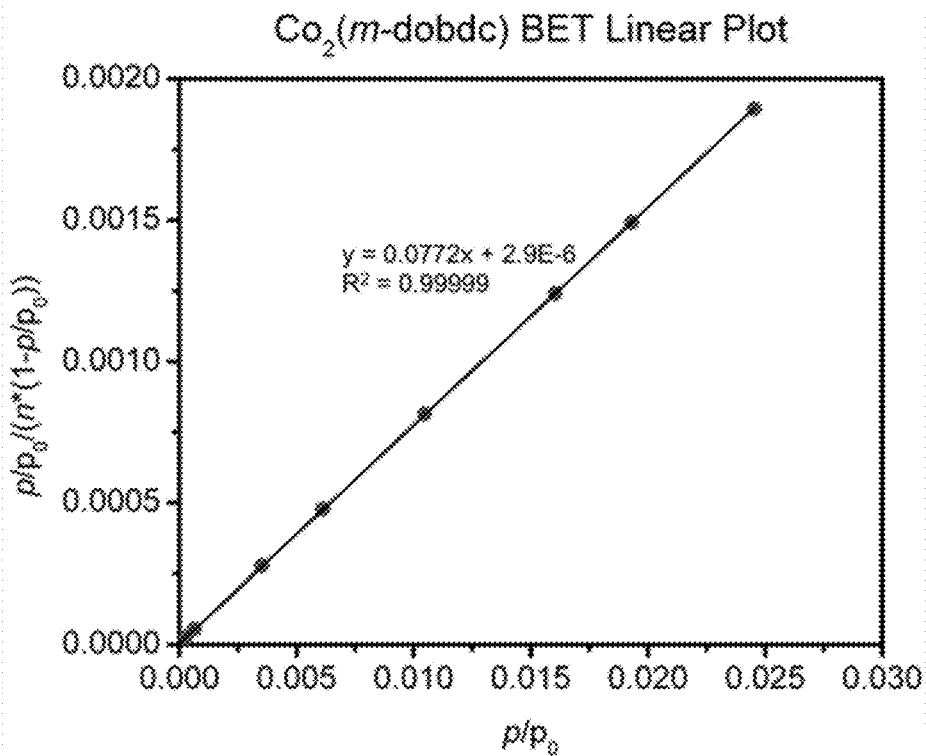
FIG. 30 provides a plot of $p/p_0/(n*(1-p/p_0))$ vs. $p/p_0$ to determine the BET surface area of $Co_2$ (m-dobdc). The y-intercept calculated from the best fit line fulfills the second BET consistency criterion since the y-intercept is a positive value, giving a BET surface area of 1264 $m^2/g$.
Figure 31:
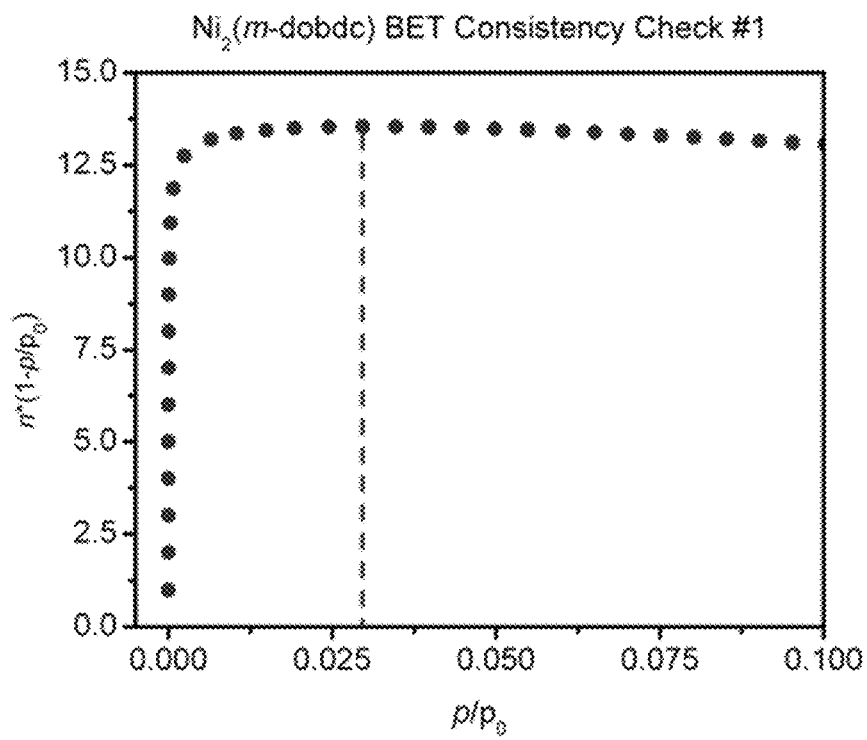
FIG. 31 provides a plot of $n*(1-p/p_0)$ vs. $p/p_0$ to determine the maximum value of $p/p_0$ that is used for fitting the BET isotherm of $Ni_2$ (m-dobdc), according to the first BET consistency criterion.
Figure 32:
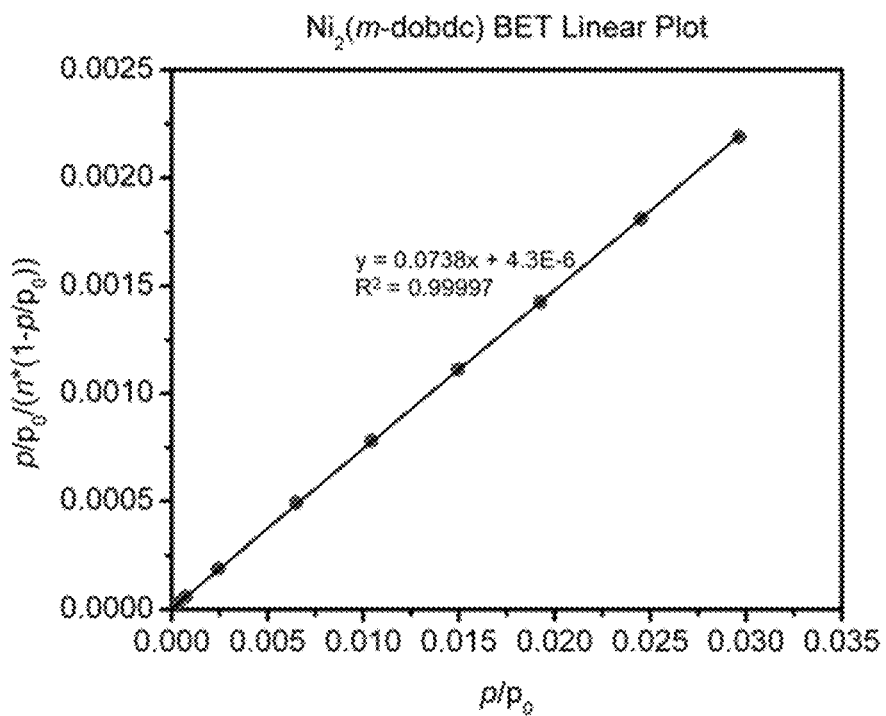
FIG. 32 provides a plot of $p/p_0/(n*(1-p/p_0))$ vs. $p/p_0$ to determine the BET surface area of $Ni_2$ (m-dobdc). The y-intercept calculated from the best fit line fulfills the second BET consistency criterion since the y-intercept is a positive value, giving a BET surface area of 1321 $m^2/g$.
Figure 33:
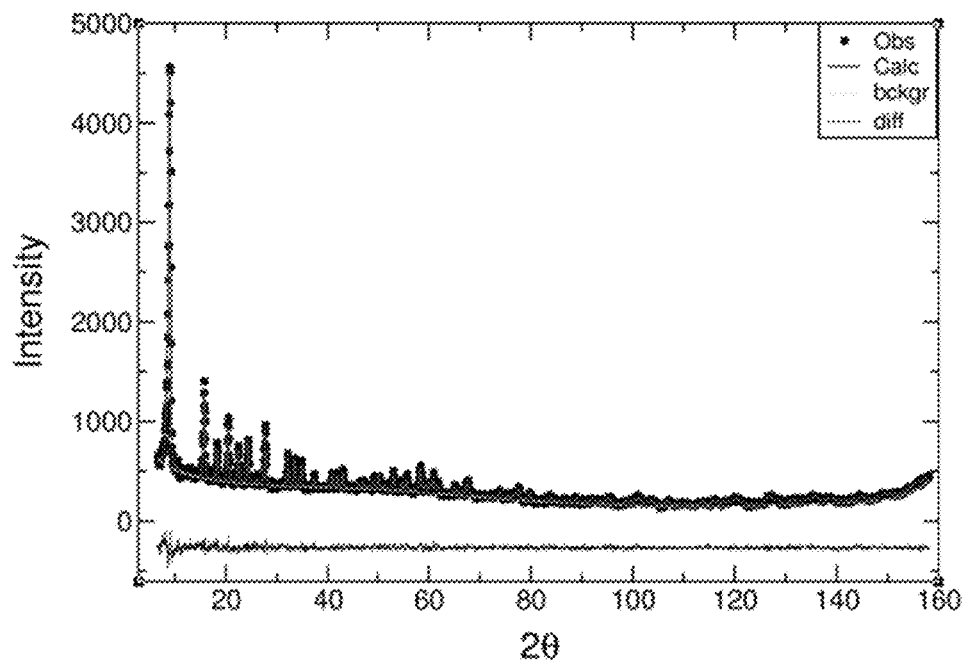
FIG. 33 provides a Rietveld refinement of the experimental neutron diffraction pattern (10 K) of $Co_2$ (m-dobdc). The calculated pattern (top trace) is in good agreement with the experimental data (circles) as evidenced by the difference pattern (bottom trace) between calculated and experimental data. Final Rietveld fit parameter was $\chi^2=0.87$.
Figure 34:
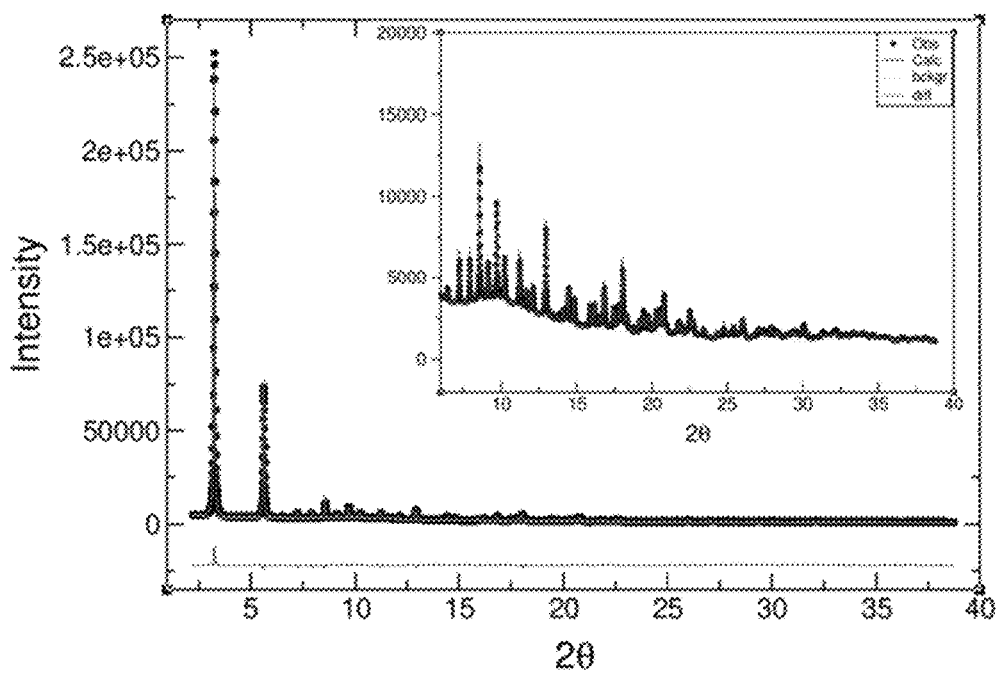
FIG. 34 provides a Rietveld refinement of the experimental synchrotron X-ray diffraction pattern (298 K) of $Co_2$ (m-dobdc). The calculated pattern (top trace) is in good agreement with the experimental data (circles) as evidenced by the difference pattern (bottom trace) between calculated and experimental data. Final Rietveld fit parameter was $\chi^2=4.505$.
Figure 35:
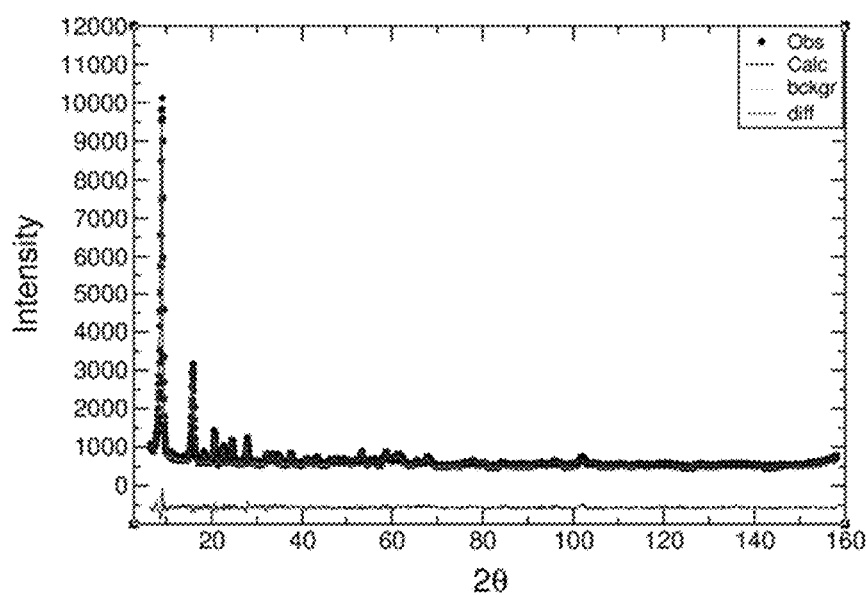
FIG. 35 provides a Rietveld refinement of the experimental neutron diffraction pattern (10 K) of $Ni_2$ (m-dobdc). The calculated pattern (top trace) is in good agreement with the experimental data (circles) as evidenced by the difference pattern (bottom trace) between calculated and experimental data. Final Rietveld fit parameter was $\chi^2=1.10$.
Figure 36:
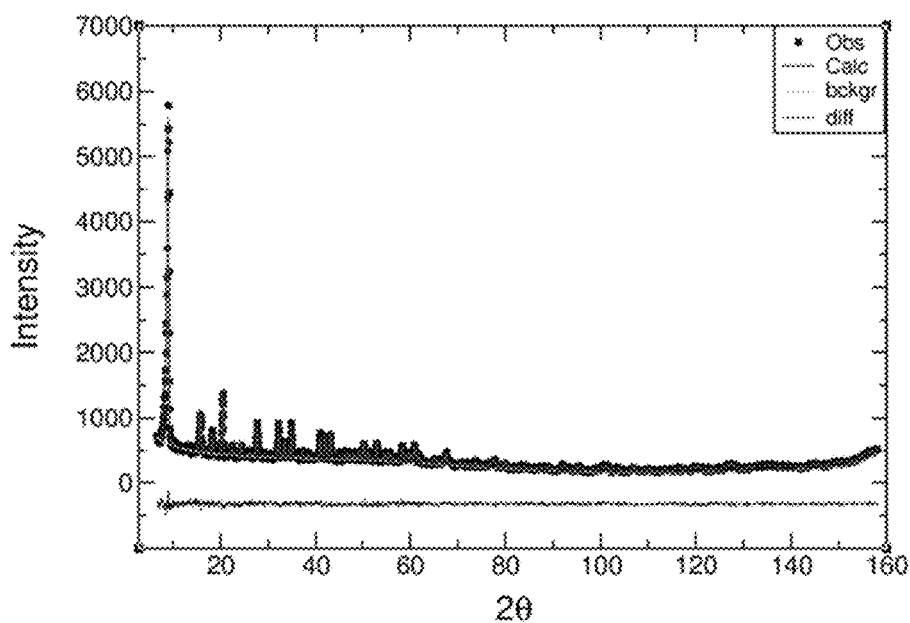
FIG. 36 provides a Rietveld refinement of the experimental neutron diffraction pattern (10 K) of $Co_2$ (m-dobdc) dosed with 0.75 $D_2$ per $Co^{2+}$ as described herein. The calculated pattern (top trace) is in good agreement with the experimental data (circles) as evidenced by the difference pattern (bottom trace) between calculated and experimental data. Final Rietveld fit parameter was $\chi^2=0.83$.
Figure 37:
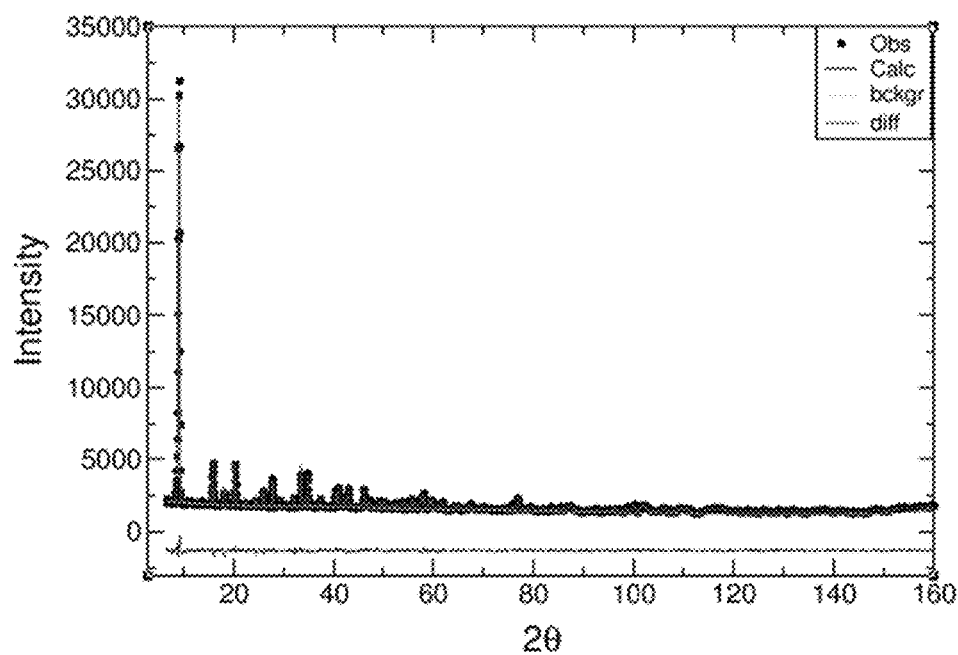
FIG. 37 provides a Rietveld refinement of the experimental neutron diffraction pattern (10 K) of $Co_2$ (dobdc) dosed with 0.75 $D_2$ per $Co^{2+}$ as described herein. The calculated pattern (top trace) is in good agreement with the experimental data (circles) as evidenced by the difference pattern (bottom trace) between calculated and experimental data. Final Rietveld fit parameter was $\chi^2=1.356$.
Figure 38:
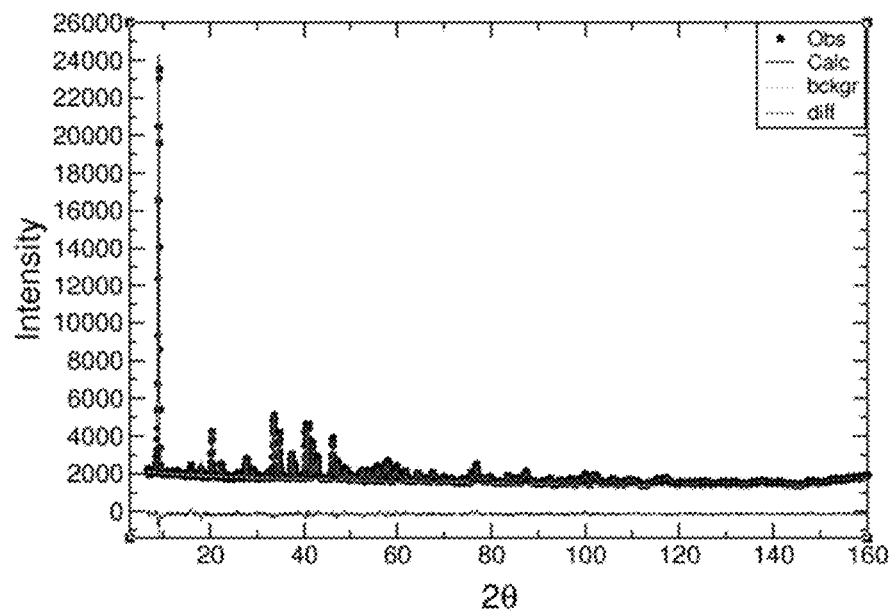
FIG. 38 provides a Rietveld refinement of the experimental neutron diffraction pattern (10 K) of $Co_2$ (dobdc) dosed with 2.25 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=1.459.
Figure 39:
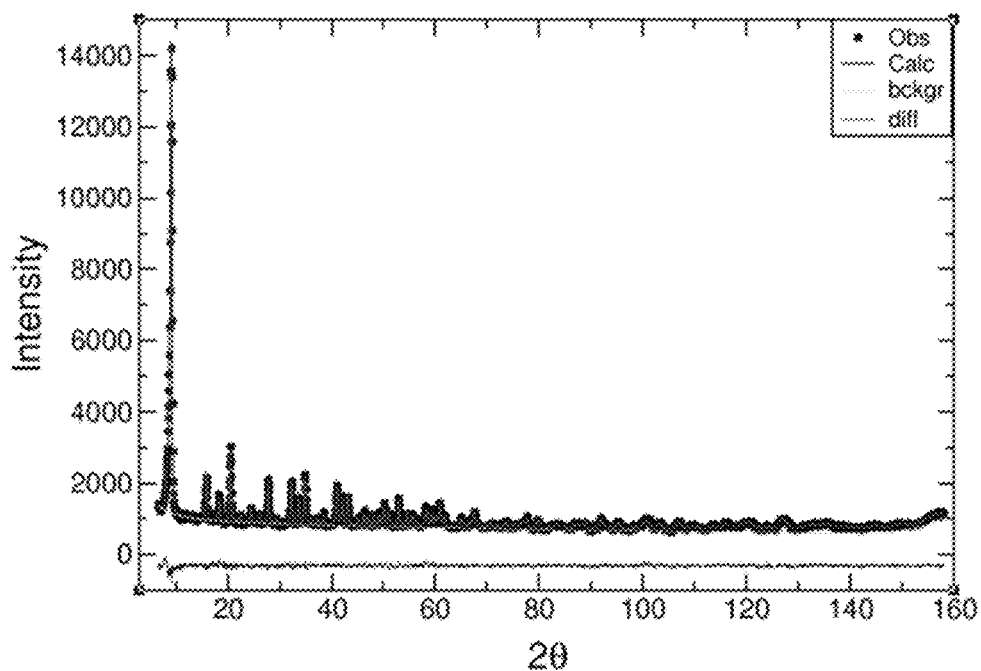
FIG. 39 provides a Rietveld refinement of the experimental neutron diffraction pattern (10 K) of Co$_2$ (m-dobdc) dosed with 1.25 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=1.123.
Figure 40:
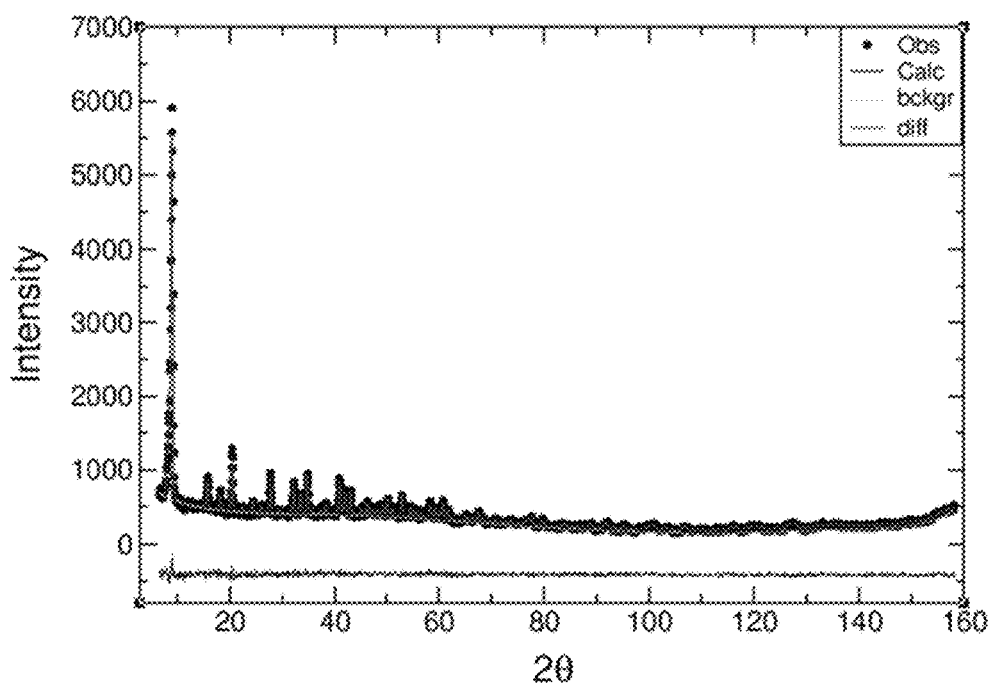
FIG. 40 provides a Rietveld refinement of the experimental neutron diffraction pattern (10 K) of Co$_2$ (m-dobdc) dosed with 1.5 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=0.889.
Figure 41:
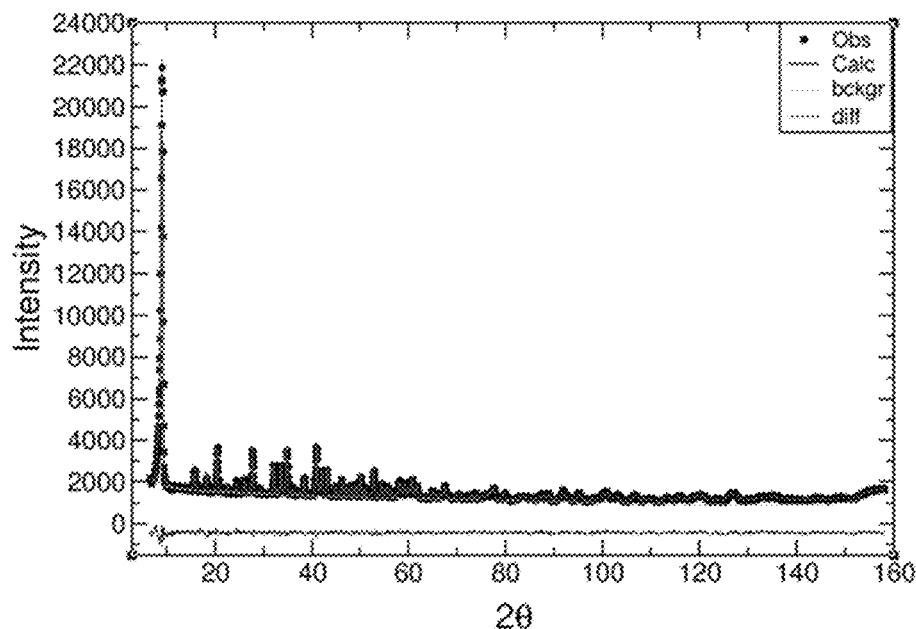
FIG. 41 provides a Rietveld refinement of the experimental neutron diffraction pattern (10 K) of Co$_2$ (m-dobdc) dosed with 1.75 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=1.351.
Figure 42:
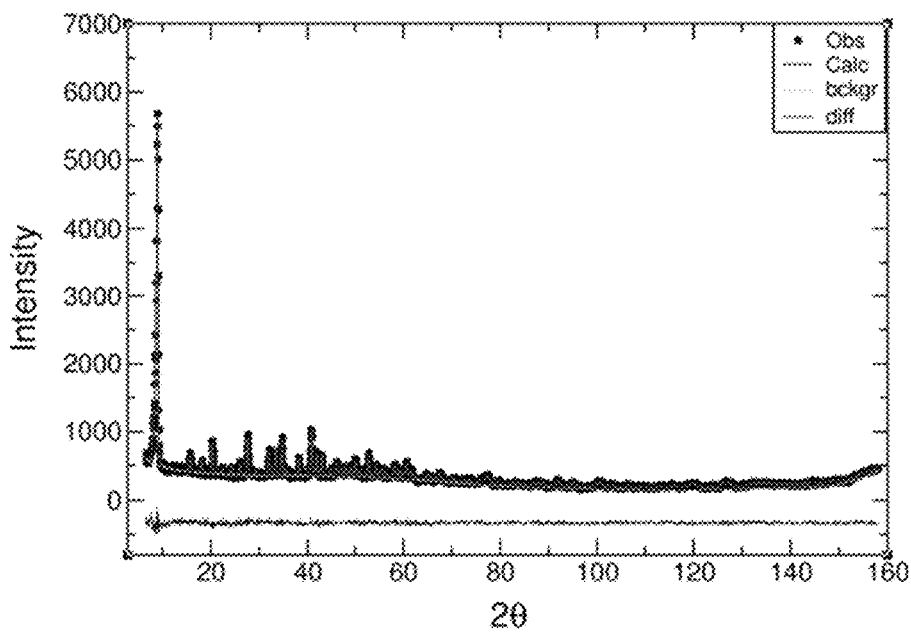
FIG. 42 provides a Rietveld refinement of the experimental neutron diffraction pattern (10 K) of Co$_2$ (m-dobdc) dosed with 2.0 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=0.84.
Figure 43:
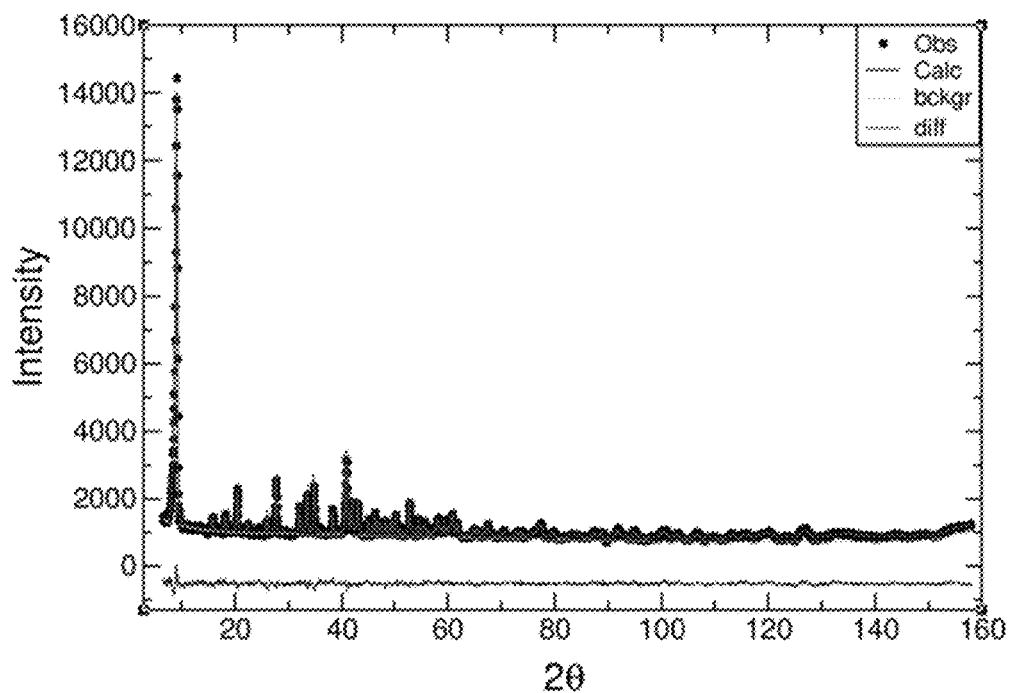
FIG. 43 provides a Rietveld refinement of the experimental neutron diffraction pattern (10 K) of Co$_2$ (m-dobdc) dosed with 2.25 D$_2$ per Co$^{2+}$ as described in the text. The calculated pattern (top trace) is in good agreement with the experimental data (circles) as evidenced by the difference pattern (bottom trace) between calculated and experimental data. Final Rietveld fit parameter was $\chi^2$=1.149.
Figure 44:
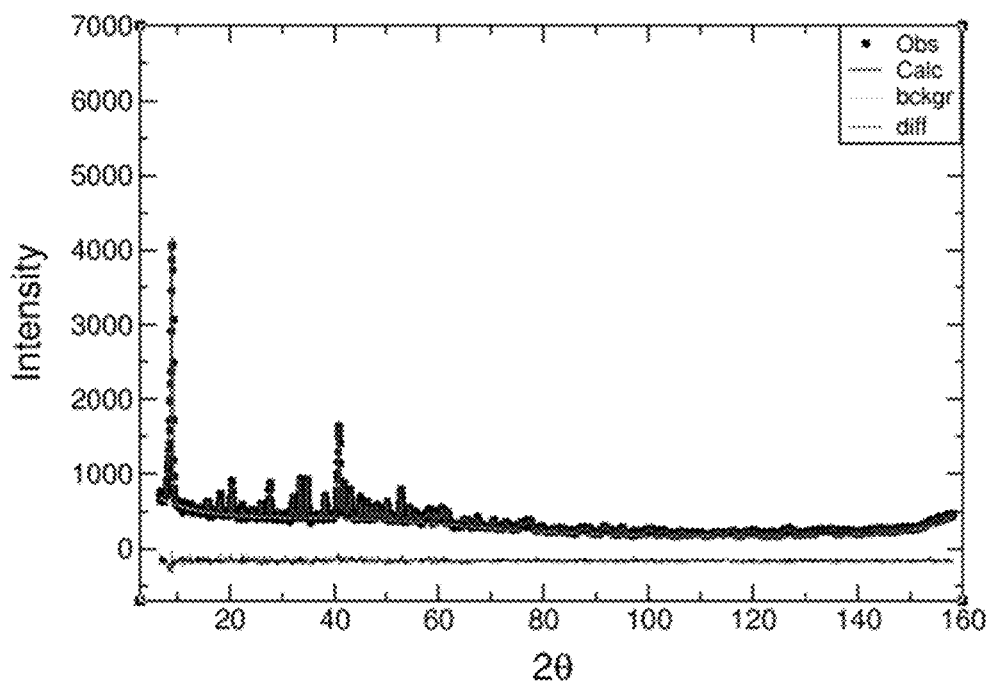
FIG. 44 provides a Rietveld refinement of the experimental neutron diffraction pattern (10 K) of Co$_2$ (m-dobdc) dosed with 3.0 D$_2$ per Co$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=0.873.
Figure 45:
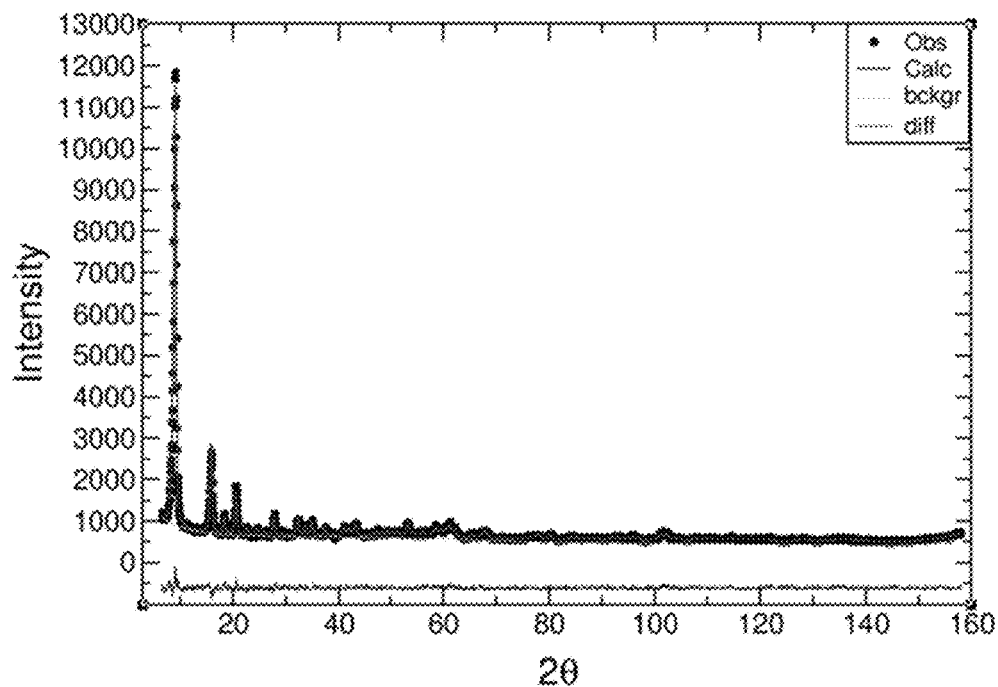
FIG. 45 provides a Rietveld refinement of the experimental neutron diffraction pattern (10 K) of Ni$_2$ (m-dobdc) dosed with 1.0 D$_2$ per Ni$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=0.998.
Figure 46:
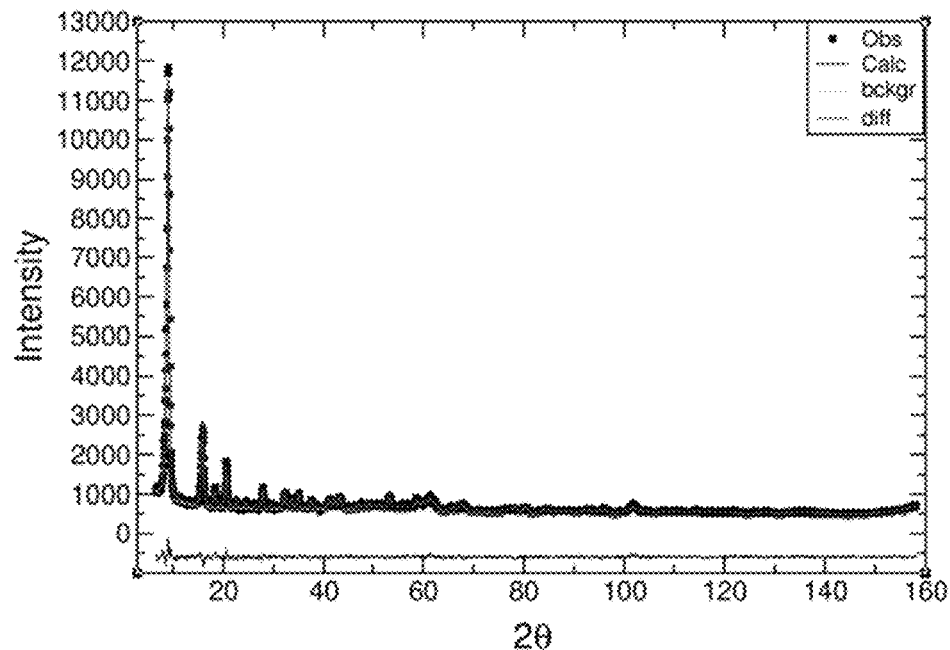
FIG. 46 provides a Rietveld refinement of the experimental neutron diffraction pattern (10 K) of Ni$_2$ (m-dobdc) dosed with 2.0 D$_2$ per Ni$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=1.676.
Figure 47:
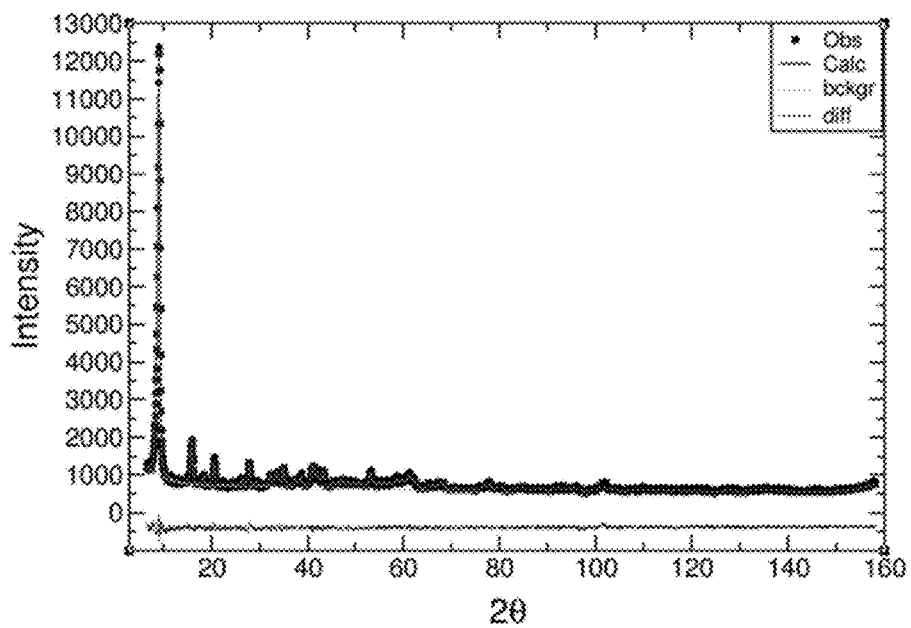
FIG. 47 provides a Rietveld refinement of the experimental neutron diffraction pattern (10 K) of Ni$_2$ (m-dobdc) dosed with 3.0 D$_2$ per Ni$^{2+}$ as described herein. The calculated pattern (top trace) is in good agreement with the experimental data (circles) as evidenced by the difference pattern (bottom trace) between calculated and experimental data. Final Rietveld fit parameter was $\chi^2$=1.545.
Figure 48:
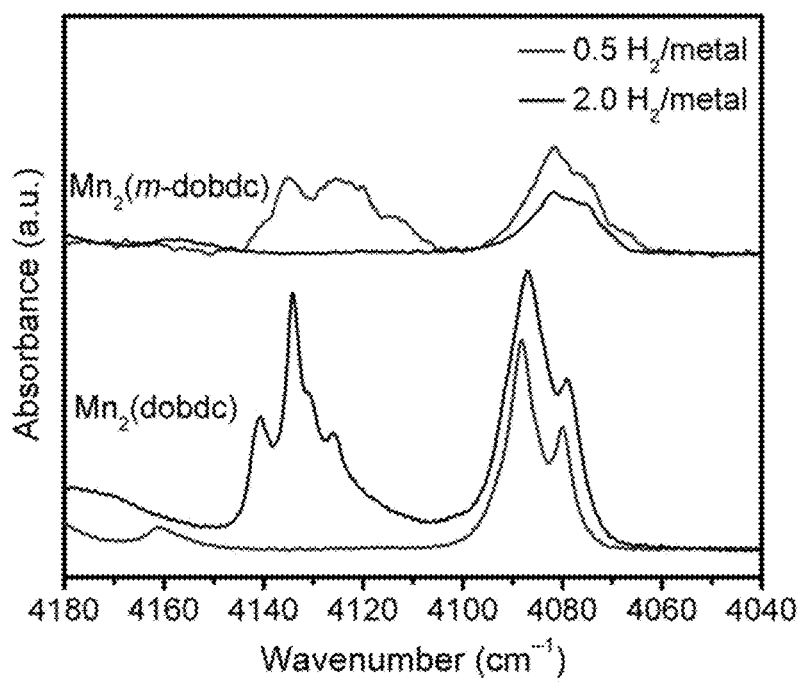
FIG. 48 presents a comparison of the IR spectra of Mn$_2$ (m-dobdc) and Mn$_2$ (dobdc) at different concentrations. The slight shift in the peak around 4080 to lower frequency in Mn$_2$ (m-dobdc) is indicative of a more strongly bound H$_2$ to the open metal center. Spectra are offset for clarity.
Figure 49:
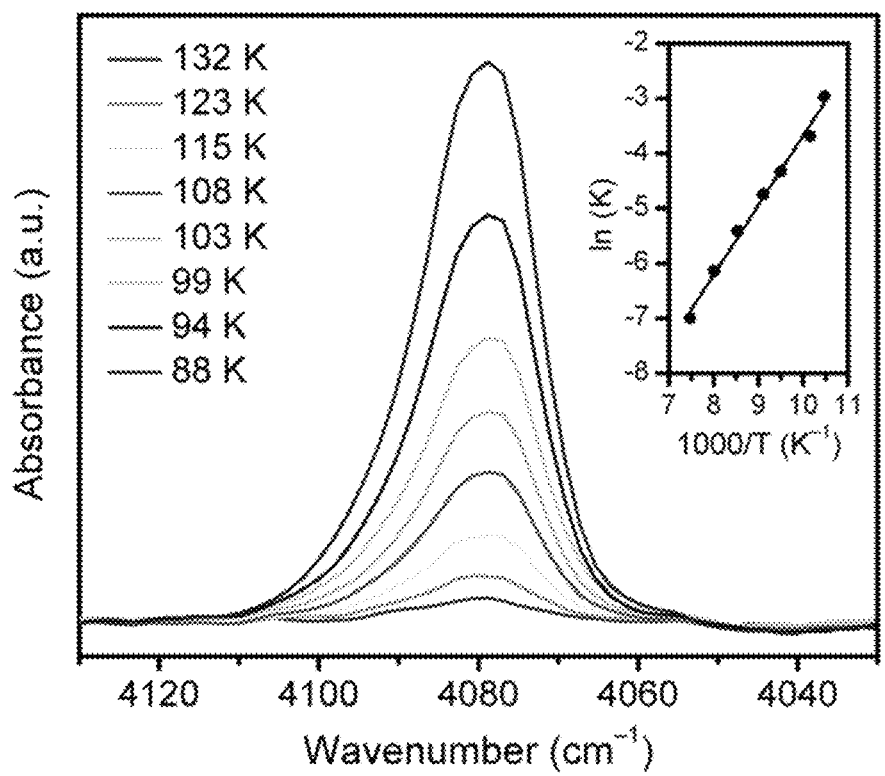
FIG. 49 provides a variable temperature infrared spectrum of Mn$_2$ (m-dobdc). The inset shows the van't Hoff relationship plot that is used to extract the enthalpy and entropy change in H$_2$ upon adsorption. Lines go from 88K (top) to 132K (bottom).
Figure 50:
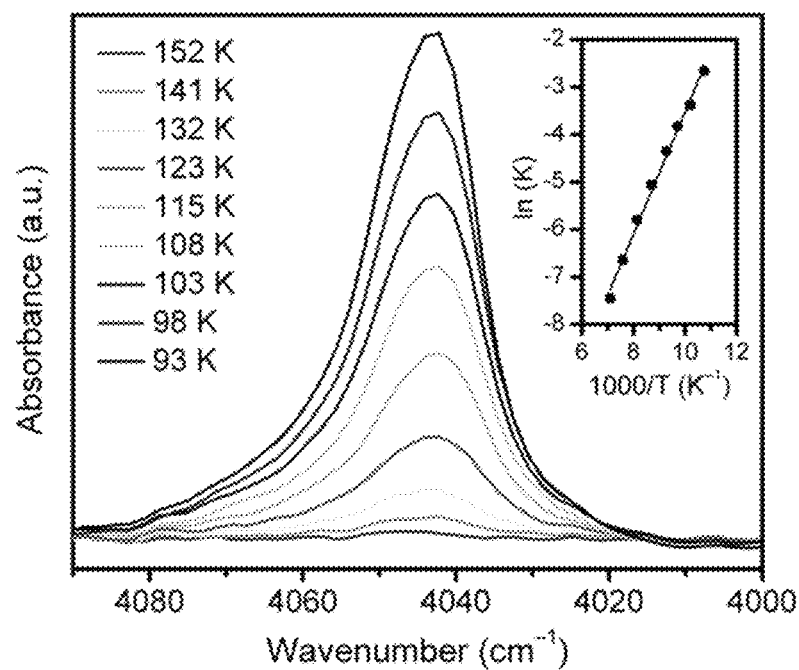
FIG. 50 provides a variable temperature infrared spectrum of Co$_2$ (dobdc). The inset shows the van't Hoff relationship plot that is used to extract the enthalpy and entropy change in H$_2$ upon adsorption. Lines go from 93K (top) to 152K (bottom).
Figure 51:
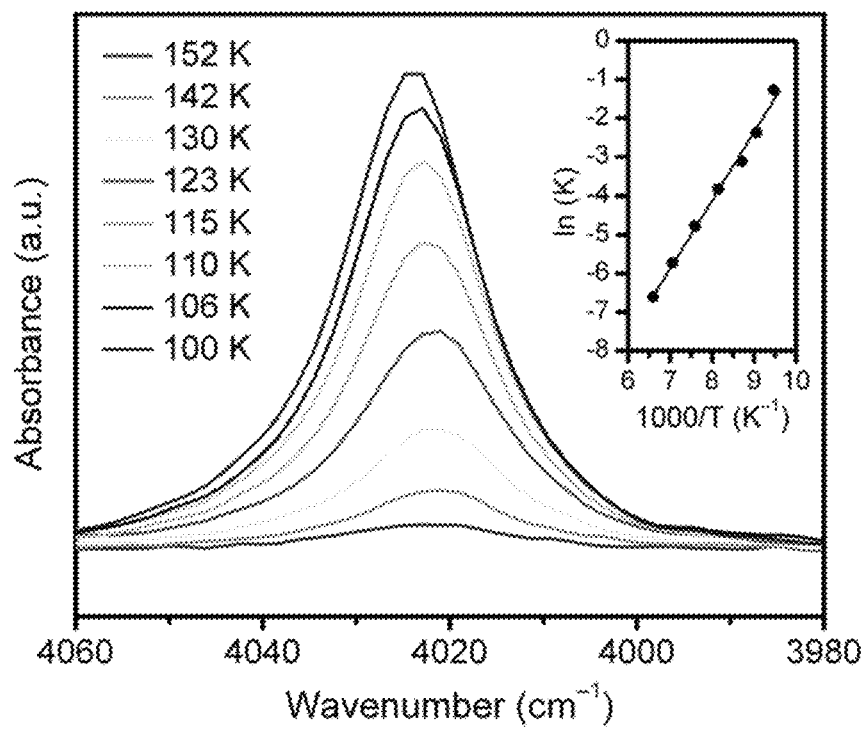
FIG. 51 provides a variable temperature infrared spectrum of Ni$_2$ (m-dobdc). The inset shows the van't Hoff relationship plot that is used to extract the enthalpy and entropy change in H$_2$ upon adsorption. Lines go from 100K (top) to 152K (bottom).
Figure 52:
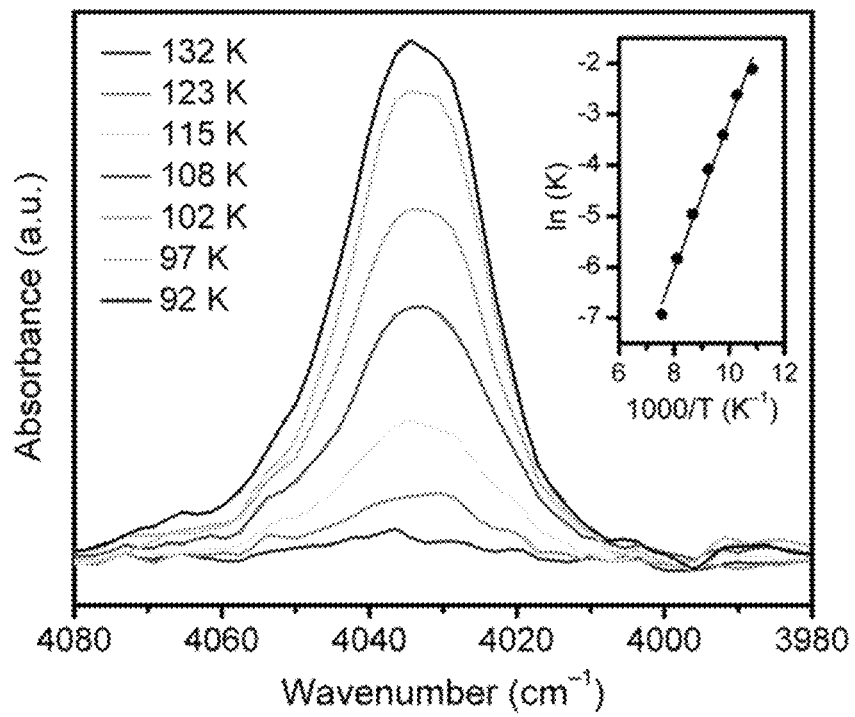
FIG. 52 provides a variable temperature infrared spectrum of Ni$_2$ (dobdc). The inset shows the van't Hoff relationship plot that is used to extract the enthalpy and entropy change in H$_2$ upon adsorption. Lines go from 92 (top) to 132K (bottom).
Figure 53:
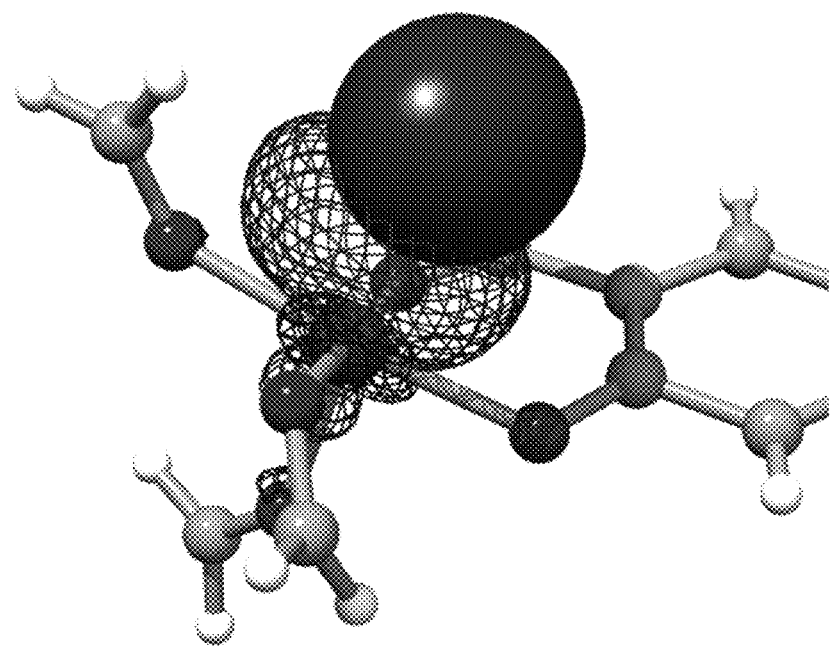
FIG. 53 illustrates the occupied and virtual orbitals, shown as solid and mesh, respectively, for the forward bonding pair COVP 1 (TABLE 26) for the dobdc complex.
Figure 54:
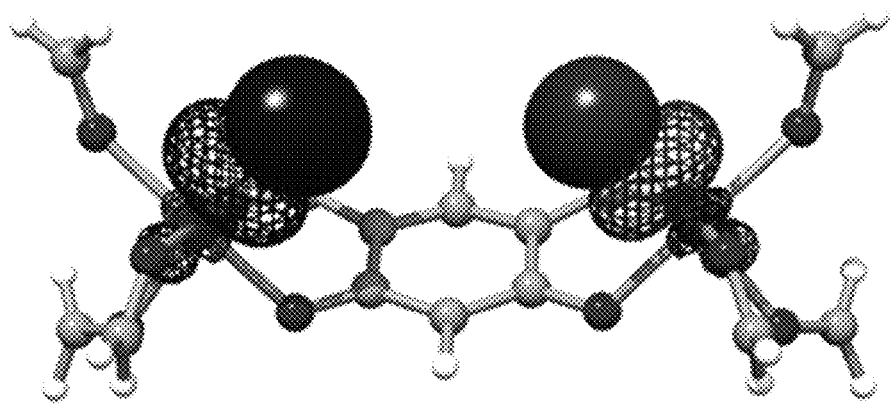
FIG. 54 illustrates the occupied and virtual orbitals, shown as solid and mesh, respectively, for the forward bonding pair COVP 1 (TABLE 26) for the m-dobdc complex.
Figure 55:
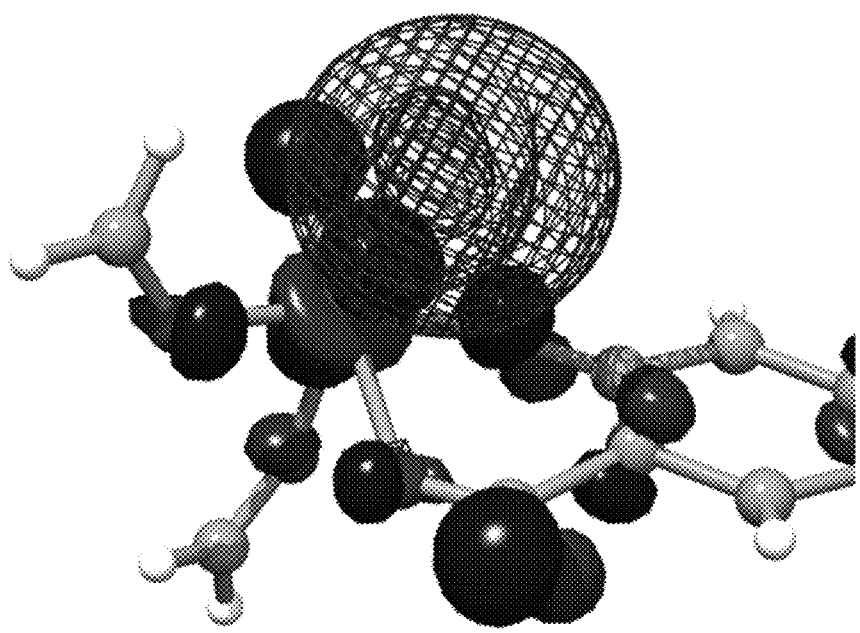
FIG. 55 illustrates the occupied and virtual orbitals, shown as solid and mesh, respectively, for the backbonding pair COVP 1 (TABLE 26) for the dobdc complex.
Figure 56:
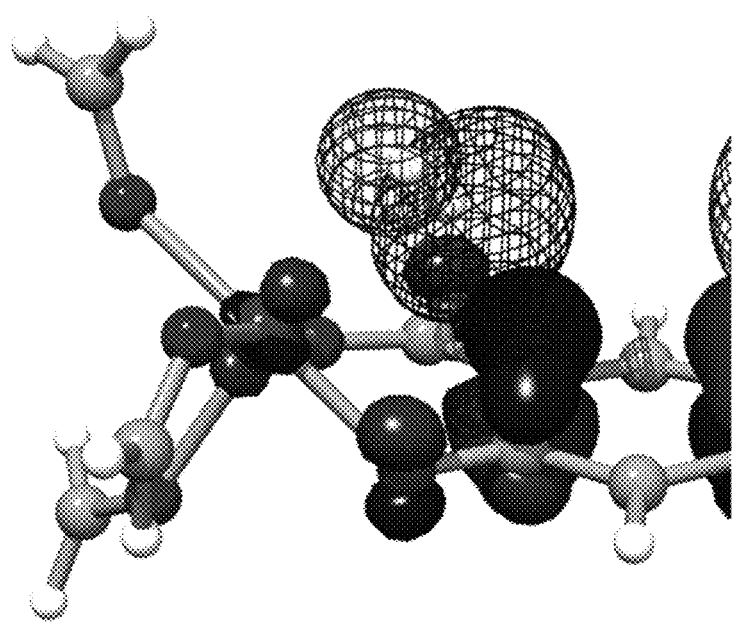
FIG. 56 illustrates the occupied and virtual orbitals, shown as solid and mesh, respectively, for the backbonding pair COVP 1 (TABLE 26) for the m-dobdc complex.
Figure 57:
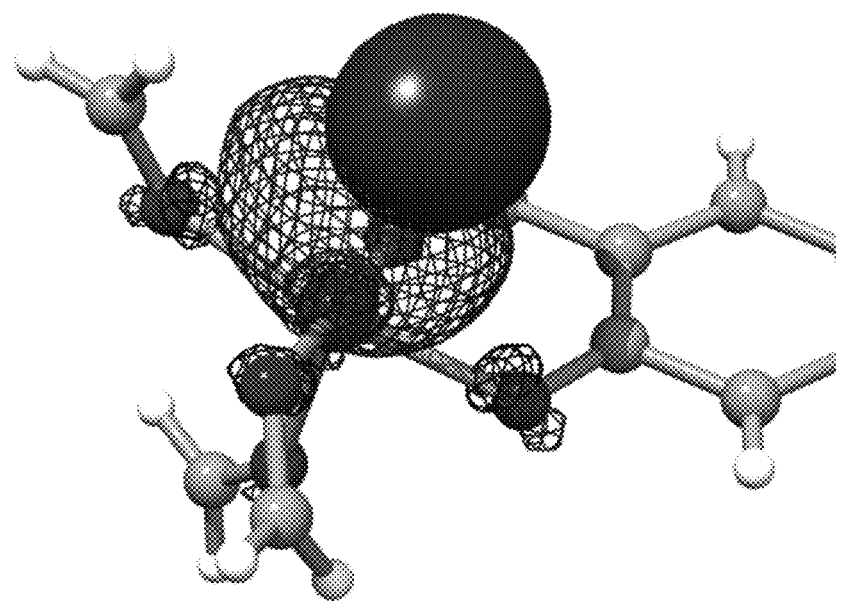
FIG. 57 illustrates the occupied and virtual orbitals, shown as solid and mesh, respectively, for the forward bonding pair COVP 2 (TABLE 26) for the dobdc complex
Figure 58:
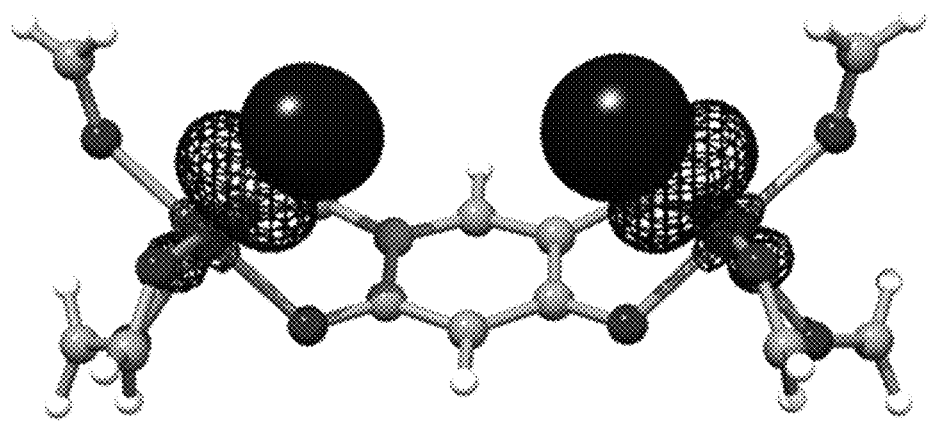
FIG. 58 illustrates the occupied and virtual orbitals, shown as solid and mesh, respectively, for the forward bonding pair COVP 2 (TABLE 26) for the m-dobdc complex.
Figure 59:
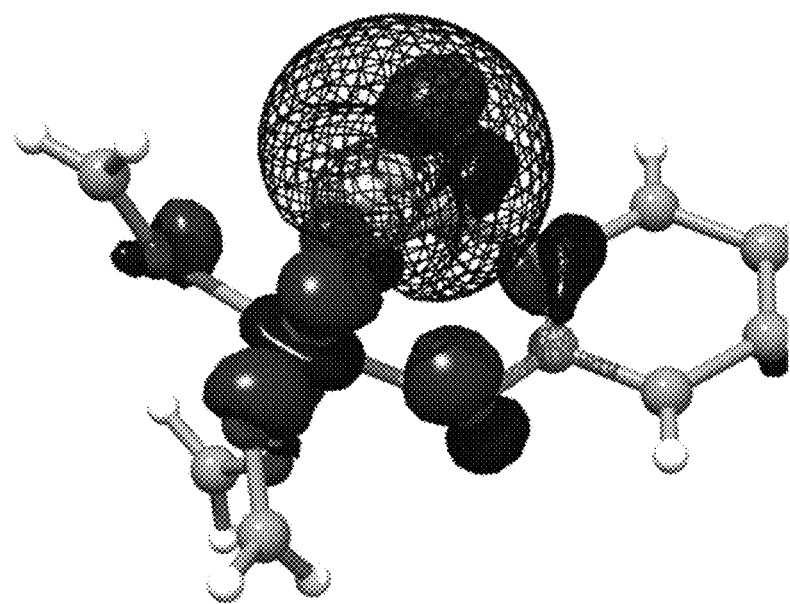
FIG. 59 illustrates the occupied and virtual orbitals, shown as solid and mesh, respectively, for the backbonding pair COVP 2 (TABLE 26) for the dobdc complex.
Figure 60:
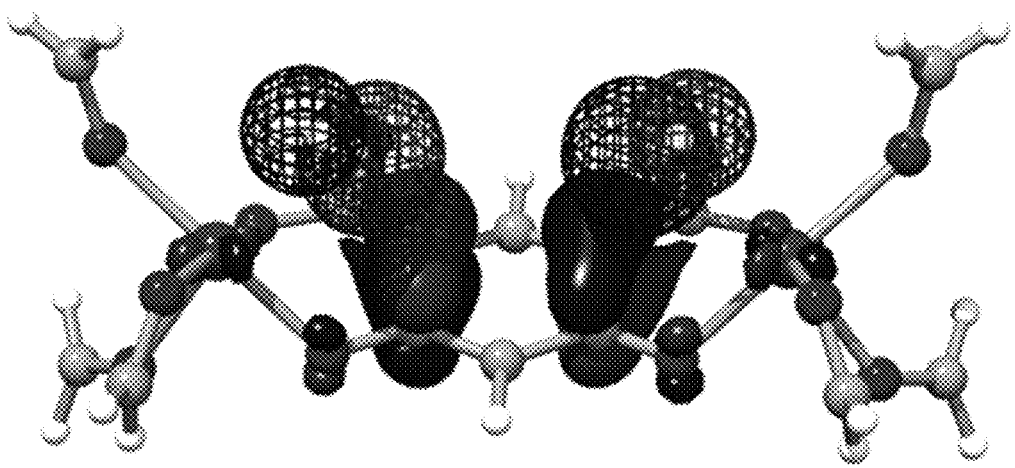
FIG. 60 illustrates the occupied and virtual orbitals, shown as solid and mesh, respectively, for the backbonding pair COVP 2 (TABLE 26) for the m-dobdc complex.
Figure 61:
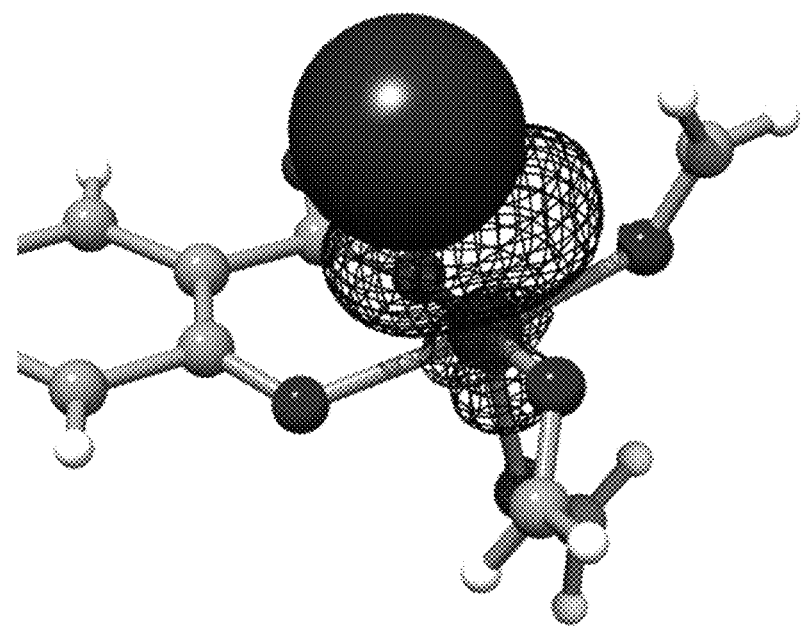
FIG. 61 illustrates the occupied and virtual orbitals, shown as solid and mesh, respectively, for the forward bonding pair COVP 3 (TABLE 26) for the dobdc complex.
Figure 62:
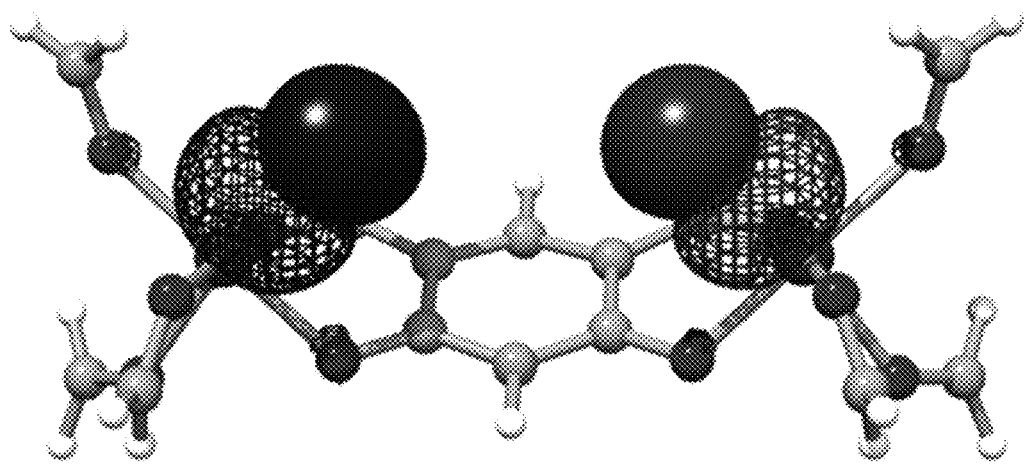
FIG. 62 illustrates the occupied and virtual orbitals, shown as solid and mesh, respectively, for the forward bonding pair COVP 3 (TABLE 26) for the m-dobdc complex.
Figure 63:
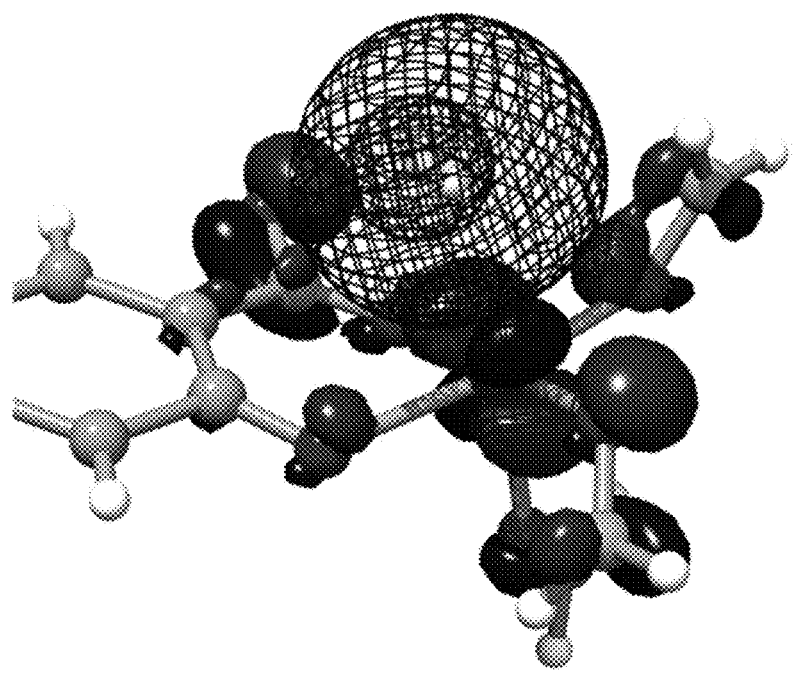
FIG. 63 illustrates the occupied and virtual orbitals, shown as solid and mesh, respectively, for the backbonding pair COVP 3 (TABLE 26) for the dobdc complex.
Figure 64:
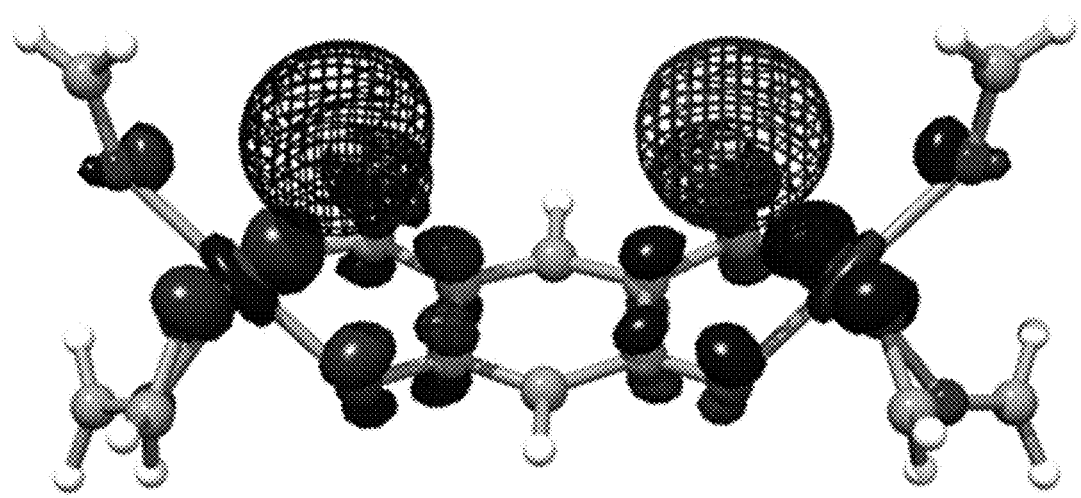
FIG. 64 illustrates the occupied and virtual orbitals, shown as solid and mesh, respectively, for the backbonding pair COVP 3 (TABLE 26) for the m-dobdc complex.
Figure 65:
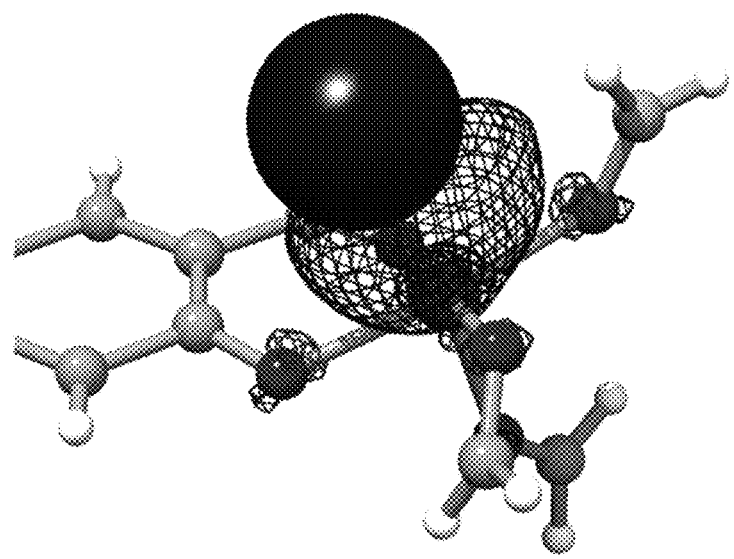
FIG. 65 illustrates the occupied and virtual orbitals, shown as solid and mesh, respectively, for the forward bonding pair COVP 4 (TABLE 26) for the dobdc complex.
Figure 66:
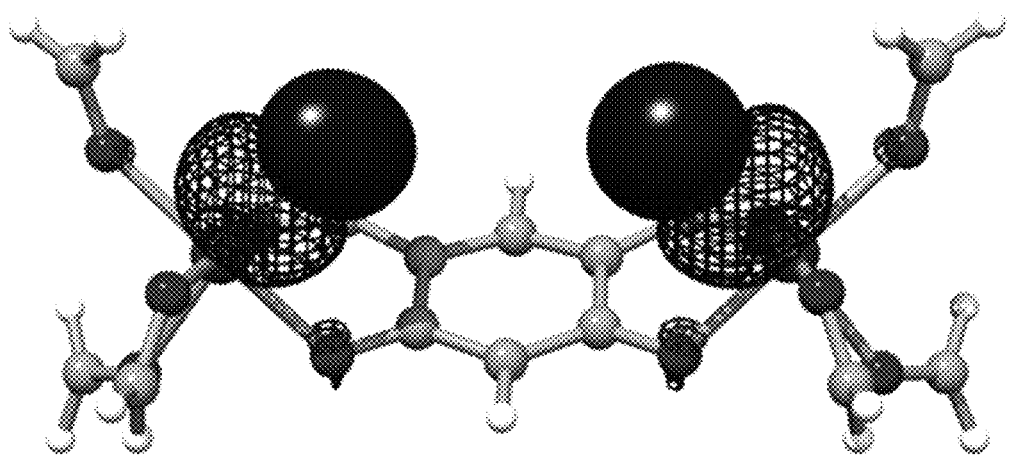
FIG. 66 illustrates the occupied and virtual orbitals, shown as solid and mesh, respectively, for the forward bonding pair COVP 4 (TABLE 26) for the m-dobdc complex.

The behavior of adsorbed hydrogen was further probed through infrared spectroscopy. The vibrational frequency of adsorbed hydrogen is almost always lower than that of the gas phase (4161 $cm^{-1}$), and it is now well established that for metal-organic framework materials, there is a strong correlation between the magnitude of the frequency shift and the binding energy at a particular site see e.g. Fitzgerald et al. (J. Am. Chem. Soc. 133:20310 (2011)). FIG. 22 shows the comparison of the $H_2$ vibrational frequency at two different concentrations for $Ni_2$ (m-dobdc), $Ni_2$ (dobdc), $Co_2$ (m-dobdc), and $Co_2$ (dobdc) and in $Mn_2$ (m-dobdc) and $Mn_2$ (dobdc) in FIG. 48. At this temperature, the pure vibrational part of the spectrum consists of an ortho-para pair that is separated by just 6 $cm^{-1}$ in the gas phase. The peak near 4025 $cm^{-1}$ in each spectrum corresponds to the $H_2$ bound to the open metal site. In each case, the lower concentration spectra, which are known to arise purely from $H_2$ bound to the open metal site, show a greater frequency shift for the $Co_2$ (m-dobdc) and $Ni_2$ (m-dobdc) than the corresponding $Co_2$ (dobdc) and $Ni_2$ (dobdc). This shift is consistent with the greater binding energy seen in the $M_2$ (m-dobdc) frameworks based on equilibrium adsorption isotherms and neutron diffraction studies. Upon further loading, the secondary sites seen in neutron diffraction begin to be populated, which is evidenced by the second peak that grows in around 4125 $cm^{-1}$. The energy of these peaks associated with the secondary sites is very similar to those seen for $M_2$ (dobdc); INS transitions for $H_2$ bound to the secondary sites in $M_2$ (m-dobdc) and $M_2$ (dobdc) are also similar. This supports the hypothesis that the electronics around the metal are altered with the m-dobdc linker, leading to a higher initial isosteric heat of adsorption, but the secondary sites in $M_2$ (m-dobdc) and $M_2$ (dobdc) are similar in binding potential. The secondary site peaks are also generally broader in $M_2$ (m-dobdc). Furthermore, a consistent shift in the frequency of the open metal bands as a function of concentration is seen for both the $Co_2$ (m-dobdc) and $Ni_2$ (m-dobdc) samples, although not to the same degree in the $Mn_2$ (m-dobdc) sample. These concentration shifts have previously been attributed to $H_2$—$H_2$ interactions; it is interesting to note that these shifts seem largely unaffected by the change in linker. Furthermore, these shifts correlate well with the shifts seen in rotational potential as the secondary binding sites are populated in the inelastic neutron scattering data in FIG. 21.

Variable temperature infrared spectroscopy is a standard technique for establishing the enthalpy of adsorption at a particular site. FIG. 23 shows the spectra obtained for $H_2$ in $Co_2$ (m-dobdc) while lowering the sample temperature from 142 to 75 K. The data obtained for $Mn_2$ (m-dobdc), $Ni_2$ (m-dobdc), $Co_2$ (dobdc), and $Ni_2$ (dobdc) are seen in FIGS. 49-52. In each case, the initial $H_2$ pressure in the system is set such that only the open metal site is occupied over this temperature range. The fractional occupancy is then determined by the ratio of the area under the IR band to that at complete saturation. The inset in FIG. 23 shows the van't Hoff relationship plot used to extract both the enthalpy and entropy change upon adsorption. The data obtained in this way for the different materials is summarized in TABLE 23.

TABLE 23

Enthalpy and entropy changes upon adsorption of $H_2$ to the open metal site. Values are extracted from a van't Hoff plot based on the area of the infrared vibrational peaks for a given temperature and pressure.

| | $M_2$ (dobdc) | | $M_2$ (m-dobdc) | |
|---|---|---|---|---|
| Metal | ΔS (J/mol K) | ΔH (kJ/mol) | ΔS (J/mol K) | ΔH (kJ/mol) |
| Mn | — | — | −135 | −10.5 |
| Co | −136 | −10.7 | −147 | −12.1 |
| Ni | −148 | −12.3 | −147 | −13.7 |

The slopes extracted from the van't Hoff plots are sensitive to small variations in the maximum saturation area; as such, an error on the order of 0.5 kJ/mol is estimated. Given these limitations, it is still apparent that the data is consistent with the calculated isosteric heats of adsorption from the $H_2$ adsorption isotherms showing an enthalpy increase from Mn to Co to Ni. More importantly, these infrared heat of adsorption values are about 1.4 kJ/mol higher than those for their respective $M_2$ (dobdc) counterparts, which is consistent with the trends observed using values calculated from $H_2$ adsorption isotherms. It was also noted that the measured large entropy changes are consistent with the literature, who observed a strong correlation between the enthalpy and entropy change of the bound hydrogen in different metal-organic frameworks. Overall, the redshift seen in the IR spectra of the adsorbed $H_2$ in $M_2$ (m-dobdc) as compared to $M_2$ (dobdc) indicates that the $H_2$ is more strongly bound and the VTIR data confirms the increased binding enthalpies seen from the $H_2$ adsorption data.

DFT Calculations.

Density functional theory (DFT) was used to examine the differences in electronics around the metal atoms in systems modeling that of $M_2$ (dobdc) and $M_2$ (m-dobdc). DFT has shown itself to be a fairly robust method for modeling chemical systems. DFT's major failings, self-interaction error and lack of dispersion interactions, are well-known in Perdew et al. (*Phys. Rev. B* 23:5048 (1981)), Kristyán et al. (*Chem. Phys. Lett.* 229:175 (1994)), and Dutoi et al. (*Chem. Phys. Lett.* 422:230 (2006)) and allow for functionals to be developed with corrections accounting for them, namely range-separation and explicit dispersion correction. Previously, the ωB97X-D functional in Chai et al. (*Phys. Chem. Chem. Phys.* 10:6615 (2008)) was shown in Sumida et al. (*J. Am. Chem. Soc.* 135:1083 (2013)) to accurately model hydrogen binding in metal-organic frameworks.

Accurately modeling $M_2$ (dobdc)-type frameworks with electronic structure theory is a significant challenge; fragmenting the structure at any point will lead to the neglect of important interactions due to the chains formed by the M atoms. In an attempt to parse out the nature of the difference of the dobdc and m-dobdc linkers' effect on hydrogen binding, some of the description of the absolute energetics will be sacrificed while still getting relevant information about the relative systems. In this vein, modeling is focused on the linker of interest coordinated to two Co atoms; the remaining ligands on each Co atom are truncated as formaldehyde molecules in order to maintain charge balance. After choosing these model molecules, the geometry of the system must be determined. Since the key open site on each Co atom in the framework is enforced by constraints on the ligands imposed by the macrostructure of the framework, which cannot be explicitly included in the model, since an internally optimized geometry of the model will not actually have the structural properties of the framework in question. Thus, the geometry of the linker complex is taken from the experimentally determined crystal structure of the framework and subsequently frozen before interaction with $H_2$ is optimized. Furthermore, the $H_2$—Co distance is taken from the neutron diffraction spectra to ensure an accurate depiction of this interaction in the model system.

The first sign of distinction between the two isomers is seen in the geometry with which $H_2$ binds to the Co. In the dobdc linker complex, the hydrogen binds to create a nearly octahedral geometry around the Co, with a distance of 3.30 Å from the $H_2$ to the aromatic carbon bonded to the carboxylate (the alpha carbon). Conversely, in the m-dobdc complex, the $H_2$ is reoriented toward the linker at a distance of 2.64 Å from the alpha carbon (see FIG. 24A-B). This difference in orientation suggests that the interaction with the linker may have a direct impact on the binding of $H_2$ in the m-dobdc complex.

While comparing absolute energy differences gives a single number to describe bonding, energy decomposition analysis (EDA) breaks down that one number into physically interpretable components. A proposed EDA based on absolutely localized molecular orbitals (ALMOs) breaks down total binding energies into frozen energies, polarization, and charge transfer components. The frozen term is due to permanent electrostatics and is repulsive since the $H_2$ electron density is being brought within the van der Waals radius of the Co. The polarization term corresponds to the favorable interaction of electrons in the $H_2$ and complex fragments relaxing to the presence of the other fragment without electron transfer. Charge transfer stems from energy lowering when electrons are allowed to relax from one fragment to the other. A recent generalization of ALMO EDA to open-shell molecules allows for the application of this method to general metal-containing systems. The binding energy decomposition analysis clarifies the differences in these two complexes. TABLE 24 shows the components of the ALMO EDA.

TABLE 24

ALMO energy decomposition analysis of $H_2$ binding to the dobdc and m-dobdc complexes.

| | Energy (kJ/mol) | |
|---|---|---|
| Component | dobdc complex | m-dobdc complex |
| Frozen | 1.3 | 7.9 |
| Polarization | −4.8 | −9.5 |
| Charge Transfer | −12.5 | −17.1 |
| Total | −16.0 | −18.6 |

There is more charge transfer and polarization in the m-dobdc complex, but it is partly offset by the increase in the energetically unfavorable frozen term. This larger frozen term is the result of the increased steric repulsion that stems from a shorter $H_2$—Co distance in the m-dobdc complex. While a shorter $H_2$—Co distance increases both charge transfer and polarization, the doubling of the polarization term as compared with the dobdc complex cannot be fully described by this bond shortening; the hydrogen binding in the m-dobdc complex is further strengthened by the interaction with the linker as seen by the reorientation of the hydrogen toward the benzene alpha carbon. Thus, differences in charge transfer are mostly offset by changes to the frozen term, while the increase in polarization shows the effect that the environment created by the linker has on the binding energies; a more polarized $H_2$ molecule results in a stronger interaction with the Co atom.

The orbital interactions between $H_2$ and the Co complexes provide further insight into the stronger $H_2$ binding in the m-dobdc complex. TABLE 25 breaks down the charge transfer term into forward and backward charge donation from the $H_2$ to the complex.

TABLE 25

Forward and backbonding contributions to the change transfer term for the dobdc and m-dobdc model complexes.

| | Energy (kJ/mol) | |
|---|---|---|
| | dobdc | m-dobdc |
| $H_2 \rightarrow$ CO bonding | −9.1 | −11.8 |
| Co $\rightarrow H_2$ backbonding | −3.4 | −5.3 |

In both cases, the largest portion of this charge transfer comes from the $H_2$ σ orbital to the unoccupied orbitals on the Co complex. The nature of the backbonding from the complex to $H_2$, however, is quite different as can be seen by looking at the complementary occupied virtual orbital pairs (COVPs) that contribute most to charge transfer. FIG. 8c-d shows the most important COVPs for the backbonding interactions. In the dobdc complex, the occupied orbital appears to be a primarily $d_{z^2}$ orbital on the Co center, while in the m-dobdc complex, the donating orbital includes contributions from the pi system of the linker. This increased backbonding in m-dobdc agrees with the redshift seen in the $H_2$ infrared spectra in the $M_2$ (m-dobdc) complexes. This extra interaction with the linker in the m-dobdc complex, coupled with the larger polarization, is the key difference between these two systems and helps to elucidate the stronger $H_2$ binding seen in $M_2$ (m-dobdc) versus $M_2$ (dobdc); this suggests that increasing donation to the alpha carbon of the linker may improve hydrogen binding. TABLE 26 breakdowns the energies of the most important forward bonding and backbonding charge transfer COVPs for the dobdc and m-dobdc complexes.

TABLE 26

Breakdown of the energies of the most important forward bonding and backbonding charge transfer COVPs for the dobdc and m-dobdc complexes.

| | | Energy (kJ/mol) | |
|---|---|---|---|
| | COVP | dobdc complex | m-dobdc complex |
| Backbonding | 1 | −0.43 | −0.84 |
| | 2 | −0.33 | −0.84 |
| | 3 | −0.32 | −0.51 |

TABLE 26-continued

Breakdown of the energies of the most important forward bonding and backbonding charge transfer COVPs for the dobdc and m-dobdc complexes.

| | | Energy (kJ/mol) | |
|---|---|---|---|
| | COVP | dobdc complex | m-dobdc complex |
| Forward bonding | 1 | −3.29 | −3.62 |
| | 2 | −2.25 | −3.58 |
| | 3 | −2.17 | −2.30 |
| | 4 | −1.36 | −2.25 |

Figure 67:
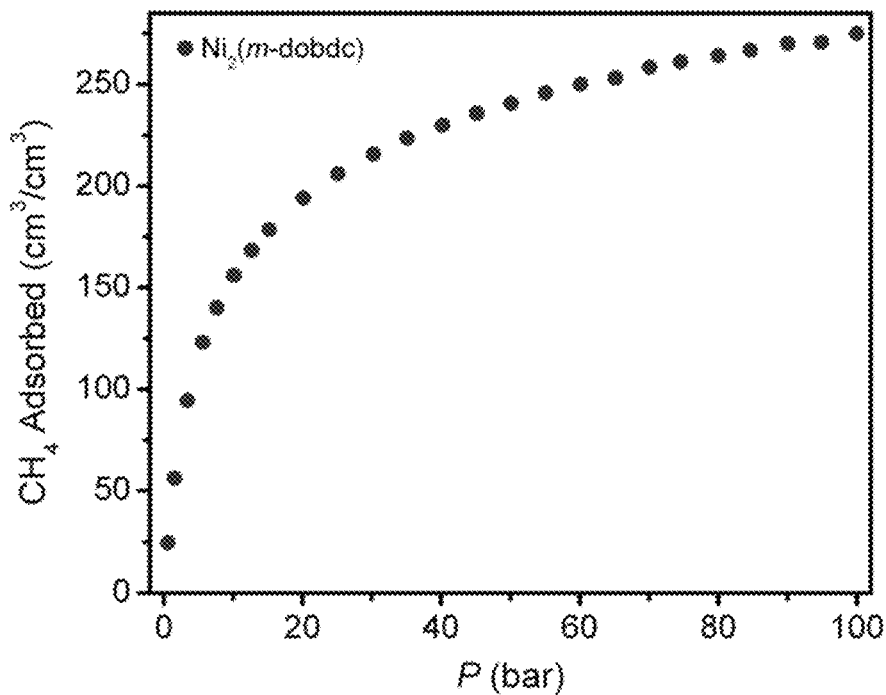
FIG. 67 shows the high-pressure methane uptake isotherm of $Ni_2$ (m-dobdc) at 25° C.
Figure 68:
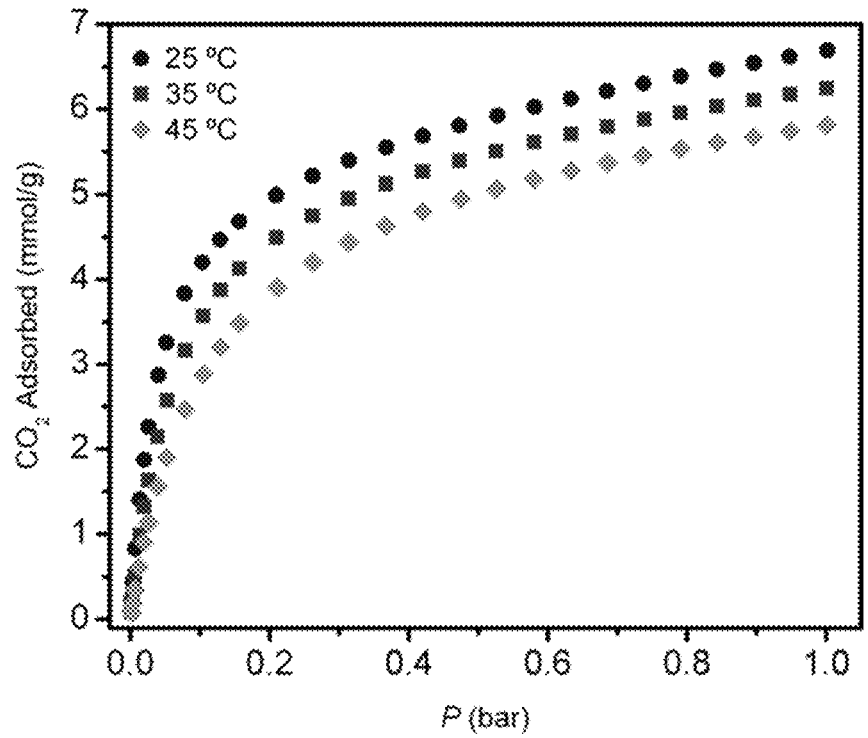
FIG. 68 shows the $CO_2$ uptake isotherms of $Ni_2$ (m-dobdc) at three different temperatures (25° C.—top; 35° C.—middle; 45° C.—bottom).

Preliminary results of methane and $CO_2$ storage suggest that other gases can indeed be stored in the $M_2$ (m-dobdc) frameworks. A high-pressure methane isotherm (FIG. 67) of the $CH_4$ uptake of $Ni_2$ (m-dobdc) at 25° C. which has comparable uptake to that of other metal-organic frameworks. Furthermore, $CO_2$ uptake for the same sample is seen in FIG. 68, which is also comparable to that of other metal-organic frameworks known in the art. Further studies are underway to understand the properties of these and other gases in the $M_2$ (m-dobdc) series of metal-organic frameworks.

Overall, the experimental and computational data has shown that a structurally new metal organic framework, $M_2$ (m-dobdc), can be synthesized with a variety of $M^{2+}$ cations ($Mg^{2+}$, $Mn^{2+}$, $Fe^{2+}$, $Co^{2+}$, and $Ni^{2+}$) to form an isostructural series. The molecule $H_2$ was used as a probe of the interaction of molecules with the high density of open metal coordination sites (exposed cation sites) present in this framework. Adsorption isotherms determined the uptake of $H_2$ of these frameworks and the fits to the adsorption isotherm data were used to determine the isosteric heats of $H_2$ adsorption in the $M_2$ (m-dobdc) series. Neutron diffraction identified the binding sites of $H_2$ in the pores of the framework, and infrared spectroscopy was used to confirm the stronger binding and identify the enthalpy and entropy change of $H_2$ upon adsorption to the frameworks. DFT calculations were used to identify the orbital and energetic interactions that lead to this higher binding enthalpy of $H_2$ to the open metal coordination sites in the $M_2$ (m-dobdc) series. It was shown that these open coordination sites can bind $H_2$ more strongly than other similar frameworks due to structural changes that elicit an electronic change in the framework. Specifically, a more positively charged metal cation and a different interaction between the orbitals in the $H_2$ and the MOF as compared to similar frameworks is shown as the cause of this stronger binding of $H_2$. It is expected that, based on the increased positive charge at the metal centers, this stronger interaction could be applied to many other molecules that can interact with strong Lewis acids in order to elicit the adsorption, absorption, storage, capture, or separations of these molecules. Additionally, post-synthetic modification of this framework with reactants could be advantageous due to the change in the metal cation.

A number of embodiments have been described herein. Nevertheless, it will be understood that various modifications may be made without departing from the spirit and scope of this disclosure. Accordingly, other embodiments are within the scope of the following claims.

What is claimed is:

1. A porous metal-organic framework (MOF) comprising a plurality of cores, wherein the plurality of cores comprises two or more metals, metal ions, and/or metal containing complexes that are linked together by forming covalent bonds with oxide and/or carboxylate linking clusters of 4,6-dioxido-1,3-benzenedicarboxylate ("m-dobdc") based linking moieties.

2. The MOF of claim 1, wherein one or more cores comprise linking moieties having a structure of Formula I:

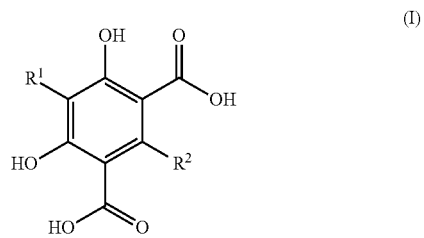

(I)

wherein,
R$^1$-R$^2$ are independently selected from H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted heteroaryl, CN, CO, NH$_2$, OR, NR$_2$, PR$_2$, SR, F, Cl, Br, and I.

3. The MOF of claim 1, wherein one or more cores comprise linking moieties having a structure of Formula I:

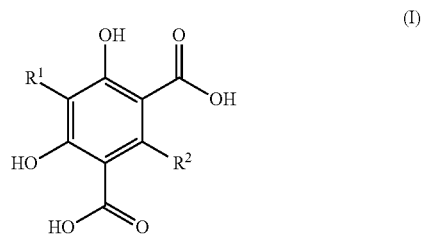

(I)

wherein,
R$^1$-R$^2$ are independently selected from H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$) alkynyl, optionally substituted ($C_1$-$C_5$)heteroalkynyl, optionally substituted aryl, optionally substituted heteroaryl, NH$_2$, NR$_2$, OR, PR$_2$, SR, F, Cl, Br, and I.

4. The MOF of claim 1, wherein one or more cores comprise linking moieties having a structure of Formula I(a):

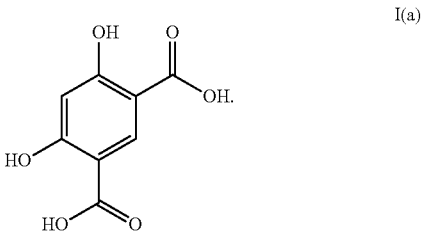 [SMILES: O=C(O)c1cc(C(=O)O)c(O)cc1O]

(I(a))

5. The MOF of claim 1, wherein the one or more cores comprise metals, metal ions, and/or metal containing complexes that are selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and any combination thereof, including any complexes which contain the metals or metal ions listed above, and any corresponding metal salt counteranions.

6. The MOF of claim 5, wherein the one or more cores comprise metal ions selected from $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

7. The MOF of claim 5, wherein the one or more cores comprise metal ions selected from $Mg^{2+}$, $Mn^{2+}$, $Fe^{2+}$, $Co^{2+}$, and $Ni^{2+}$.

8. The MOF of claim 1, wherein pores of the MOF are activated by removal of any guest molecules and/or solvent.

9. The MOF of claim 1, wherein the MOF is reacted with one or more post framework reactants.

10. The MOF of claim 9, wherein one or more post framework reactants adds at least one effect to the MOF selected from:
- modulates the gas storage ability of the MOF;
- modulates the sorption properties of the MOF;
- modulates the gas separation properties of the MOF;
- modulates the adsorbate storage ability of the MOF;
- modulates the adsorbate separation ability of the MOF;
- modulates the density of exposed metal cation sites;
- modulates the charge distribution in the framework;
- modulates the charge density at the exposed metal cation site;
- modulates the pore size of the MOF;
- modulates the catalytic activity of the MOF;
- modulates the conductivity of the MOF; and
- modulates the sensitivity of the MOF to the presence of an analyte of interest.

11. The MOF of claim 1, further comprising one or more absorbed or adsorbed chemical species.

12. The MOF of claim 11, wherein the adsorbed or absorbed chemical species is selected from gases, optionally substituted ($C_1$-$C_{25}$) organic molecules, inorganic molecules, liquids, and combinations thereof.

13. The MOF of claim 12, wherein the adsorbed or absorbed chemical species is hydrogen.

14. A method to separate or store one or more gases from a mixed gas mixture comprising contacting the gas mixture with the MOF of claim 1.

15. The method of claim 14, wherein a gas that is separated from the gas mixture and stored is hydrogen.

16. The method of claim 14, wherein the gas mixture comprises hydrogen gas formed from a steam reforming process, a electrolysis process, or a thermolysis process.

17. A method to separate or store one or more adsorbates from a mixture of adsorbates comprising contacting the mixture with the MOF of claim 1.

18. A device comprising the MOF of claim 1, or a mixture comprising the MOF of claim 1 and a binder.

19. The device of claim 18, wherein the device is a gas storage or gas separation device.

20. The device of claim 19, wherein the gas storage or gas separation device is selected from purifiers, filters, scrubbers, pressure or temperature swing adsorption devices, hollow fiber membranes, ceramic membranes, cryogenic air separation devices, and hybrid gas separation devices.

21. The MOF of claim 1, wherein the MOF further comprises an adsorbed or absorbed chemical species is selected from methane, natural gas, carbon dioxide, carbon monoxide, oxygen, nitrogen, helium, neon, argon, krypton, xenon, ethane, ethylene, acetylene, propane, propylene, butane, 2-methylpropane, 1-butene, cis-2-butene, trans-2-butene, 2-methylpropene, ammonia, $SO_2$, $SO_3$, NO, $NO_2$, $N_2O$, or other adsorbates in a gas or liquid phase.

22. The MOF of claim 1, wherein exposed metal cation sites (open metal coordination sites) adsorb, absorb, or interact with a substrate or guest in the MOF.

23. The MOF of claim 1, wherein the MOF is incorporated into a membrane.

24. The MOF of claim 1, wherein the MOF is coated on a surface.

25. A method for the separation of one or more components from a mixture, comprising:
contacting the MOF of claim 1 with a mixture selected from $O_2$/air, $CO_2$/$N_2$, $CO_2$/$H_2$, CO/$H_2$, ethane/ethylene, propane/propylene/acetylene, saturated/unsaturated hydrocarbons, methane purification, butene isomer separation (1-butene, cis-2-butene, trans-2-butene, isobutylene), mixtures of hexane isomers, and BTEX mixtures (benzene, toluene, ethylbenzene, p-xylene, o-xylene, and m-xylene).

26. A catalyst or a vehicle for a catalyst comprising the MOF of claim 1.

* * * * *